United States Patent
Peiffer et al.

(10) Patent No.: US 11,433,230 B2
(45) Date of Patent: Sep. 6, 2022

(54) DEVICES, SYSTEMS, AND METHODS FOR DELIVERING ELECTRICAL CURRENT TO THE BODY

(71) Applicant: palmm Co., Mountain View, CA (US)

(72) Inventors: Véronique Paule-Alberte Daniëlle Peiffer, Mountain View, CA (US); Daniel Elliott Francis, Mountain View, CA (US); Jarren Armond Baldwin, Oakland, CA (US)

(73) Assignee: PALMM CO., Mountain View, CA (US)

( * ) Notice: Subject to any disclaimer, the term of this patent is extended or adjusted under 35 U.S.C. 154(b) by 49 days.

(21) Appl. No.: 16/745,130

(22) Filed: Jan. 16, 2020

(65) Prior Publication Data

US 2020/0222686 A1 Jul. 16, 2020

Related U.S. Application Data

(60) Provisional application No. 62/902,137, filed on Sep. 18, 2019, provisional application No. 62/793,217, filed on Jan. 16, 2019.

(51) Int. Cl.
*A61N 1/04* (2006.01)
*A61N 1/30* (2006.01)
*A61N 1/32* (2006.01)

(52) U.S. Cl.
CPC .......... *A61N 1/0428* (2013.01); *A61N 1/303* (2013.01); *A61N 1/325* (2013.01)

(58) Field of Classification Search
None
See application file for complete search history.

(56) References Cited

U.S. PATENT DOCUMENTS

| | | | |
|---|---|---|---|
| 4,164,226 A | 8/1979 | Tapper | |
| 4,211,222 A | 7/1980 | Tapper | |
| 4,485,426 A | 11/1984 | Kerls | |
| 5,067,478 A | 11/1991 | Berlant | |
| (Continued) | | | |

FOREIGN PATENT DOCUMENTS

| | | |
|---|---|---|
| EP | 1400182 A1 | 3/2004 |
| EP | 1158919 B1 | 6/2005 |
| (Continued) | | |

OTHER PUBLICATIONS

"Bionicare Hand System," 2013, pp. 1-2, VQ OrthoCare, Irvine, CA, United States of America.

(Continued)

*Primary Examiner* — Brian T Gedeon
(74) *Attorney, Agent, or Firm* — Fortem IP LLP; Matthew Lincicum

(57) ABSTRACT

Electrical current can be delivered to the skin to treat hyperhidrosis or other conditions using wearable and non-wearable devices. Wearable devices to deliver electrical current can include an inner assembly that carries one or more electrodes and an outer assembly that can be worn over the inner assembly. Contact between electrodes and the user's skin can be promoted using suction, support components, or filler materials. Non-wearable devices can be grasped by a user or otherwise placed into contact with a treatment site for delivery of electrical current to the user's skin. Electrode lay-out for wearable and non-wearable devices can be optimized for current density distribution across the electrode.

15 Claims, 41 Drawing Sheets

(56) References Cited

U.S. PATENT DOCUMENTS

| | | | |
|---|---|---|---|
| 5,561,856 A | 10/1996 | Pesco | |
| 5,771,901 A | 6/1998 | Obrien | |
| 6,006,130 A | 12/1999 | Higo et al. | |
| 6,148,231 A | 11/2000 | Henley | |
| 6,223,076 B1 | 4/2001 | Tapper | |
| 6,336,049 B1 | 1/2002 | Kinbara et al. | |
| 6,895,271 B2 | 5/2005 | Henley | |
| 6,904,614 B2 | 6/2005 | Yamazaki et al. | |
| 7,012,797 B1 | 3/2006 | Delida | |
| 7,115,123 B2 | 10/2006 | Knowlton et al. | |
| 7,643,874 B2 | 1/2010 | Nitzan et al. | |
| 8,150,525 B2 | 4/2012 | Fassih et al. | |
| 8,989,875 B2 | 3/2015 | Grob et al. | |
| 9,089,684 B2 | 7/2015 | Axelgaard | |
| 9,161,393 B2 | 10/2015 | Kaiserman et al. | |
| 10,362,989 B2 | 7/2019 | McMillen et al. | |
| 10,406,348 B2 | 9/2019 | Huelman et al. | |
| 2004/0039328 A1 | 2/2004 | Henley | |
| 2004/0044384 A1 | 3/2004 | Leber et al. | |
| 2004/0237170 A1 | 12/2004 | Yamazaki et al. | |
| 2004/0267169 A1 | 12/2004 | Sun et al. | |
| 2006/0276741 A1 | 12/2006 | Henley | |
| 2008/0195176 A1 | 8/2008 | Stefano et al. | |
| 2010/0057147 A1 | 3/2010 | Fassih et al. | |
| 2011/0118656 A1 | 5/2011 | Eckhoff et al. | |
| 2011/0213295 A1 | 9/2011 | Henley et al. | |
| 2011/0306921 A1 | 12/2011 | Hawley | |
| 2012/0059290 A1 | 3/2012 | Yip | |
| 2013/0035650 A1 | 2/2013 | Wang | |
| 2015/0306373 A1 | 10/2015 | Bouton et al. | |
| 2016/0346530 A1 | 12/2016 | Jeffery et al. | |
| 2017/0056644 A1 | 3/2017 | Chahine et al. | |
| 2017/0354816 A1 | 12/2017 | Huelman et al. | |
| 2018/0235293 A1 | 8/2018 | Lee et al. | |
| 2019/0216147 A1 | 7/2019 | Lamontia et al. | |

FOREIGN PATENT DOCUMENTS

| | | | |
|---|---|---|---|
| KR | 200350353 Y1 | 5/2004 | |
| KR | 20090098541 A | 9/2009 | |
| WO | 2015183690 A1 | 12/2015 | |
| WO | 2017201525 A1 | 11/2017 | |
| WO | 2020150502 A1 | 7/2020 | |

OTHER PUBLICATIONS

Matsuhisa et al., "Printable conductors with a high conductivity for electronic textile applications", Nature Communications, vol. 6, Jun. 25, 2015.

International Search Report and Written Opinion dated Apr. 20, 2020, International Application No. PCT/US2020/013924, 16 pages.

DEVICES, SYSTEMS, AND METHODS FOR DELIVERING ELECTRICAL CURRENT TO THE BODY

CROSS-REFERENCE TO RELATED APPLICATIONS

This application claims the benefit of priority to U.S. Provisional Patent Application No. 62/793,217, filed Jan. 16, 2019, and to U.S. Provisional Patent Application No. 62,902,137, filed Sep. 18, 2019, each of which is hereby incorporated by reference in its entirety.

TECHNICAL FIELD

The present technology relates generally to devices, systems and methods for delivery of electrical current to the body or body parts, for example to devices, systems and methods for delivery of electrical current to the skin and their use in the management of hidrosis, treatment of hyperhidrosis or alleviation of other problems or conditions.

BACKGROUND

Sweating (hidrosis) can be bothersome to the individual who experiences it, certainly if the levels of sweat are excessive. Hyperhidrosis, or chronic excessive sweating, is caused by overactivity of the sympathetic nervous system that results in a dramatically increased sweat production, far beyond what is required for thermal regulation. People who are not familiar with the condition may not appreciate that hyperhidrosis is the dermatologic condition with the most dramatic impact on quality of life, worse than dermatitis, eczema and psoriasis. Seventy-five percent of sufferers report that the condition affects their emotional health and the prevalence of depression is tripled in this population. The condition can be particularly debilitating during times in life in which social interactions are crucially important. The youngest sufferers get bullied at school when required to hold hands, or are embarrassed when they hand in to their teacher paperwork soaked by perspiration. The condition is also particularly debilitating for adolescents: it affects them emotionally, for example feeling embarrassed when holding hands with someone. Sweaty hands also add pressure during job interviews, with more than 50% of adult patients reporting that the condition has negatively affected them in their professional career. Hidrosis (sweating) that does not reach the medical level of severity may be similarly bothersome to some individuals.

Current treatment options for hyperhidrosis each have at least one major drawback. Antiperspirants are prescribed as first-line treatment, but they are typically ineffective. Botulinum toxin injections can be used, but they are painful and expensive. Systemic medications, such as anticholinergics, are greatly limited by their adverse effects. Sympathetic (thoracic) surgery is an effective but invasive treatment that carries a significant risk of developing compensatory sweating in other body areas such as the chest and back. For the management of hidrosis any of these options would be cumbersome, invasive and/or expensive.

Another existing treatment leverages iontophoresis, a technique that is believed to introduce ions, electrons, or energy into the body, or to change or create an electric potential, or electrochemical gradients, using electrical current, or to transport ions across a membrane or into a tissue. It is a non-invasive technique that has a number of applications, including transdermal drug delivery to a pre-selected current delivery area, diagnosis of cystic fibrosis, and treatment of excessive sweating. Commercially available iontophoresis methods, devices and systems (that use water baths to conduct electricity to the body or body parts, e.g., the MD-2 Galvanic Iontophoresis Machine from RA Fischer, Calif.) can be inconvenient to use, for example, because they limit mobility during electrical current delivery, hence requiring a dedicated time commitment, and because they are messy to set up, may not ensure effective delivery to the entire pre-selected current delivery area, and/or can be uncomfortable for the user, for example because their use may induce bothersome tingling sensations, feeling of pins and needles, muscle tightening, erythema, or mild or severe skin or other tissue injury and/or burn.

Thus, there remains a considerable need for methods, devices and systems to deliver electrical current to the body, skin, membrane or other tissue, that are convenient in use, that ensure effective delivery to a pre-selected current delivery area, result in minimal discomfort for the user, and/or are easy to manufacture, even at scale.

BACKGROUND

The present technology relates generally to devices, systems and methods for delivery of electrical current to the body or body parts, for example to devices, systems and methods for delivery of electrical current to the skin and their use in the management of hidrosis, treatment of hyperhidrosis or alleviation of other problems or conditions. The subject technology is illustrated, for example, according to various aspects described below, including with reference to FIGS. 1-26. Various examples of aspects of the subject technology are described as numbered Clauses (1, 2, 3, etc.) for convenience. These are provided as examples and do not limit the subject technology.

1. An electrode assembly for delivery of an electrical current to skin of a user, the electrode assembly comprising:
   a first electrode comprising:
      a first conductive layer; and
      a plurality of first discrete conductive traces electrically coupled to the first conductive layer;
   a second electrode laterally spaced apart from the first electrode, the second electrode comprising:
      a second conductive layer; and
      a plurality of second discrete conductive traces electrically coupled to the second conductive layer;
   wherein the first electrode comprises a first portion and a second portion, the first portion being substantially more proximate to the second electrode than the second portion, and
   wherein a density of the first conductive traces is lower in the first portion of the first electrode than in the second portion of the first electrode.

2. The electrode assembly of Clause 1, wherein the first conductive traces are separated from one another across the conductive layer.

3. The electrode assembly of any one of the preceding Clauses, wherein the first conductive traces are not directly connected to one another.

4. The electrode assembly of Clause 1, wherein the second conductive traces are separated from one another across the conductive layer.

5. The electrode assembly of any one of the preceding Clauses, wherein the second conductive traces are not directly connected to one another.

6. The electrode assembly of any one of the preceding Clauses, wherein the second electrode comprises a third portion and a fourth portion, the third portion being substantially more proximate to the first electrode than the fourth portion, and wherein a density of the second conductive traces is lower in the third portion of the second electrode than in the fourth portion of the second electrode.

7. The electrode assembly of any one of the preceding Clauses, wherein at least some of the first conductive traces comprise elongated segments extending substantially parallel to one another and separated by gaps.

8. The electrode assembly of any one of the preceding Clauses, wherein the elongated segments have a width of between about 0.1-10 mm, and wherein the gaps have a width of between about 0.05-2 mm.

9. The electrode assembly of any one of the preceding Clauses, further comprising a power source having a first terminal electrically coupled to at least one of the first conductive traces and a second terminal electrically coupled to at least one of the second conductive traces.

10. The electrode assembly of any one of the preceding Clauses, wherein the first conductive traces have a higher electrical conductivity than the first conductive layer, and wherein the second conductive traces have a higher electrical conductivity than the second conductive layer.

11. The electrode assembly of any one of the preceding Clauses, wherein the first conductive layer and the second conductive layer each comprises at least one of: a conductive ink, carbon, silver, platinum, stainless steel, copper, gold, or alloy(s) thereof.

12. The electrode assembly of any one of the preceding Clauses, further comprising a bolster layer disposed over and in electrical communication with both the first conductive layer and the second conductive layer.

13. An electrode comprising:
a conductive layer having a first electrical conductivity;
a first conductive trace coupled to the conductive layer and configured to be electrically coupled to a power source; and
a second conductive trace coupled to the conductive layer at a position spaced apart from the first conductive trace, the first and second conductive traces having a second electrical conductivity greater than the first electrical conductivity,
wherein the electrode is configured such that at least some of an electrical current supplied to the first conductive trace from the power source passes through the conductive layer and to the second conductive trace.

14. The electrode of any one of the preceding Clauses, wherein at least one of the conductive layer, the first conductive trace, or the second conductive trace is configured to deliver electrical current to user's skin or other bodily tissue 15. The electrode of any one of the preceding Clauses, wherein a density of conductive traces is higher in a first portion of the electrode than a density of conductive traces in a second portion of the electrode.

16. The electrode of any one of the preceding Clauses, wherein the first and second conductive traces each comprise elongated segments having a width of between about 0.1-10.0 mm.

17. The electrode of any one of the preceding Clauses, wherein the first and second conductive traces are spaced apart from one another by between about 0.05-2.0 mm.

18. The electrode of any one of the preceding Clauses, wherein at least portions the first and second conductive traces extend substantially parallel to one another.

19. The electrode of any one of the preceding Clauses, wherein the electrode is configured to deliver energy to skin or other bodily tissue.

20. The electrode of any one of the preceding Clauses, wherein the energy comprises at least one of: electrical current, direct current, alternating current, electromagnetic energy (e.g., radio wave, microwave, infrared, X-ray), ultrasound, laser, thermal energy, chemical energy, or vibration.

21. The electrode of any one of the preceding Clauses, wherein each of the first conductive layer and the second conductive layer comprises at least one of: a conductive ink, carbon, silver, platinum, stainless steel, copper, gold, or an alloy thereof.

22. The electrode of any one of the preceding Clauses, further comprising a bolster layer disposed over the conductive layer.

23. The electrode of any one of the preceding Clauses, wherein the second electrical conductivity is at least 100 times greater than the first electrical conductivity.

24. A method of dispersing an electrical current across an electrode, the method comprising:
supplying the electrical current from a power source to a first conductive element coupled to a conductive layer of the electrode, the first conductive element having a higher electrical conductivity than the conductive layer; and
passing the electrical current from the first conductive element to the conductive layer, and passing at least some of the electrical current from the conductive layer to a plurality of additional conductive elements coupled to the conductive layer at positions spaced apart from the first conductive element, the additional conductive elements having a higher electrical conductivity than the conductive layer.

25. The method of any one of the preceding Clauses, further comprising passing at least some current from the conductive layer to an electrolyte-filled bolster material.

26. The method of any one of the preceding Clauses, passing at least some current from the conductive layer and from the conductive traces into a user's skin.

27. The method of any one of the preceding Clauses, further comprising passing at least some of the electrical current from the electrolyte-filled bolster material into a user's skin.

28. The method of any one of the preceding Clauses, further comprising delivering a pre-determined distribution of current into the user's skin.

29. The method of any one of the preceding Clauses, wherein a concentration of conductive elements is higher in a first region of the electrode than in a second region of the electrode, and wherein a current density across the electrode is higher in the first region than in the second region.

30. The electrode of any of the preceding Clauses, wherein the electrode is configured to deliver energy to skin or other bodily tissue.

31. The electrode of any of the preceding Clauses, wherein the electrode is configured to deliver electrical current to skin or other bodily tissue.

32. The electrode of any of the preceding Clauses, wherein the electrode is configured to deliver direct current to skin or other bodily tissue.

33. The electrode of any of the preceding Clauses, wherein the first level of conductivity is between about 0.01-0.05 S/m, between about 0.05-0.1 S/m, between about 0.1-1 S/m or between about 1-10 S/m.

34. The electrode of any of the preceding Clauses, wherein the second level of conductivity is higher than the first level of conductivity.

35. The electrode of any of the preceding Clauses, wherein the conductive traces have a width of between about 1-10 μm, between about 10-100 μm, between about 0.1-1 mm, between about 1 mm-1 cm, or between about 1-2 cm.

36. The electrode of any of the preceding Clauses, wherein at least portions of at least two conductive traces are substantially parallel to each other.

37. The electrode of any of the preceding Clauses, wherein a density of conductive traces is higher in a first portion of the electrode than a density of conductive traces in a second portion of the electrode.

38. The electrode of any of the preceding Clauses, wherein the electrode is a part of an electrode assembly containing at least two electrodes.

39. The electrode assembly of any of the preceding Clauses, wherein at least two electrodes each further comprises a non-conductive layer.

40. The electrode assembly of any of the preceding Clauses, wherein at least two electrodes are mechanically coupled to each other.

41. The electrode assembly of any of the preceding Clauses, wherein the first conductive layer of the first electrode is continuous with the first conductive layer of the second electrode.

42. The electrode assembly of any of the preceding Clauses, wherein a density of conductive traces of the first electrode is substantially lower in an area substantially closer to the second electrode than a density of conductive traces in an area substantially further away from the second electrode.

43. The electrode of any of the preceding Clauses, wherein space between adjacent conductive traces or segments of the second conductive layer defines trace-to-trace, trace-to-segment or segment-to-segment gaps.

44. The electrode of any of the preceding Clauses, wherein the trace-to-trace, trace-to-segment or segment-to-segment gaps have a width of between about 1-10 μm, between about 10-100 μm, between about 0.1-1 mm, between about 0.1-1 cm, or between about 1-2 cm.

45. The electrode of any of the preceding Clauses, wherein at least portions of at least two of the trace-to-trace, trace-to-segment or segment-to-segment gaps are substantially parallel to each other.

46. The electrode of any of the preceding Clauses, wherein the first conductive layer comprises at least one of: a conductive gel, an electrolyte-containing foam, a hydrogel, a carbon-doped polymer.

47. The electrode of any of the preceding Clauses, wherein the second conductive layer comprises at least one of: a conductive ink, carbon, silver, platinum, stainless steel, copper, gold.

48. The electrode assembly of any of the preceding Clauses, wherein the first electrode is connected with a first terminal of a power source through a first conductive connector, and the second electrode is connected with a second terminal of the power source through a second conductive connector.

49. The electrode assembly of any of the preceding Clauses, wherein the first conductive connector and the second conductive connector are conductive wires or traces.

50. The electrode assembly of any of the preceding Clauses, wherein the conductive layer of the first electrode defines a first perimeter and the conductive layer of the second electrode defines a second perimeter.

51. The electrode assembly of any of the preceding Clauses, wherein an electrical connection point between the first electrode and the first conductive connector is located in an area substantially closer to a portion of the first perimeter further away from the second electrode, and wherein an electrical connection point between the second electrode and the second conductive connector is located in an area substantially closer to a portion of the second perimeter further away from the first electrode.

52. A method of dispersing an electrical current, the method comprising of injecting the electrical current from a power source into a first conductive material, from the first conductive material into a second conductive material and an electrolyte-filled bolster material, and from the second conductive material into a third conductive material and the electrolyte-filled bolster material, wherein less than 100% of the electrical current travels through the third conductive material.

53. An electrode assembly for delivery of energy to skin or other bodily tissue of a user, the assembly comprising a first electrode and a second electrode, wherein each of the first and second electrodes have a non-uniform conductivity configured to deliver a substantially pre-determined energy density component perpendicular to the skin or other bodily tissue under each of the first and second electrodes.

54. The electrode assembly of any of the preceding Clauses, wherein the energy comprises: electrical current, electromagnetic energy (e.g., radio wave, microwave, infra-red, X-ray), ultrasound, laser, thermal energy, chemical energy, vibration or combinations thereof.

55. The electrode assembly of any of the preceding Clauses, wherein the substantially pre-determined energy density component perpendicular to the skin or other bodily tissue is substantially uniform.

56. The electrode assembly of any of the preceding Clauses, wherein the first electrode is connected with a first terminal of a power source through a first conductive connector, and the second electrode is connected with a second terminal of the power source through a second conductive connector.

57. The electrode assembly of any of the preceding Clauses, wherein the first conductive connector and the second conductive connector are conductive wires or traces.

58. The electrode assembly of any of the preceding Clauses, wherein an electrical connection point between the first electrode and the first conductive connector is located in an area substantially closer to a portion of the first perimeter further away from the second electrode, and wherein an electrical connection point between the second electrode and the second conductive connector is located in an area substantially closer to a portion of the second perimeter further away from the first electrode.

59. The electrode assembly of any of the preceding Clauses, wherein the conductivity of the first electrode is lower in an area substantially closer to the second electrode than in an area substantially further away from the second electrode.

60. The electrode assembly of any of the preceding Clauses, wherein the conductivity of the second electrode is lower in an area substantially closer to the first electrode than in an area substantially further away from the first electrode.

61. The electrode assembly of any of the preceding Clauses, wherein the first electrode and/or the second electrode each comprises two or more conductive layers.

62. The electrode assembly of any of the preceding Clauses, wherein at least a portion of one or more conductive layers of the two electrodes are continuous between the two electrodes.

63. The electrode assembly of any of the preceding Clauses, wherein the two electrodes are mechanically connected to each other.

64. The electrode assembly of any of the preceding Clauses, wherein each electrode further comprises a substantially non-conductive layer.

65. The electrode assembly of any of the preceding Clauses, wherein the two electrodes are mechanically connected.

66. An electrical circuit comprising of two electrodes, a conductive body and a shunting path between the two electrodes, wherein less than 100% of the electrical current flows through the conductive body.

67. The electrical circuit of any of the preceding Clauses, wherein the conductive body comprises at least one of: a human hand, a body part, a skin phantom, or a tissue phantom.

68. An electrode assembly for delivery of electrical current to skin of a user, the assembly comprising:
a first electrode comprising:
a first base layer;
a plurality of first conductive traces disposed over the first base layer; and
a first conductive layer disposed over the first base layer, the first conductive layer defining a first perimeter;
a second electrode laterally spaced apart from the first electrode, the second electrode comprising:
a second base layer;
a plurality of second conductive traces disposed over the second base layer; and
a second conductive layer disposed over the second base layer, the second conductive layer defining a second perimeter; and
a bolster layer disposed over the first electrode and over the second electrode, the bolster layer configured to face the skin of the user,
wherein at least one of the first conductive traces is oriented substantially parallel to a portion of the first perimeter adjacent to the second electrode,
wherein the first electrode comprises a first portion and a second portion, the first portion being more substantially more proximate to the second electrode than the second portion, and
wherein a density of the first conductive traces is lower in the first portion of the first electrode than in the second portion of the first electrode.

69. The electrode assembly of any of the preceding Clauses, wherein the electrode assembly is configured to be applied to a user's hand.

70. The electrode assembly of any of the preceding Clauses, wherein the electrode assembly is configured to be applied to a user's foot.

71. The electrode assembly of any of the preceding Clauses, wherein the electrode assembly is configured to be applied to a user's armpit.

72. The electrode assembly of any of the preceding Clauses, wherein the electrode assembly is configured to be applied to a user's face.

73. The electrode assembly of any of the preceding Clauses, wherein, when the electrode assembly is applied to the user's hand, the first electrode is positioned substantially distally with respect to the second electrode.

74. The electrode assembly of any of the preceding Clauses, wherein, when the electrode assembly is applied to the user's hand, the first electrode overlies fingers of the user's hand, and the second electrode overlies a palmar portion of the user's hand.

75. The electrode assembly of any of the preceding Clauses, wherein the conductive traces comprise at least one of: silver, silver alloy, carbon, carbon nanotubes, platinum, stainless steel, or copper.

76. The electrode assembly of any of the preceding Clauses, wherein the conductive traces comprise printed conductive ink.

77. The electrode assembly of any of the preceding Clauses, wherein the first conductive traces have a width of between about 10-100 µm, between about 0.1-1 mm, between about 1 mm-1 cm, or between about 1-2 cm.

78. The electrode assembly of any of the preceding Clauses, wherein at least some of the first conductive traces are separated from one another by a gap of between about 0.1-7 mm, between about 0.1-5 mm, about 0.5 mm, about 1 mm, about 2 mm, or about 5 mm in width.

79. The electrode assembly of any of the preceding Clauses, wherein the first conductive layer is disposed over the first conductive traces, and wherein the second conductive layer is disposed over the second conductive traces.

80. The electrode assembly of any of the preceding Clauses, wherein the first and second base layers are a continuous layer.

81. A wearable electrical current delivery device comprising:
an inner assembly comprising the electrode assembly of any of the preceding Clauses;
an outer assembly configured to be worn over the inner assembly; and
a controller unit electrically coupled to the first and second electrodes, the controller unit comprising:
a power source; and
a controller configured to deliver electrical current to the first and second electrodes.

82. The device of any of the preceding Clauses, wherein the outer assembly comprises a glove.

83. An outer assembly comprising:
a flexible glove configured to be worn over a user's hand;
a palm support configured to be disposed over or within a palmar portion of the glove such that, when the outer assembly is disposed over the user's hand, the palm support covers at least part of a region between a distal palmar crease, a thenar eminence, and a hypothenar eminence of the user's hand, but does not extend over a user's wrist nor over a user's metacarpophalangeal thumb joint, the palm support being substantially more rigid than the glove; and
one or more palm support fasteners configured to secure the palm support with respect to the glove, the palm support fastener(s) configured to couple two or more connection points on a dorsal side of the glove.

84. The outer assembly of any of the preceding Clauses, wherein the palm support comprises a palm-facing surface configured to face a user's palm.

85. The outer assembly of any of the preceding Clauses, wherein the outer surface defines a contour that has a concave portion configured to accommodate the thenar eminence of the user's hand.

86. The outer assembly of any of the preceding Clauses, wherein the palm support fastener comprises a cord coupled to a plurality of connection points on the dorsal side of the outer assembly such that retraction of the cord tightens the outer assembly with respect to a user's hand when worn by the user.

87. The outer assembly of any of the preceding Clauses, wherein the palm support fastener comprises a cord coupled to a plurality of connection points on the dorsal side of the outer assembly such that retraction of the cord promotes contact between the inner assembly and a user's hand when worn by the user.

88. A device comprising:
the outer assembly of any of the preceding Clauses; and
an inner assembly configured to be disposed within the glove, the inner assembly carrying one or more electrodes configured to deliver current to the user's skin.

89. A device comprising:
the outer assembly of any of the preceding Clauses; and
a controller unit electrically coupled to the first and second electrodes, the controller unit comprising:
a power source; and
a controller configured to deliver electrical current to the first and second electrodes.

90. The outer assembly of any of the preceding Clauses, wherein the palm support comprises a substantially convex surface configured to face the user's skin when the glove is worn by the user.

91. The outer assembly of any of the preceding Clauses, wherein the palm support comprises a substantially flat or concave surface configured to face away from the user's skin when the glove is worn by the user.

92. The outer assembly of any of the preceding Clauses, wherein the palm support has a thickness of about 2 cm or less, about 5 mm or less, about 3 mm or less, or about 1 mm or less.

93. The outer assembly of any of the preceding Clauses, wherein the palm support has a substantially convex palm-facing surface with a greatest depth of between about 3-15 mm.

94. The outer assembly of any of the preceding Clauses, further comprising a cord lock configured to releasably retain the cord in position with respect to the connection points.

95. The outer assembly of any of the preceding Clauses, wherein the connection points comprise grommets, apertures, hooks, or slots configured to receive the cord therethrough.

96. An electrode assembly comprising:
a first electrode carried configured to be coupled to a first terminal of a power source;
a second electrode configured to be coupled to a second terminal of the power source; and
a barrier laterally separating the first electrode and the second electrode, the barrier being less conductive than the first and second electrodes,
wherein the first electrode comprises a first portion and a second portion, the first portion being substantially more proximate to the barrier than the second portion, and
wherein the first electrode has a non-uniform conductivity such that the second portion is more conductive than the first portion.

97. A wearable device for delivering electrical current comprising:
an inner assembly configured to be worn by a user, the inner assembly carrying the electrode assembly of any of the preceding Clauses.

98. The device of any of the preceding Clauses, wherein the second electrode comprises a third portion and a fourth portion, the third portion of the second electrode being substantially more proximate to the barrier than the fourth portion of the second electrode, and wherein the second electrode has a non-uniform conductivity such that the fourth portion of the second electrode is more conductive than the third portion of the second electrode.

99. The device of any of the preceding Clauses, wherein the second portion of the first electrode is more conductive than the first portion of the first electrode by a factor of between about 1.01-2×, between about 2-5×, between about 5-10×, between about 10-100×, or between about 100-1000×.

100. The device of any of the preceding Clauses, wherein the inner assembly is substantially hand-shaped and configured to be worn over a hand of the user, and wherein the second portion of the first electrode is disposed over one or more fingertip regions of the inner assembly.

101. The device of any of the preceding Clauses, wherein the inner assembly is substantially hand-shaped and configured to be worn over a hand of the user, wherein the first electrode extends over four finger regions of the inner assembly, and wherein the second electrode extends over a palmar region of the inner assembly.

102. The device of any of the preceding Clauses, wherein the first electrode further extends over a thumb region of the inner assembly.

103. The device of any of the preceding Clauses, wherein the inner assembly is substantially hand-shaped and configured to be worn over a hand of the user, wherein the second electrode extends over four finger regions of the inner assembly, and wherein the first electrode extends over a palmar region of the inner assembly.

104. The device of any of the preceding Clauses, wherein the first electrode comprises a first conductive material and a second conductive material that is more conductive than the first conductive material, and wherein the second portion of the first electrode has a greater concentration of the second conductive material than the first portion of the first electrode.

105. The device of any of the preceding Clauses, wherein the first electrode comprises a resistive material, and wherein the first portion of the first electrode has a greater concentration of the resistive material than the second portion of the first electrode.

106. The device of any of the preceding Clauses, wherein the non-uniform conductivity defines a gradient of increasing conductivity from a first region of the first electrode to a second region of the first electrode.

107. The device of any of the preceding Clauses, wherein the non-uniform conductivity defines a step-wise increase in conductivity from a first region of the first electrode to a second region of the first electrode.

108. The device of any of the preceding Clauses, wherein the inner assembly is stretchable.

109. The device of any of the preceding Clauses, wherein the inner assembly comprises a base layer, and wherein each of the first and second electrodes comprise:
a plurality of conductive traces disposed over the base layer; and
a conductive layer disposed over the conductive traces.

110. The device of any of the preceding Clauses, wherein the base layer is stretchable.

111. The device of any of the preceding Clauses, wherein the base layer is substantially non-conductive.

112. The device of any of the preceding Clauses, wherein the conductive traces are non-uniformly arranged over the conductive layer.

113. The device of any of the preceding Clauses, wherein the conductive traces comprise at least one of: silver, silver alloy, carbon, carbon nanotubes, platinum, stainless steel, or copper.

114. The device of any of the preceding Clauses, wherein the conductive traces comprise printed conductive ink.

115. The device of any of the preceding Clauses, wherein the conductive traces are more concentrated in the second portion of the first electrode than in the first portion of the first electrode.

116. The device of any of the preceding Clauses, wherein the conductive traces have a width of between about 1-10 μm, 10-100 μm, between about 0.1-1 mm, between about 1 mm-1 cm, or between about 1-2 cm.

117. The device of any of the preceding Clauses, wherein the conductive layer comprises a sheet of conductive material.

118. The device of any of the preceding Clauses, wherein the conductive layer comprises a sheet of varying thickness.

119. The device of any of the preceding Clauses, wherein the conductive layer comprises at least one of: silver, silver alloys, carbon, carbon nanotubes, platinum, stainless steel or copper.

120. The device of any of the preceding Clauses, further comprising a bolster layer disposed over the conductive layer.

121. The device of any of the preceding Clauses, wherein the bolster layer comprises water-absorbent material.

122. The device of any of the preceding Clauses, wherein the bolster layer comprises one or more of: felt, microfiber, polyurethane foam, PVA foam, or a hydrogel.

123. The device of any of the preceding Clauses, further comprising a non-conductive encapsulant disposed over at least a portion of the conductive traces.

124. The device of any of the preceding Clauses, wherein the inner assembly is configured to be worn over a user's hand.

125. The device of any of the preceding Clauses, wherein the inner assembly is configured to be worn over a user's foot.

126. The device of any of the preceding Clauses, further comprising an outer assembly configured to be worn by the user over the inner assembly.

127. The device of any of the preceding Clauses, wherein the outer assembly comprises a glove.

128. The device of any of the preceding Clauses, further comprising a controller unit electrically coupled to the first and second electrodes, the controller unit comprising:
the power source; and
a controller configured to deliver electrical current to the first and second electrodes carried by the inner assembly.

129. The device of any of the preceding Clauses, further comprising a support configured to promote contact between a portion of the inner assembly and skin of the user.

130. The device of any of the preceding Clauses, wherein the support comprises a palm support configured to promote contact between a palmar portion of the inner assembly and a hand of the user.

131. The device of any of the preceding Clauses, wherein the palm support comprises a substantially convex outer surface configured to face towards the palmar portion of the inner assembly.

132. The device of any of the preceding Clauses, wherein the palm support comprises a substantially flat or concave inner surface configured to face away from the palmar portion of the inner assembly.

133. The device of any of the preceding Clauses, wherein, when the device is worn over the hand of the user, the palm support is configured to cover at least part of a region between the distal palmar crease, the thenar eminence, and the hypothenar eminence of the user's hand.

134. A wearable device for delivering electrical current comprising:
an inner assembly configured to be worn over a hand of a user;
first and second electrodes carried by the inner assembly;
an outer assembly configured to be worn by the user over the inner assembly;
a palm support configured to promote contact between a palmar portion of the inner assembly and the hand of the user; and
a controller unit electrically coupled to the first and second electrodes, the controller unit comprising:
a power source; and
a controller configured to deliver electrical current to the first and second electrodes carried by the inner assembly.

135. The device of any of the preceding Clauses, wherein the palm support comprises a substantially convex outer surface configured to face towards the palmar portion of the inner assembly.

136. The device of any of the preceding Clauses, wherein the palm support comprises a substantially flat or concave inner surface configured to face away from the palmar portion of the inner assembly.

137. The device of any of the preceding Clauses, wherein, when the device is worn over the hand of the user, the palm support is configured to cover at least part of a region between the distal palmar crease, the thenar eminence, and the hypothenar eminence of the user's hand.

138. The device of any of the preceding Clauses, wherein the palm support comprises an outer surface configured to face towards the palmar portion of the inner assembly, an inner surface configured to face away from the palmar portion of the inner assembly, the outer surface defining a contour having a concave portion configured to accommodate the thenar eminence of the user's hand.

139. The device of any of the preceding Clauses, wherein the palm support comprises a plurality of segments that are moveable with respect to one another.

140. The device of any of the preceding Clauses, wherein the segments are connected via a hinge or flexible material.

141. The device of any of the preceding Clauses, wherein the palm support has a thickness of about 2 cm or less, about 5 mm or less, about 3 mm or less, or about 1 mm or less.

142. The device of any of the preceding Clauses, wherein the palm support has a convex outer surface with a greatest depth of between about 3-15 mm.

143. The device of any of the preceding Clauses, wherein the palm support comprises a rigid material.

144. The device of any of the preceding Clauses, wherein the palm support is more rigid than the outer assembly.

145. The device of any of the preceding Clauses, wherein the palm support is removably coupled to the outer assembly.

146. The device of any of the preceding Clauses, further comprising one or more fasteners configured to secure the palm support in position with respect to the inner assembly when the outer assembly is worn over the inner assembly.

147. The device of any of the preceding Clauses, wherein fasteners comprise at least one of: a strap, a band, a cord, or a tether.

148. The device of any of the preceding Clauses, wherein the fasteners comprise one or more of: a hook-and-loop fastener, a clasp, a buckle, a button, or a cord lock.

149. The device of any one of the preceding Clauses, wherein one or more fasteners are coupled to the palm support via one or more openings formed in the palm support.

150. The device of any of the preceding Clauses, wherein the fastener is configured to extend at least partially around a backside of the outer assembly.

151. The device of any of the preceding Clauses, wherein the controller unit is configured to be removably coupled to the outer assembly.

152. The device of any of the preceding Clauses, wherein the controller unit is wearable.

153. The device of any of the preceding Clauses, wherein the inner assembly comprises a substantially non-conductive base layer, wherein the first and second electrodes are each disposed over the base layer and are separated from one another by a barrier.

154. The device of any of the preceding Clauses, wherein the barrier comprises a substantially non-conductive protrusion that projects beyond a surface of the first electrode and a surface of the second electrode.

155. The device of any of the preceding Clauses, wherein the inner assembly comprises a substantially non-conductive base layer, and wherein each of the first and second electrodes comprises:
- a conductive trace disposed over the base layer;
- a conductive layer disposed over the conductive trace; and
- a bolster layer disposed over the conductive layer.

156. The device of any of the preceding Clauses, further comprising a substantially non-conductive encapsulant disposed over least a portion of the conductive trace.

157. The device of any of the preceding Clauses, wherein the conductive trace comprises a conductive ink.

158. The device of any of the preceding Clauses, wherein the base layer is stretchable.

159. The device of any of the preceding Clauses, wherein the bolster layer comprises a water-absorbent material.

160. The device of any of the preceding Clauses, wherein the bolster layer is configured to hold an electrolyte solution.

161. The device of any of the preceding Clauses, wherein the first electrode includes a plurality of segments separated by breaks, wherein the conductive layer and the bolster layer do not extend into the breaks, and wherein the breaks are more elastic than the segments.

162. The device of any of the preceding Clauses, wherein the breaks are configured to align with bending points of a user's body.

163. A wearable iontophoresis device comprising:
- an inner assembly configured to be worn by a user;
- first and second electrodes carried by the inner assembly;
- an outer assembly configured to be worn by a user over the inner assembly;
- a suction source coupled to the outer assembly, the suction source configured to supply negative pressure to an interior region defined by the outer assembly; and
- a controller unit electrically coupled to the first and second electrodes, the controller unit comprising:
  - a power source; and
  - a controller configured to deliver electrical current to the first and second electrodes carried by the inner assembly.

164. The device of any of the preceding Clauses, wherein the suction source comprises a pump fluidically coupled to one or more one-way valves.

165. The device of any of the preceding Clauses, wherein the suction source is hand-activated.

166. The device of any of the preceding Clauses, wherein the suction source is carried by the outer assembly.

167. The device of any of the preceding Clauses, wherein the outer assembly comprises a fastener and a cuff liner configured to provide an air-tight seal against a user's body when worn by the user.

168. The device of any of the preceding Clauses, wherein the fastener is disposed along an exterior of a cuff of the outer assembly, and wherein the cuff liner is disposed along an interior of the cuff.

169. The device of any of the preceding Clauses, wherein the device is configured to be worn over a user's hand.

170. The device of any of the preceding Clauses, wherein the device is configured to be worn over a user's foot.

171. The device of any of the preceding Clauses, wherein the controller unit is configured to be removably coupled to the outer assembly.

172. The device of any of the preceding Clauses, wherein the controller unit is wearable.

173. The device of any of the preceding Clauses, wherein the inner assembly comprises a non-conductive base layer, wherein the first and second electrodes are each disposed over the base layer and are separated from one another by a barrier.

174. The device of any of the preceding Clauses, wherein the barrier comprises a non-conductive protrusion that projects beyond a surface of the first electrode and a surface of the second electrode.

175. The device of any of the preceding Clauses, wherein the inner assembly comprises a non-conductive base layer, and wherein each of the first and second electrodes comprises:
- a conductive trace disposed over the base layer;
- a conductive layer disposed over the conductive trace; and
- a bolster layer disposed over the conductive layer.

176. The device of any of the preceding Clauses, further comprising a substantially non-conductive encapsulant disposed over least a portion of the conductive trace.

177. The device of any of the preceding Clauses, wherein the conductive trace comprises a conductive ink.

178. The device of any of the preceding Clauses, wherein the base layer is stretchable.

179. The device of any of the preceding Clauses, wherein the bolster layer comprises a water-absorbent material.

180. The device of any of the preceding Clauses, wherein the bolster layer is configured to hold an electrolyte solution.

181. The device of any of the preceding Clauses, wherein the first electrode includes a plurality of segments separated by breaks, wherein the conductive layer and the bolster layer do not extend into the breaks, and wherein the breaks are more elastic than the segments.

182. The device of any of the preceding Clauses, wherein the breaks are configured to align with bending points of a user's body.

183. An iontophoresis device comprising:
- a body configured to be positioned against a user's skin at a treatment site;
- an electrode assembly configured to be removably positioned over a portion of the body, the electrode assembly carrying first and second electrodes; and a controller unit electrically coupled to the first and second electrodes, the controller unit comprising:
   a power source; and
   a controller configured to deliver electrical current to the first and second electrodes carried by the electrode assembly.

184. The device of any of the preceding Clauses, wherein the body is shaped and configured to be grasped by a user's hand.

185. The device of any of the preceding Clauses, wherein the body comprises a plurality of positioners configured to receive fingers of the user's hand when grasped by the user.

186. The device of any of the preceding Clauses, wherein the body is deformable.

187. The device of any of the preceding Clauses, wherein the controller unit includes a housing, and wherein the body is disposed over the housing.

188. The device of any of the preceding Clauses, wherein the electrode assembly comprises a non-conductive base layer, wherein the first and second electrodes are each disposed over the base layer and are separated from one another by a barrier.

189. The device of any of the preceding Clauses, wherein the barrier comprises a non-conductive protrusion that projects beyond a surface of the first electrode and a surface of the second electrode.

190. The device of any of the preceding Clauses, wherein the electrode assembly comprises a non-conductive base layer, and wherein each of the first and second electrodes comprises:
   a conductive trace disposed over the base layer;
   a conductive layer disposed over the conductive trace; and
   a bolster layer disposed over the conductive layer.

191. The device of any of the preceding Clauses, further comprising a non-conductive encapsulant disposed over least a portion of the conductive trace.

192. The device of any of the preceding Clauses, wherein the conductive trace comprises a conductive ink.

193. The device of any of the preceding Clauses, wherein the base layer is stretchable.

194. The device of any of the preceding Clauses, wherein the bolster layer comprises a water-absorbent material.

195. The device of any of the preceding Clauses, wherein the bolster layer is configured to hold an electrolyte solution.

196. A wearable iontophoresis device comprising:
   a garment configured to be worn by a user, the garment configured to be sealed against the user's body to define an interior chamber within the garment;
   one or more electrodes carried by the garment, the one or more electrodes configured to contact skin of the user when the garment is worn by the user;
   a suction source coupled to the garment, the suction source configured to supply negative pressure to the interior chamber defined by the garment; and
   a controller unit electrically coupled to the one or more electrodes, the controller unit configured to deliver electrical current to the one or more electrodes carried by the garment.

197. The device of any of the preceding Clauses, wherein the garment comprises an air-tight outer assembly and an inner assembly that can be inserted within the outer assembly, and wherein the one or more electrodes are carried by the inner assembly.

198. The device of any of the preceding Clauses, wherein the garment is configured to be worn over a user's hand.

199. The device of any of the preceding Clauses, wherein the garment is configured to be worn over a user's foot.

200. The device of any of the preceding Clauses, wherein the garment is configured to be worn over a user's under-arm region.

201. The device of any of the preceding Clauses, wherein the suction source comprises a pump fluidically coupled to one or more one-way valves.

202. The device of any of the preceding Clauses, wherein the suction source is hand-activated.

203. The device of any of the preceding Clauses, wherein the garment comprises a fastener configured to provide an air-tight seal against a user's body when worn by the user.

204. The device of any of the preceding Clauses, wherein the fastener is disposed along a cuff of the garment.

205. The device of any of the preceding Clauses, wherein the controller is configured to be removably coupled to the garment.

206. The device of any of the preceding Clauses, wherein the controller is wearable.

207. The device of any of the preceding Clauses, wherein the garment comprises a substantially non-conductive base layer, and wherein each of the one or more electrodes comprises:
   a conductive trace disposed over the base layer;
   a conductive layer disposed over the conductive trace; and
   a bolster layer disposed over the conductive layer.

208. The device of any of the preceding Clauses, further comprising a substantially non-conductive encapsulant disposed over least a portion of the conductive trace.

209. The device of any of the preceding Clauses, wherein the conductive trace comprises a conductive ink.

210. The device of any of the preceding Clauses, wherein the base layer is stretchable.

211. The device of any of the preceding Clauses, wherein the bolster layer comprises a water-absorbent material.

212. The device of any of the preceding Clauses, wherein the bolster layer is configured to hold an electrolyte solution.

213. The device of any of the preceding Clauses, wherein the electrode includes a plurality of segments separated by breaks, wherein the conductive layer and the bolster layer do not extend into the breaks, and wherein the breaks are more elastic than the segments.

214. The device of any of the preceding Clauses, wherein the breaks are configured to align with bending points of a user's body when the garment is worn by the user.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology relates to delivery of electrical current to the body and associated systems and methods of use. Some embodiments of the present technology, for example, are directed to devices for delivering electrical current to an area of a user's skin for the management of hidrosis, treatment of hyperhidrosis, or alleviation of other problems or conditions. Specific details of several embodiments of the technology are described below with reference to FIGS. 1-26.

II. OVERVIEW

Commercially available iontophoresis devices for the treatment of hyperhidrosis are inconvenient to use. Wearable iontophoresis devices are disclosed in U.S. patent application Ser. No. 15/619,398, filed Jun. 9, 2017, entitled "Devices for Delivery of Electrical Current to the Body and Related Methods for Therapy," which is hereby incorporated by reference in its entirety. The devices, systems and methods disclosed therein already offer improvement over previous iontophoresis devices. (In various embodiments, any one of the embodiments or examples described herein can be combined with or otherwise include any one of the features disclosed in the '398 patent application.) Still, a key problem with iontophoresis devices intended to be more convenient is that they do not provide effective ways to optimally cover and/or conform to the pre-selected current delivery area while remaining cost-effective. In particular, there is a need for providing improved contact between electrodes of the iontophoresis device and the pre-selected current delivery area, also referred to as treatment site (e.g., substantially a user's palm in the case of palmar hyperhidrosis, substantially the sole of a user's foot in the case of plantar hyperhidrosis, substantially the user's armpit in the case of axillary hyperhidrosis). Iontophoresis devices comprising an adhesive to promote contact to or coverage of the preselected current delivery area may become costly if they have to be disposed of after one or multiple uses, or may not be user-friendly if they have to be reused one or multiple times. Iontophoresis devices comprising a simple, unadapted garment with conductive elements (e.g., a glove, a sock, a shoe, or a section of a simple garment) may make poor or intermittent contact with the body or body part, and such contact may lead to painful sensations and hence inconvenience. Poor contact or incomplete coverage of the pre-selected current delivery area may also lead to incomplete treatment outcomes. For example, there remains a need to cover a sufficient area of the sweat glands that sweat excessively on the body or targeted body part to adequately treat hyperhidrosis using electrical current, for example the sides of the fingers for palmar hyperhidrosis, and the sides of the feet for plantar hyperhidrosis.

Figure 1:
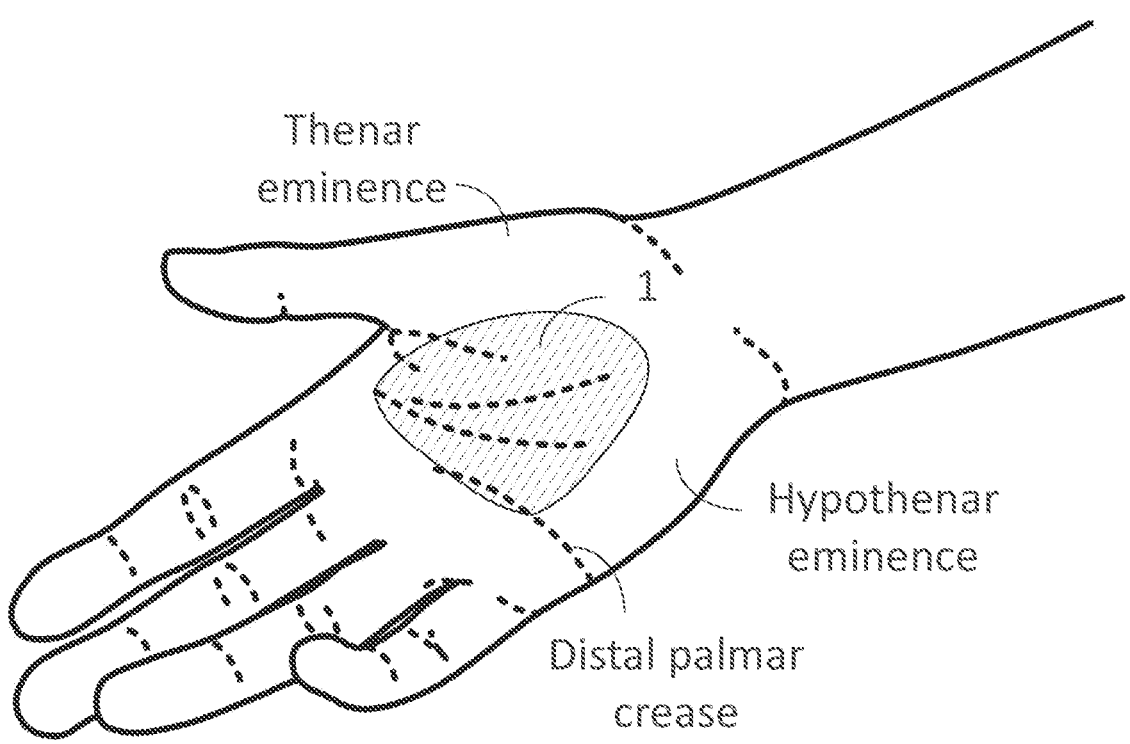
FIG. 1 illustrates a user's hand substantially indicating a concave portion of the palm.

Delivery of electrical or other energy to the treatment site can be inhibited if there is poor contact between any portion of the electrode and the treatment site. For example for the hand, one area of the hand that is particularly difficult to promote contact (or a snug or tight fit) on is the concave portion of the palm. As illustrated in FIG. 1, this portion 1 of the palm of a hand is believed to be approximately delineated by the distal palmar crease, thenar eminence and hypothenar eminence. Due to the concave nature of this portion 1 of the palm, even in a "flat hand" position, a typical hand-worn garment may naturally "stretch over" this portion 1 of the palm without promoting contact between the electrode(s) and this portion 1 of the palm. In partially closed or closed hand positions, material from the garment may bunch or wrinkle in the area positioned over this concave portion or in other positions, thereby further lessening fit. Material of the garment may additionally bunch or wrinkle in other areas, for example in the area positioned over the distal palmar crease and bases of the fingers. Thus, there remains a considerable need for hand-worn garments that promote contact with or fit snugly or tightly in at least a portion of the palmar side of the hand (including or excluding digits) in the flat hand position, relaxed hand position, closed hand position and/or other hand positions. Similarly, a typical sock may not provide sufficient contact between electrode(s) and the arch of a user's foot sole.

Additionally, existing approaches do not always provide an adequate mechanism for avoiding delivery of electrical current or other types of energy to body parts that do not require therapy, for example the arms, wrists, knuckles and nailbeds in the case of management of hand sweat, or treatment of palmar hyperhidrosis, or for example the ankles, shins and nailbeds in the case of management of feet sweat or treatment of plantar hyperhidrosis.

Embodiments of the present technology enable delivery of electrical or other energy to select regions of a user's skin, for example to manage hidrosis, treat hyperhidrosis or alleviate other problems or conditions. In some embodiments, a wearable device includes an outer assembly, an inner assembly with electrodes, a power source, and a controller configured to deliver energy to the electrodes. In operation, the inner assembly is placed in contact with the treatment site (e.g., a user's skin) to deliver electrical current to the treatment site.

As noted previously, delivery of electrical or other energy to the treatment site can be inhibited if there is poor contact between any portion of the electrode and the treatment site. In some embodiments, to promote contact between the inner assembly and the treatment site (e.g., a user's palm), an adapted form-fitting outer assembly may be used, for example in the form of an adapted garment. For example, an unadapted (form-fitting) outer assembly may be able to promote contact on body parts that do not have concave contours, but may not be able to promote contact if there is a concave portion to the contour of the body part. In some embodiments, a support structure, filler, or other such components can be used to promote contact between the inner assembly and the treatment site. Such outer assemblies and their support structures, fillers, and other similar components are shown and described below with respect to FIGS. 4-13.

Alternatively or additionally, a pump may be used in conjunction with a substantially air-tight outer assembly to promote contact between the inner assembly and the treatment site (e.g., a user's hand). Such a pump may enable a user to apply suction to draw the inner assembly into contact with the treatment site. Such suction-based approaches can perform better than adhesives, which may loosen in the presence of, for example moisture (e.g., sweat), small solids (e.g., dead skin cells), or heat. Still, adhesives may be used in combination with any of the embodiments disclosed herein. Examples of outer assemblies incorporating a pump are described below with respect to FIGS. 14-16.

Another shortcoming of conventional iontophoresis devices is the uneven or otherwise undesirable distribution of current across the treatment site. For example, electrodes may be subject to "edge effects," in which current density is more concentrated around the edges of the electrodes than in central or other non-edge portions. Additionally, current may be concentrated more along one edge than another (e.g., along a portion nearest to an electrode of the opposite polarity). As a result, a glove-like device having a distally positioned electrode and a proximally positioned electrode may result in undesirable concentration of current along the distalmost portion of the proximally positioned electrode and along the proximalmost portion of the distally positioned electrode. This can reduce effectiveness of the iontophoresis treatment, as less current reaches other portions of the treatment site. Alternatively, this may require increased total current to achieve the desired effectiveness, which introduces increased risks of harm or discomfort to the user. Accordingly, it can be beneficial for electrode configurations to provide for improved current distribution across the treatment site. Such electrode configurations can be carried by, integrated with, or otherwise coupled to the inner assembly. Embodiments of the present technology include electrode configurations to optimize current density distribution into the skin, for example by varying the thickness, distribution, and extent of conductive and resistive layers for electrodes of opposing polarity.

Examples of inner assemblies carrying one or more electrodes and various electrode configurations are described below with respect to FIGS. 17A-20B.

As described in more detail below, embodiments of the present technology include devices intended to target the hand, for example glove-like devices. Additionally, embodiments of the present technology can be configured to deliver electrical energy to other body parts, for example the skin of a user's foot or under-arm region, as shown and described below with respect to FIGS. 21-23B.

In addition to wearable devices, embodiments of the present technology are directed to non-wearable devices that can deliver electrical current to a user's hand or other body parts, for example a device that can be grasped by a user or otherwise positioned against a treatment site on a user's skin. Examples of such non-wearable devices are shown and described below with respect to FIGS. 24A-25.

The devices, systems and methods disclosed herein may be used in the management of hidrosis, treatment of hyperhidrosis, Raynaud's disease, arthritis, carpal tunnel syndrome, pain and other problems or medical conditions. These devices, systems and methods may be used to ensure delivery of the electrical current, other energy or medications to pre-determined areas of the body. In some embodiments, the devices, systems or methods disclosed herein may be used in other situations in which it is desirable to have a glove, mitten, gauntlet, sock, cuff or other garment fit snugly or tightly to the user's skin or against another material (such as an inner assembly), even if no energy delivered. For example, snug or tight fit may make a hand-worn garment more comfortable to wear, may be more aesthetically appealing, may improve performance in daily or athletic activities e.g., by enabling a better grip or protection of the hand or a portion of the palm or hand against mechanical or other impact or friction. Also, for example, snugly or tightly fitting foot-worn, underarm-worn or facial garments may be desirable for a variety of applications.

III. EXAMPLE WEARABLE DEVICES FOR DELIVERING ELECTRICAL CURRENT TO A USER'S SKIN, SUCH AS THE PALMAR SKIN

Figure 2:
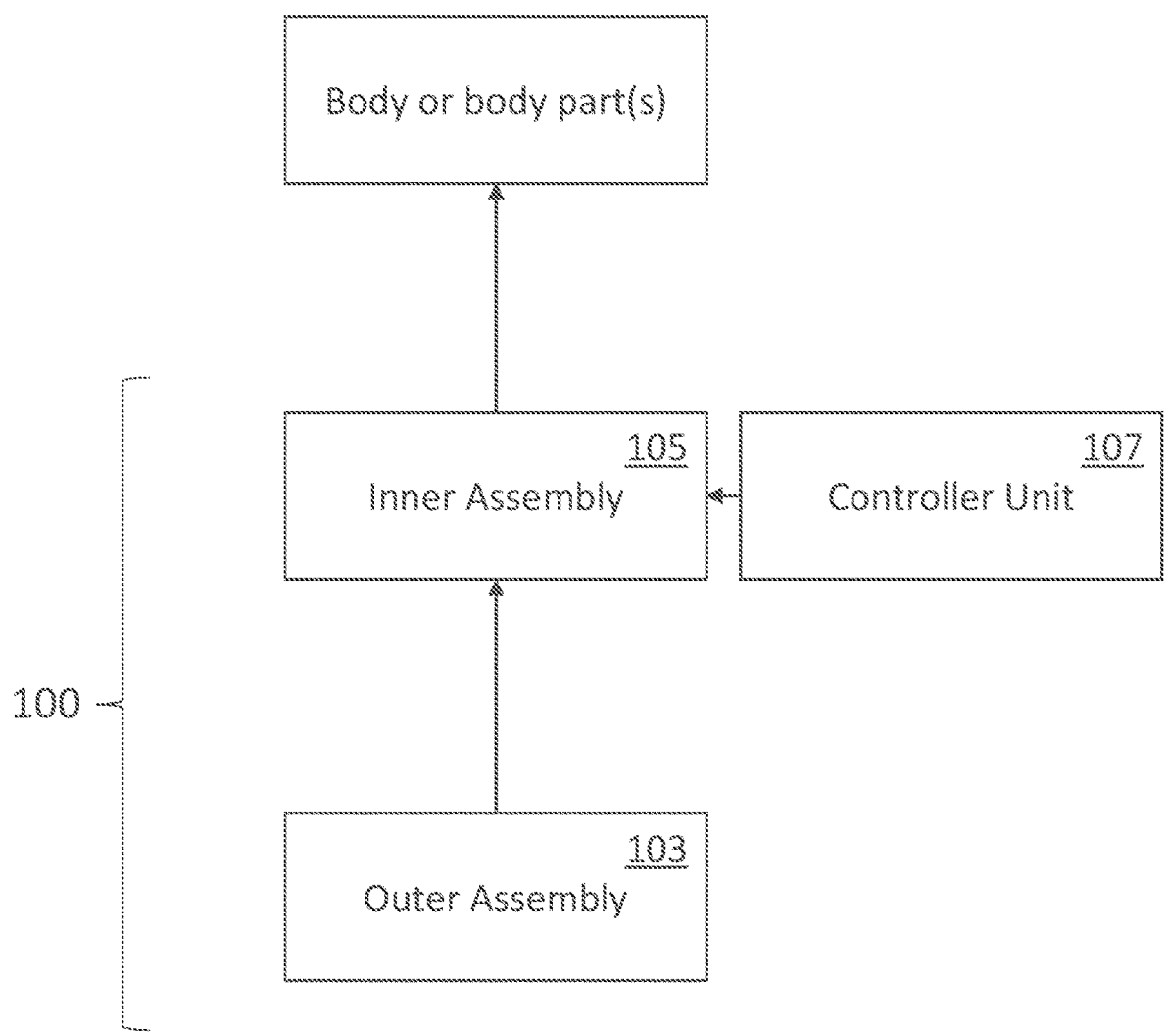
FIG. 2 illustrates a schematic overview of some embodiments of the present technology.

As shown schematically in FIG. 2, the present technology includes a wearable device 100 for delivering electrical current or other type of energy to a user's skin. The wearable device 100 includes an outer assembly 103 and an inner assembly 105 that may or may not be removably inserted into or connected to the outer assembly 103. The inner assembly 105 (and/or the outer assembly 103) can include or carry one or more electrodes configured to deliver electrical current to a user's skin while wearing the device 100. A controller unit 107 (which can include a power source and a controller) can be permanently or removably attached to the outer assembly 103 and electrically coupled to one or more electrodes carried by the inner assembly 105 (or outer assembly 103). For example, one or more connectors 109 can be disposed on the outer assembly 103 and configured be electrically coupled to the controller unit 107. Additionally, one or more connectors 111 can be disposed on the inner assembly 105 and electrically coupled to one or more electrodes carried by the inner assembly 105. When the inner assembly 105 is disposed within the outer assembly 107, a conductive path is established between electrodes carried by the inner assembly 105 and the controller unit 107, via the connectors 109, 111. This interconnection enables the controller unit 107 to deliver current to the electrodes carried by the inner assembly 105.

In some embodiments, the outer assembly 103 and/or the inner assembly 105 can be shaped to correspond to the target body part, for example being glove-shaped to conform to a user's hand, sock-shaped to conform to a user's foot, etc. In some embodiments, the inner assembly 105 and outer assembly 103 can be combined into a single assembly or can be otherwise coupled together in a non-removable fashion.

Figure 3:
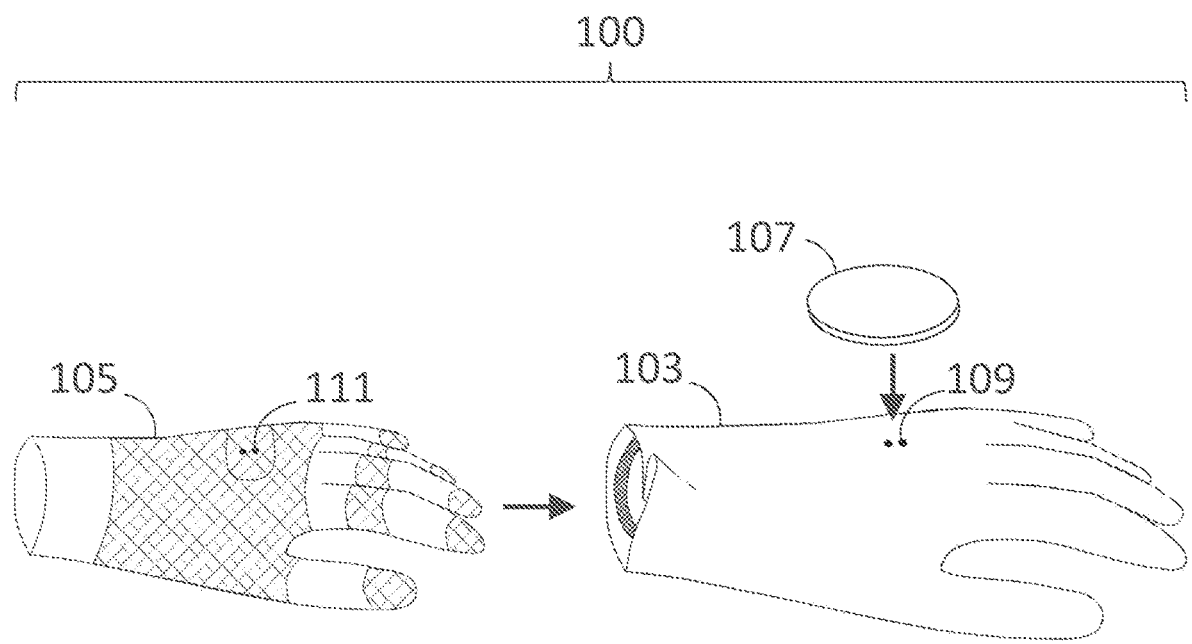
FIG. 3 illustrates components of a wearable device for delivering electrical current to a user's hand in accordance with embodiments of the present technology.

As shown in FIG. 3, in the case of a wearable device 100 configured for use over a user's hand, the outer assembly 103 and the inner assembly 105 can each be substantially glove-shaped. The outer assembly 103 can be coupled to the controller unit 107, e.g., with the controller unit 107 removably (or non-removably) coupled to a backside of the outer assembly 103. The inner assembly 105 can carry one or more electrodes configured to contact the user's skin when the inner assembly 105 is donned over the user's hand. When the outer assembly 103 is placed over the inner assembly 105, internal electrical contacts (not shown) provide an electrical path between the controller unit 107 and the electrode(s) carried by the inner assembly 105, such that current can be delivered from the controller unit 107 to the electrode(s), thereby delivering electrical current to the user's skin.

In various embodiments, the inner assembly 105 and the outer assembly 103 can be separated from one another, for example with the outer assembly 103 being completely removed while the inner assembly 105 remains in place over a user's skin. In some embodiments, the two assemblies can be permanently coupled together or even integrally formed. Moreover, any two or more components and/or subsystems of the device 100 may be integrated into one another.

In order to more effectively treat certain conditions (e.g., palmar hyperhidrosis), it can be beneficial to promote contact between the inner assembly 105 and the treatment site (e.g., the user's palm). As described in more detail below, in some embodiments such contact can be promoted via one or more support or filler components, which can be coupled to the inner assembly 105 and/or the outer assembly 103. Such support or filler components are described below with respect to FIGS. 4-13. In some embodiments, a suction source can be used to promote contact between the inner assembly 105 and the treatment site (e.g., the user's palm), as described in more detail below with respect to FIGS. 14-16.

A. Outer Assembly with Palm Support

In some embodiments of the technology, components are included to promote contact between the inner assembly 105 and the user's skin. A form-fitting outer assembly 103 may be able to promote contact on body parts that do not have concave contours, such as around the fingers, arm, leg or other body parts with concave contours. A stretchable material may be used for the outer assembly 103 to create radial forces onto the body part the outer assembly 103 is applied to, or onto the inner assembly 105. However, such an outer assembly 103 without further adaptations may not be able to promote contact if there is a concave portion to the contour of the body part. An adapted form-fitting outer assembly 103 may be used to promote contact between the inner assembly 105 and the treatment site, for example in the form of an adapted form-fitting garment. In some embodiments, a support structure, filler, or other such components can be used to promote contact between the inner assembly 105 and the treatment site (e.g., the user's palm).

For example, focusing here on the palm of the hand, one area of the hand that is particularly difficult to ensure a snug or tight fit on, or promote contact with, is the concave portion of the palm. As illustrated in FIG. 1, this portion 1 of the palm of a hand is approximately delineated by the distal palmar crease, thenar eminence, and hypothenar eminence. Due to the concave nature of this portion 1 of the palm even in a "flat hand" position, a typical hand-worn garment such as a glove, mitten or gauntlet may naturally "stretch over" this portion 1 of the palm without promoting contact between the inner assembly 105 and this portion 1 of the palm, while good contact between the inner assembly and the skin may be achieved elsewhere on the hand. In half-closed or closed hand positions, garment material may bunch or wrinkle in the area positioned over this concave portion or in other positions, thereby further lessening fit. Garment material of outer assembly 103 or inner assembly 105 may additionally bunch or wrinkle in other areas, for example in the area positioned over the distal palmar crease and bases of the fingers. Thus, there remains a considerable need for hand-worn devices that fit snugly or tightly in at least a portion of the palmar side of the hand (including or excluding digits) in the flat hand position, relaxed hand position, closed hand position and/or other hand positions. Embodiments of the present technology relate to such form-fitting hand-worn devices or other garments.

In some embodiments, outer assembly 103 can comprise a glove, mitten, or other shape configured to fit over a user's hand. For example, the outer assembly 103 can be hand-shaped, including a palm portion and a plurality of finger extensions. In alternative embodiments, the outer assembly 103 can be foot-shaped, or can take the form of a pad that covers a user's under-arm region, or a pad configured to be applied over a user's forehead, or can be configured to be applied over yet other body parts.

In some embodiments, the outer assembly 103 is made out of substantially electrically non-conductive materials, or materials that are substantially electrically non-conductive except for prongs for creating an electrical connection between the controller unit 107 and one or multiple electrodes included on or carried by inner assembly 105. The electrical connection can be permanent or non-permanent, for example with a connector 109 that can be opened and closed. In some embodiments, one or more electrodes or select layers of the electrodes may be carried by the outer assembly 103.

Although many examples disclosed herein relate to hand-worn garments such as gloves, embodiments of the contact-promoting components described herein (e.g., palm filler or palm support) can be applied to other body parts, for example a sock-like garment having one or more contact-promoting components integrated therein (e.g., filler or support structure), a mask-like garment having one or more contact-promoting components integrated therein (e.g., filler or support structure), etc.

The modalities of improving fit disclosed herein may be applicable even if there is an extra material (including but not limited to an inner assembly, insert, wiring, second garment, or a substantially waterproof layer) in between the outer assembly or parts of the outer assembly and the user's skin. In those cases the fit may not result in contact between at least part of the outer assembly itself and at least part of the user's skin, but between at least part of the extra material and at least part of the user's skin.

Palm Support Components

FIGS. 4A-7 illustrate various embodiments of a palm support 200. To improve fit of a hand-worn device 100 or garment, and/or to promote contact of an inner assembly 105 to skin in at least part of the concave portion of the palm (for example the area shown as area 1 in FIG. 1), a palm support 200 may be used. This palm support 200 may be added to, reversibly or irreversibly attached to, or incorporated in the device 100 to cover at least part of the region between the distal palmar crease, thenar eminence and hypothenar eminence of the user's hand. In some embodiments, the palm support 200 can be made out of a material that is substantially more rigid than some or all surrounding parts of the device or garment. In some embodiments, the palm support 200 can be secured in place via one or more fasteners 240.

This palm support 200 can have a range of different shapes. For example, the palm support 200 may be a three-dimensional structure of which part of the surface is shaped to be substantially in contact with the user's palm when the hand is in a relaxed, open, closed or other position. The palm support 200 may also be a three-dimensional structure with one dimension of the structure (referred to as the thickness of the element) being substantially smaller than the other dimensions. This is the dimension that, when worn on a hand, would be approximately perpendicular to the skin. The palm support 200 may also have one or more curved surfaces. The thickness of the palm support 200 may be constant or vary across the component. As a consequence, opposing surfaces may have different curvatures.

Figure 4A:
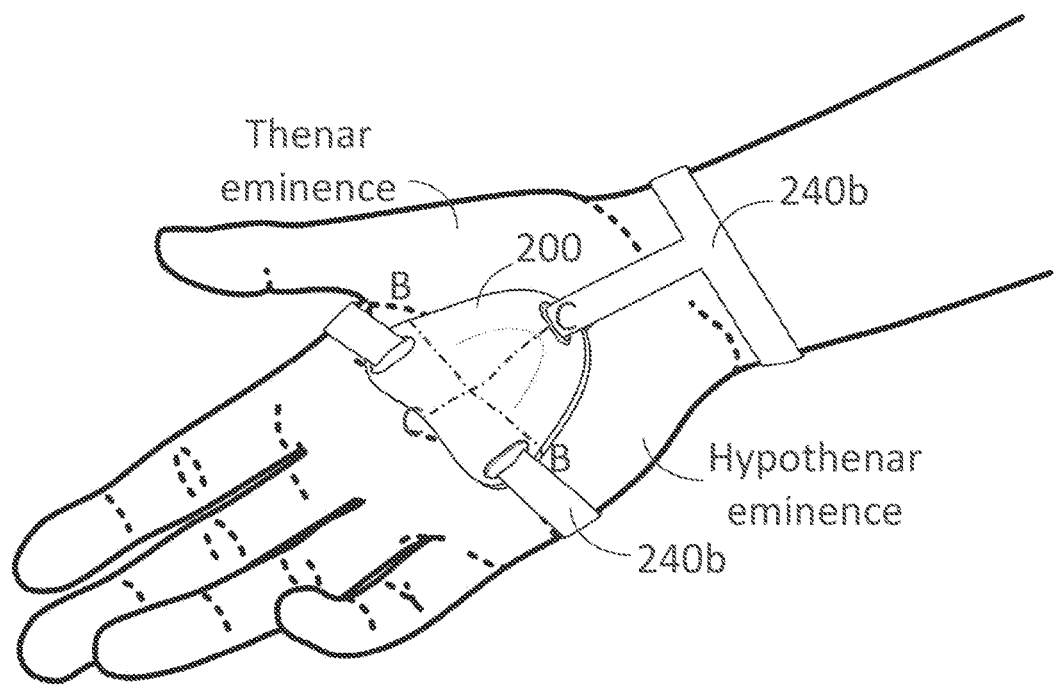
FIG. 4A illustrates a palm support and fastener coupled to a user's hand in accordance with embodiments of the present technology.
Figure 4B:
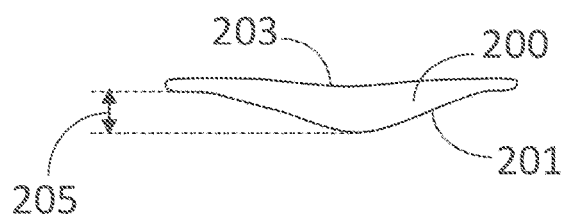
FIG. 4B illustrates a cross-section of the palm support shown in FIG. 4A taken along line B-B in FIG. 4A.
Figure 4C:
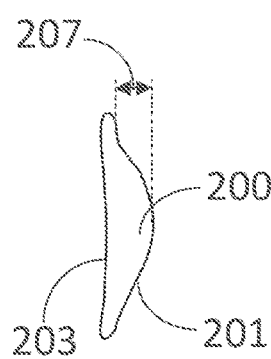
FIG. 4C illustrates a cross-section of the palm support shown in FIG. 4A taken along line C-C in FIG. 4A.

As illustrated in FIGS. 4A-C, a surface 201 of the palm support 200 closest to the user's skin may be curved in the axial, mediolateral and/or sagittal directions to ensure contact between the palm support 200, inner assembly 105, outer assembly 103, and/or (other) garment and at least a portion of the palmar side of the hand.

According to one embodiment, as illustrated in FIG. 4B (which represents a cross-section along line B-B indicated in FIG. 4A) the palm support 200 includes at least one part with a two-dimensional convex surface 201 that, when positioned correctly on a user's hand, substantially conforms to at least part of the concave portion of the palmar side of the hand. The curved surface 201 has a depth 205 of about 2 cm or less, depending on the approximate hand geometry to match and on what position the garment is ideal in (e.g., flat vs. relaxed hand position). As illustrated in FIG. 4C (which represents a cross-section along line C-C indicated in FIG. 4A), the curved surface 201 has a depth 207 of about 1 cm or less, about 2 cm or less, about 3 cm or less, or a different range depending on the hand geometry to match and on what position the garment is ideal in (e.g., flat vs. relaxed hand position, position in which the pinkie substantially touches the thumb). The opposing surface 203 may be flat, convex or concave, or otherwise contoured as needed.

Figure 4D:
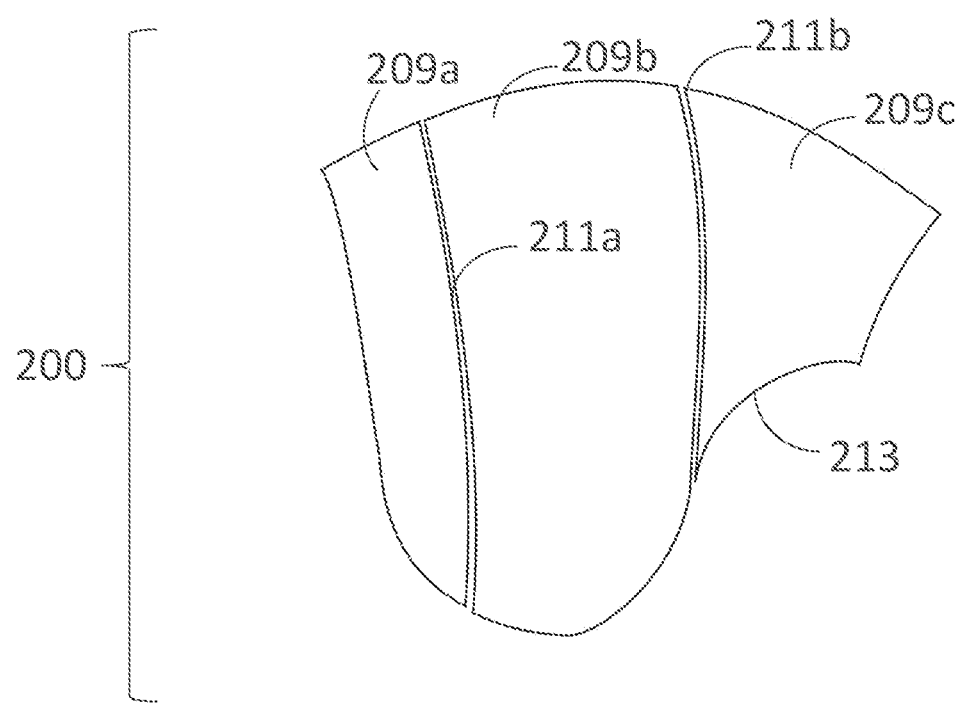
FIG. 4D illustrates a palm support including segments in accordance with embodiments of the present technology.

The palm support 200 may also be made out of a bent wire or set of wires or other means as long as the outer contours of the structure delineate a desirable shape to ensure contact between the hand-worn garment or palm support, inner assembly, outer assembly, or (other) garment and at least part of the concave portion of the palm. The palm support 200 may also be made out of multiple segments 209 that together form the palm support. Gaps 211 between the segments 209 may allow movement in the direction perpendicular to the gaps 211. For example, as illustrated in FIG. 4D, the palm support 200 may be made out of segments 209*a-c* that are elongated in the axial direction when worn on a hand, with gaps 211*a-b* between segments 209*a-c* allowing the user to bring their thumb towards their pinky finger (opposition movement). Alternatively, the palm support 200 may be made out of segments 209 that are elongated in the mediolateral direction allowing the user to open and close their hand more easily. The gaps 211 may be placed where no material protrudes from the garment, or may have less material or material of different stiffness than other areas of the palm support 200.

Figure 4E:
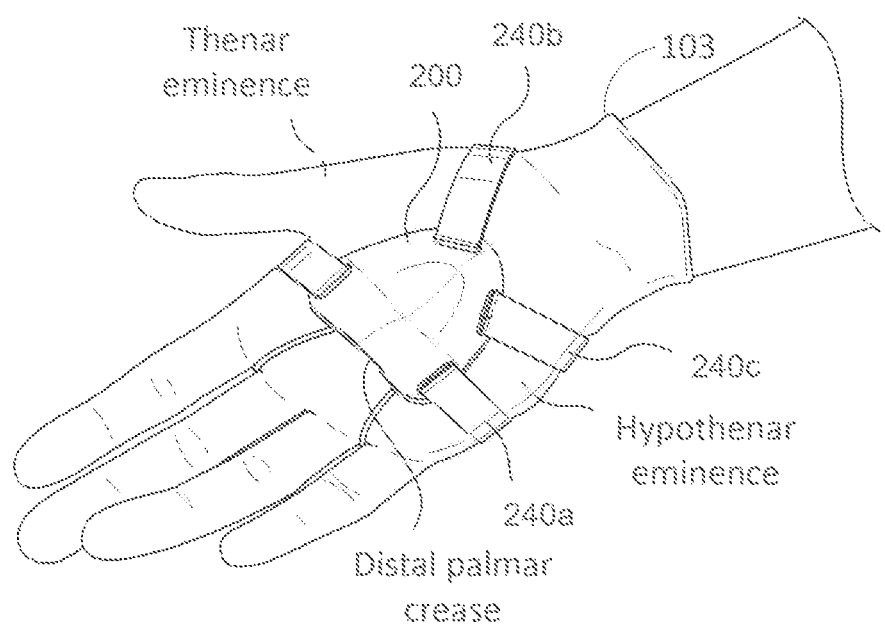
FIG. 4E illustrates a palm support and fastener coupled to a user's hand in accordance with embodiments of the present technology.

FIG. 4E illustrates another embodiment of a palm support 200 secured in place over the palmar portion of the outer assembly 103. As shown, the palm support 200 is secured in place via a plurality of fasteners 240*a-c* which can be secured on a backside of the outer assembly 103 using, for example, hook-and-loop fasteners, clips, snaps, buckles, etc. In some embodiments, the palm support 200 may also have a shape 213 configured to fit around the thenar eminence.

As previously mentioned, the palm support 200 may cover at least part of the region between the distal palmar crease, thenar eminence and hypothenar eminence, but the palm support 200 may also cover other parts of the palm, hand or wrist. This may help avoid bunching of garment material (e.g., from inner assembly 105 or outer assembly 103) in those other parts of the palm or hand. If the palm support 200 is used to hold an extra material (e.g., inner assembly, insert or second garment) against the skin, this extra material may bunch in the zones of the palm support that through construction are further separated from the body. The palm support 200 may be designed in a way to localize bunching of the extra material to one or multiple pre-determined zones (e.g., where bunching is less of an issue or even desirable) and minimize bunching elsewhere.

Figure 5:
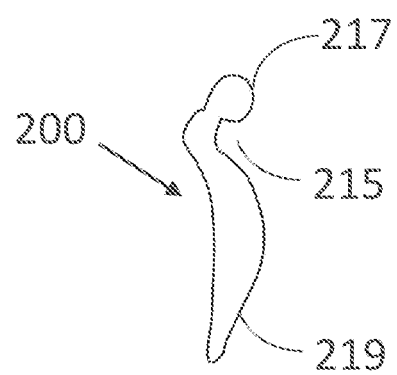
FIG. 5 illustrates a sagittal cross-section of a palm support in accordance with embodiments of the present technology.

According to one embodiment, as illustrated in FIG. 5, which represents a sagittal cross-section of a palm support 200, the palm support 200 may include a zone 215 that curves away from the hand to allow bunching of material in this zone. This zone 215 may be placed over the distal palmar crease so that the extension 217 touches the skin distal to the distal palmar crease, while the surface 219 touches the skin proximal to the distal palmar crease.

Figure 6:
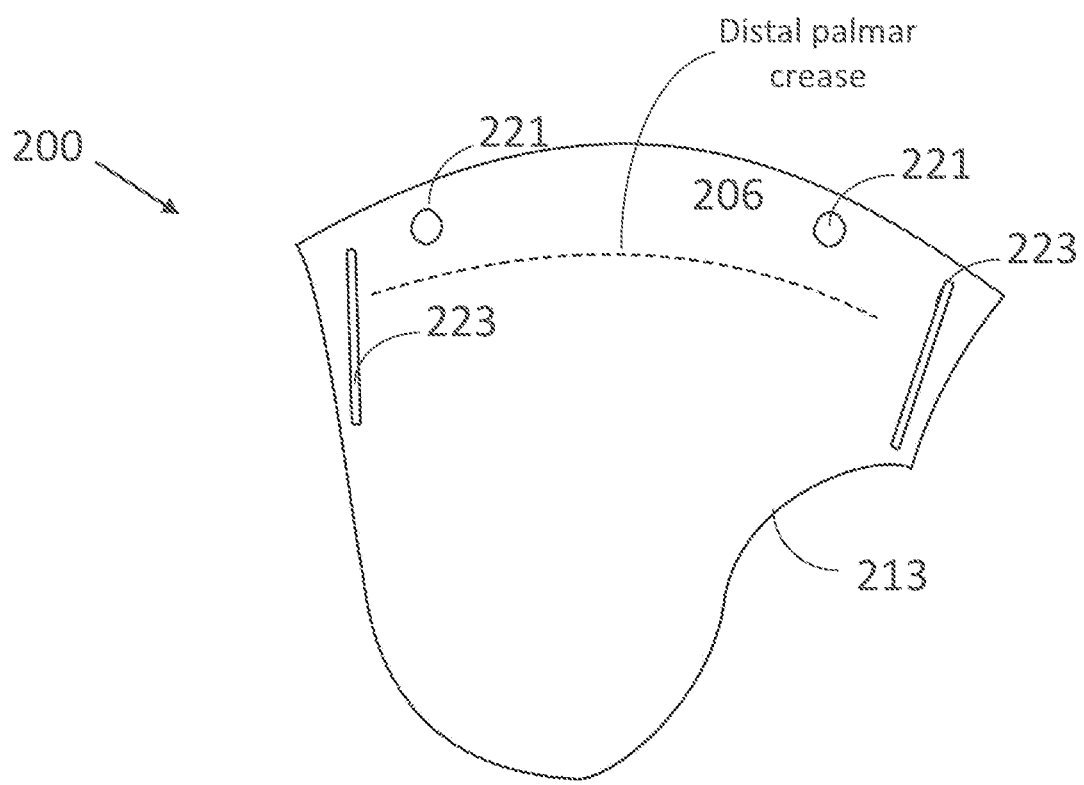
FIG. 6 illustrates a palm support in accordance with embodiments of the present technology.

According to one embodiment, as illustrated in FIG. 6, the palm support 200 extends distal to the distal palmar crease, thereby avoiding bunching of material in this zone. The palm support 200 may also have a shape 213 to fit around the thenar eminence.

The palm support 200 may be constructed out of multiple relatively rigid parts that are connected with a hinge, more flexible zone or other means to allow bending or movement of the various parts with respect to each other. According to one embodiment, such a hinge or more flexible zone is configured to be substantially aligned with the distal palmar crease to improve hand motion while wearing the hand-worn garment. According to one embodiment, such a hinge or more flexible zone is configured to be substantially aligned with the thenar crease to improve hand motion while wearing the hand-worn garment.

The palm support 200 may contain one or more openings 221, 223 or attachment structures to which straps, cords or other attachment mechanisms may be fixed, reversibly or irreversibly coupled or otherwise connected. These openings or attachment structures may be placed along the outer contour of the palm support 200, for example on the lateral sides or proximally.

Figure 7:
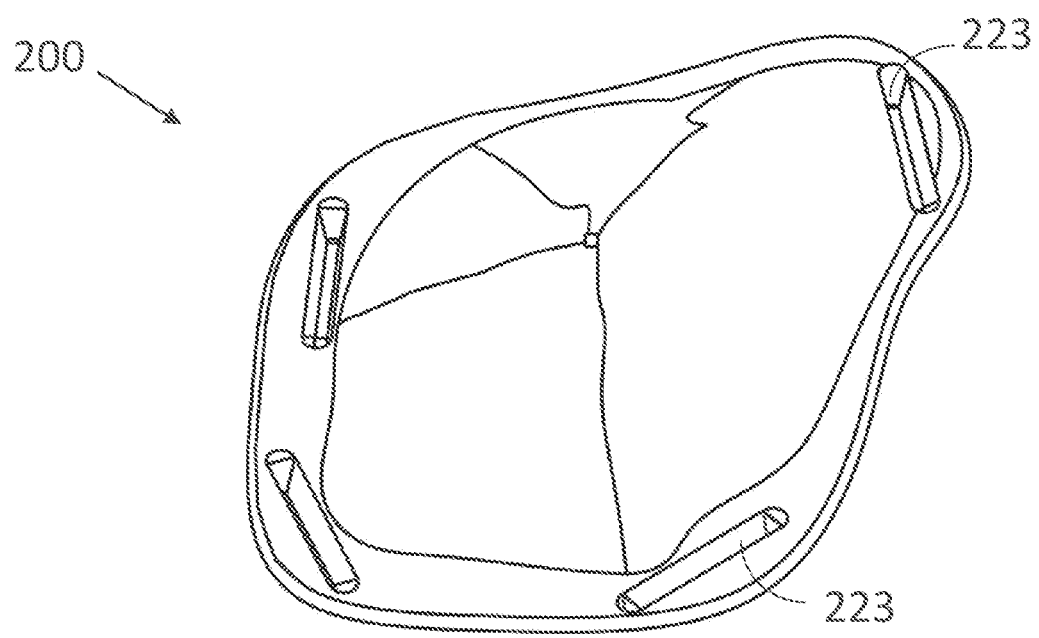
FIG. 7 illustrates another embodiment of a palm support in accordance with embodiments of the present technology.
Figure 8:
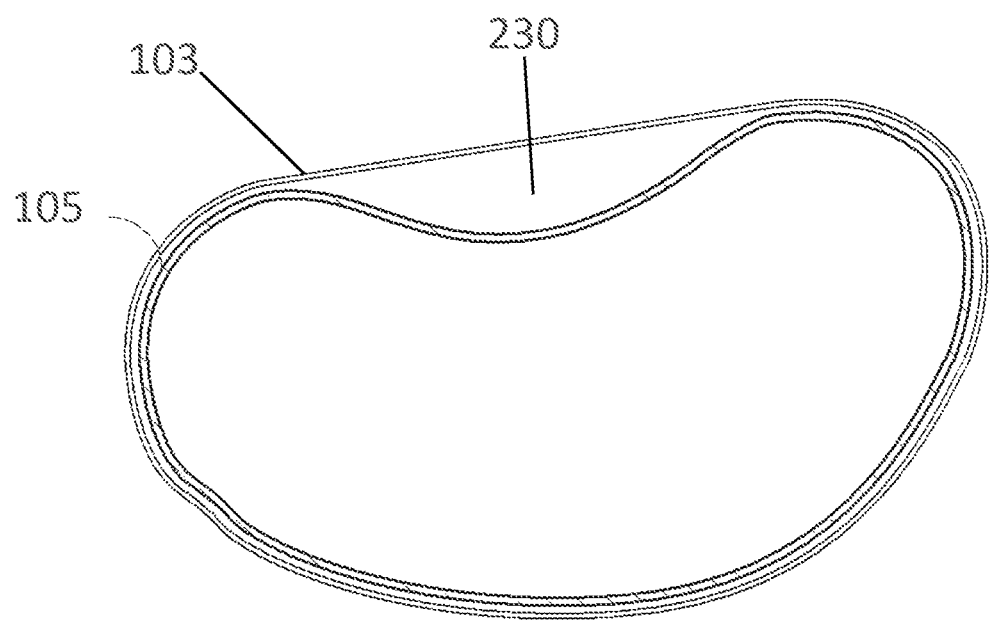
FIG. 8 illustrates a sagittal cross-section of an outer assembly with a palm filler component in accordance with embodiments of the present technology.

According to one embodiment, as illustrated in FIG. 7, the palm support 200 includes a sheet-like structure that has been formed into a substantially concave three-dimensional shape. When in use, the convex side of this palm support 200 faces the palm of the user's hand. The concave shape of this palm support has a relative peak of between 1-3 mm, between 3-5 mm, between 5-10 mm, between 10-15 mm, >15 mm to substantially align with the most concave central portion of the palm when correctly positioned on a user's hand. A part of the contour of this palm support 200 may be curved to be substantially parallel with the thenar crease when correctly positioned on a user's hand. A part of the contour of this palm support may be curved to be substantially parallel with the palmar digital crease when in use. This palm support 200 may contain a plurality of openings 223 along the contour of the palm support 200. The palm support 200 may be made out of a substantially inflexible material, potentially with zones of increased flexibility to allow for preferential bending substantially aligned with one or multiple palmar creases when in use, for example through higher surface curvature and/or thinner material in these areas. When the palm support 200 is reversibly or irreversibly attached to a garment, or incorporated into the garment, and the garment is worn over an inner assembly (that may contain electrodes), the above-mentioned features are believed to help provide improved contact between the inner assembly (and potential electrodes) and the user's skin.

The palm support 200 may be provided in one or multiple sizes to fit different hand sizes. The different sizes may be scaled versions of one another, or may have some differences between them to better fit different hand sizes, for example in terms of positioning of openings 221, 223, thickness, relative peak height and other features.

(ii) Support Components on Other Body Parts

Support components on other body parts can have a range of different shapes and configurations. For example, the support structure may be a three-dimensional structure of which part of the surface is shaped to be substantially in contact with the user's skin of a body part when the body part is in a relaxed or other position. For example, to improve fit of a foot-worn garment, such as a sock or shoe, in at least part of the arch of the foot, a support component may be added to, reversibly or irreversibly attached to, or incorporated in the garment to cover at least part of the arch of the foot, with this support component being made out of a material that is substantially more rigid than some or all surrounding parts of the garment. Similarly a support component may be added to, reversibly or irreversibly attached to, or incorporated in the garment to cover at least part of a user's under-arm.

(iii) Filler Components

To further promote contact between the inner assembly 105 and the user's skin, and/or improve fit of an outer assembly 103 or garment in, for example, a concave portion of a body part, extra material may be added to, reversibly or irreversibly attached to, or incorporated in the outer assembly 103 in an area that is meant to cover at least part of the concave portion of the body part. Alternatively or additionally, this extra material may be added to, reversibly or irreversibly attached to, or incorporated in the palm support 200, for example on the side facing the user's skin. Alternatively or additionally, this extra material may be added to, reversibly or irreversibly attached to, or incorporated in the inner assembly 105 in an area that is meant to cover at least part of the concave portion of the body part. Alternatively or additionally, this extra material may be added as an additional layer in the area that is configured to cover at least part of the concave portion of the body part.

In some embodiments, the garment may be thickened in the area that, when positioned correctly on a user's skin, covers at least part of the concave portion of the body part. In some embodiments, as illustrated the cross-sectional view of FIG. 8, a palm filler 230 consisting of cushioning material may be incorporated into the outer assembly 103 such that the cushioning material is configured to engage at least part of the concave portion of the hand. Such a palm filler 230 may also be added to, reversibly or irreversibly attached to, or incorporated into a palm support. An additional material, such as an inner assembly 105, may be included between the cushioning material of the filler 230 and the hand.

Figure 21:
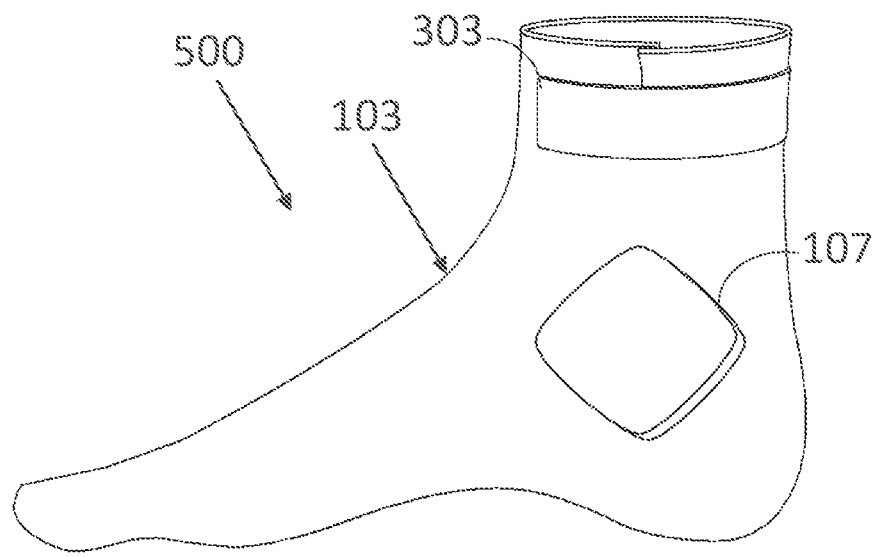
FIG. 21 illustrates a wearable device for delivering electrical current to a user's foot, including filler material, in accordance with embodiments of the present technology.

Filler components may also be used in embodiments adapted to other body parts or regions, for example, the hand, foot, under-arm region, face, forehead, region around or under the eyes, crotch, groin, amputated limb, or any other treatment site on a patient's body. According to another embodiment, as illustrated in FIG. 21, a filler component can be used under the arch of a user's foot and/or in the region where the proximal phalanges of the toes connect to the metatarsal bones on the dorsal side of the foot. For example, referring to FIGS. 23A-B, a filler component may be added under outer assembly 103 or between outer assembly 103 and the user's under-arm region.

(iv) Support Fasteners

To further promote contact between the inner assembly 105 and the user's skin, and/or promote fit of an outer assembly or garment in, for example, a concave portion of a body part, a support component and/or filler component may be held in place by means of a fastener that extends beyond the region where contact is desirable.

Figure 9A:
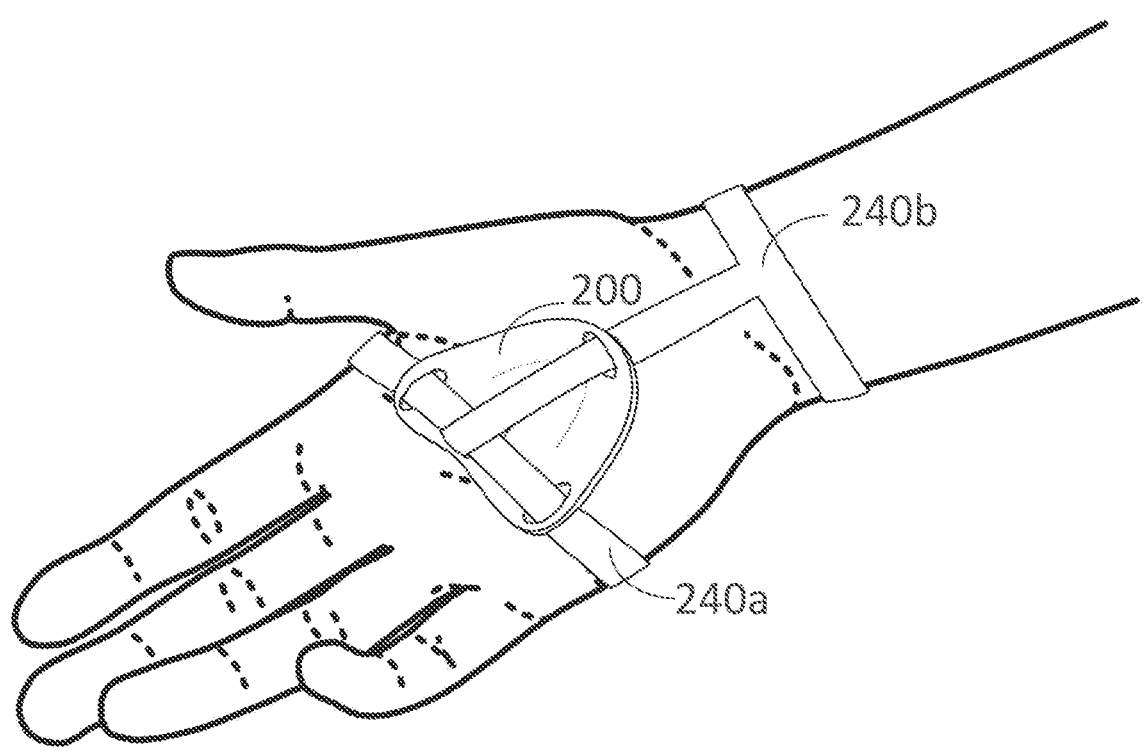
FIGS. 9A-9B illustrate palmar and dorsal views, respectively, of a palm support and fastener coupled to a user's hand in accordance with embodiments of the present technology.

According to one embodiment, as illustrated in FIG. 9A, a palm support fastener 240a which holds a palm support 200 in place, forms a closed loop around the hand. The material of this palm support fastener 240a may allow less than about 1 cm or between 1-5 cm or more of stretch across the circumference of the hand or may be more stretchable, as long as it forms a sufficiently tight loop around the hand once the material of the palm support fastener 240a is substantially stretched. This palm support fastener 240a is believed to provide a hoop strength around the hand that, along with the palm support 200 provides a substantially radial stress with respect to the closed loop of the palm support fastener 240a.

In some embodiments, an additional palm support fastener 240b that connects with a wrist band or other element that connects to the wrist may be present to further help position the palm support 200 in three dimensions (which is believed to require a minimum of three points to be positioned in space instead of just two in two dimensions). The palm support 200 resides in between the palm support fasteners 240 and the body, and is kept in contact with the body by the palm support fasteners 240 through the pressure of the palm support fasteners 240 onto the palm support 200, even if the hand position changes. Alternatively or additionally, a closed loop may be formed around the thumb, base of the thumb, one or multiple fingers, or another part of the hand around which a closed loop can be formed.

Figure 9B:
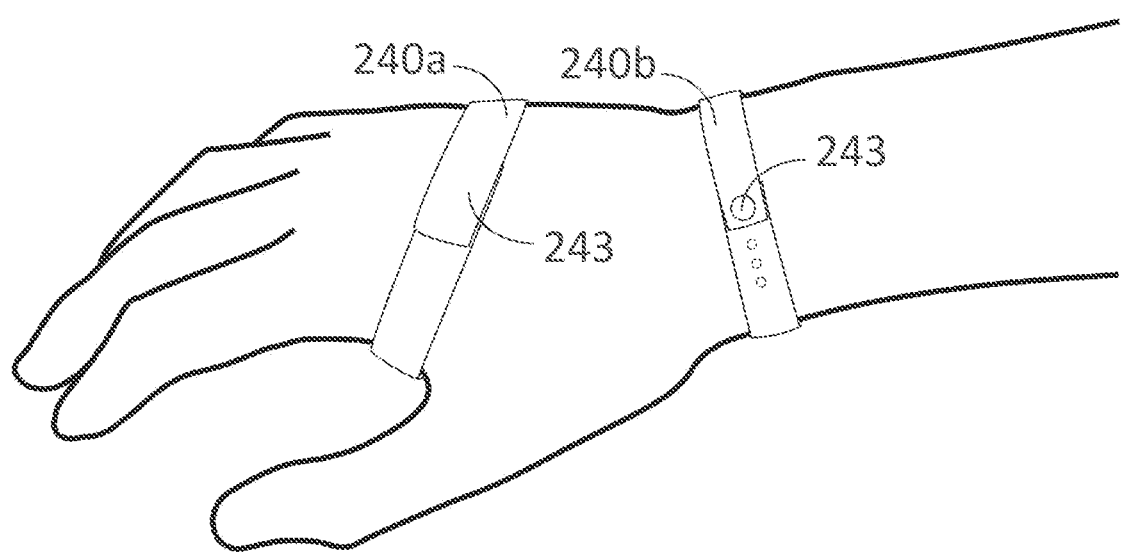
Figure 10:
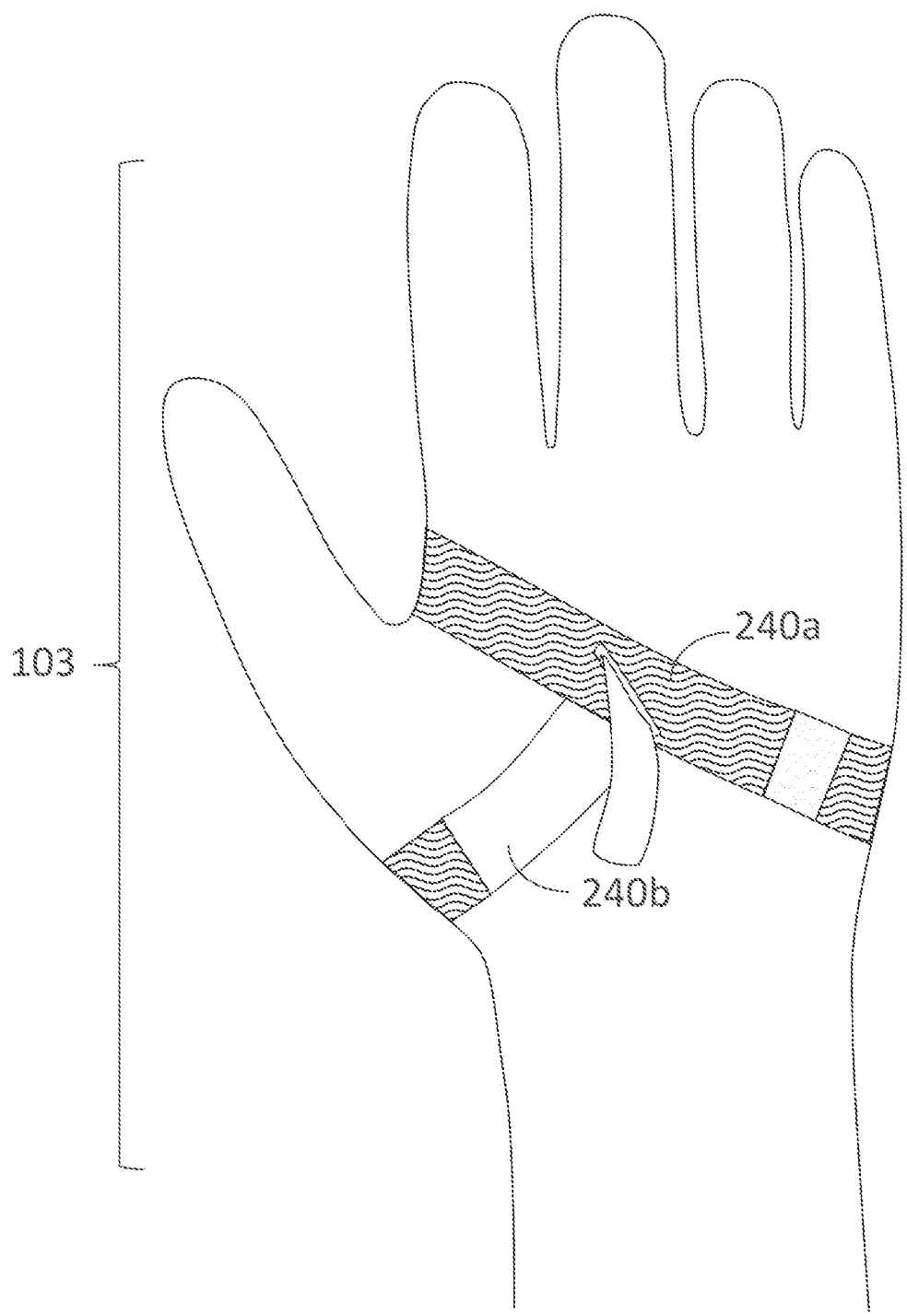
FIG. 10 illustrates a dorsal view of a glove with an integrated palm support fastener in accordance with embodiments of the present technology.

A palm support fastener 240 may be adjustable in size to be able to tailor tightness of the fit, to accommodate multiple hand sizes, to make donning and doffing easier or for any other reason where adjustable sizing may be helpful. For example, as illustrated in FIG. 9B for palm support fasteners 240a and 240b on the user's hand, this may be achieved by incorporating one or more hook-and-loop palm support fasteners 241, snap buttons 243, cinches, spring stop toggle cord lock or other means along the dorsal side of the hand or any other part of the fastener. As illustrated in FIG. 10, on an outer assembly 103, this may also be achieved with a different configuration of support fasteners 240a-b in the form of adjustment straps.

Figure 11:
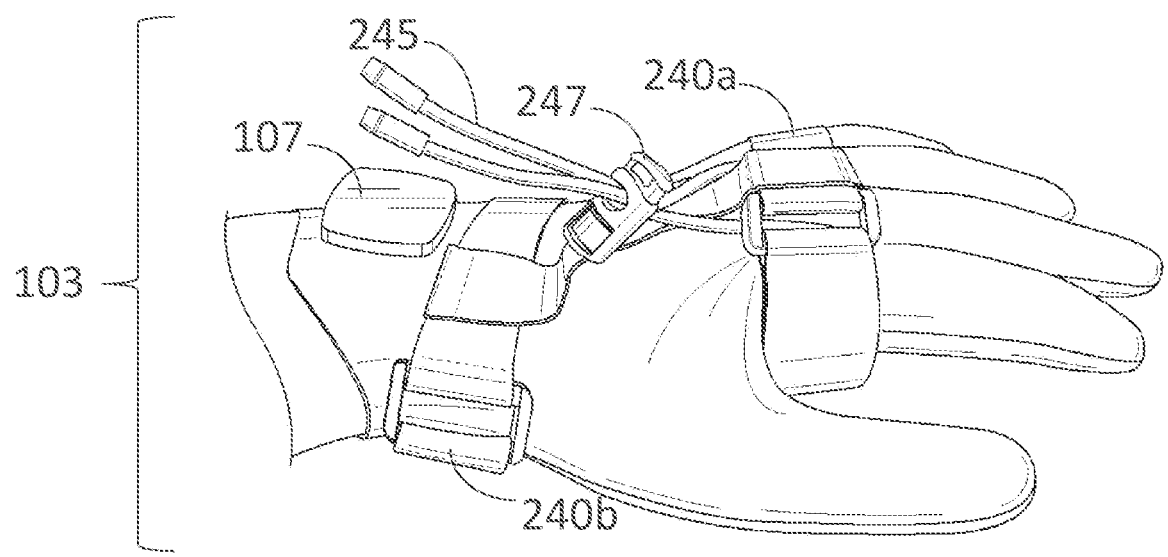
FIG. 11 illustrates another wearable device for delivering electrical current to a user's hand in accordance with embodiments of the present technology.
Figure 12:
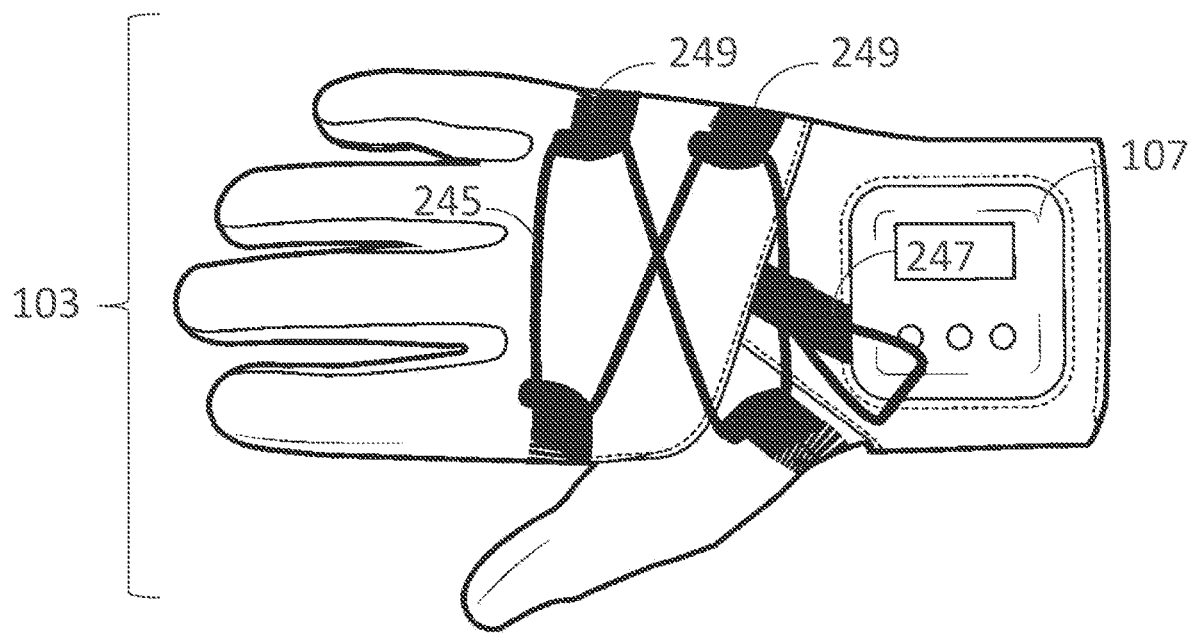
FIG. 12 illustrates another wearable device for delivering electrical current to a user's hand in accordance with embodiments of the present technology.

FIGS. 11 and 12 illustrate additional examples of a fastener 240 configured to secure a palm support 200 (not shown) with respect to an outer assembly 103. In the embodiment of FIG. 11, the fastener 240 includes a cord 245 that is coupled to fasteners 240a and 240b. The cord 245 is also coupled to a cord lock 247. In operation, the cord lock 247 can be depressed and the cord 245 can be pulled back, thereby positioning the palm support 200 (not shown) with respect to the hand. The fasteners 240a and 240b can also be tightened, thereby positioning the palm support with respect to the hand. To loosen the fasteners 240a and 240b, the cord lock 247 can be depressed to release the cord 245.

In the embodiment of FIG. 12, the cord 245 is looped through a plurality of grommets 249 (which may be connected to the palm support 200, not shown) disposed on opposing lateral sides in a shoe-lace fashion. When the cord lock 247 is depressed and the cord 245 is pulled back, the cord 245 exerts an inward force on the grommets 249 and pulls them closer toward one another, thereby tightening the outer assembly 103 with respect to the user's hand and positioning the palm support 200.

Figure 13A:
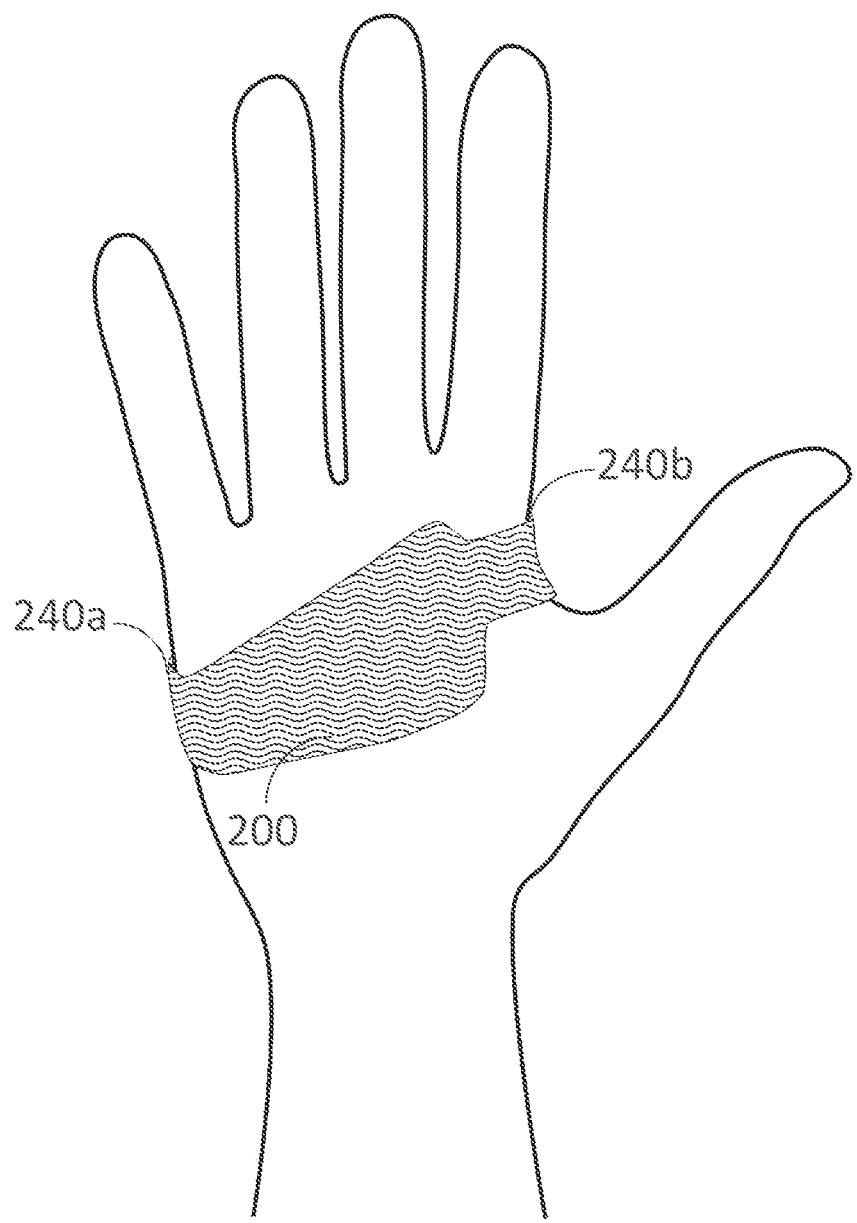
FIGS. 13A-13B illustrate palmar and dorsal views, respectively, of a palm support with an integrated fastener that extends to the back of the hand in accordance with embodiments of the present technology.
Figure 13B:
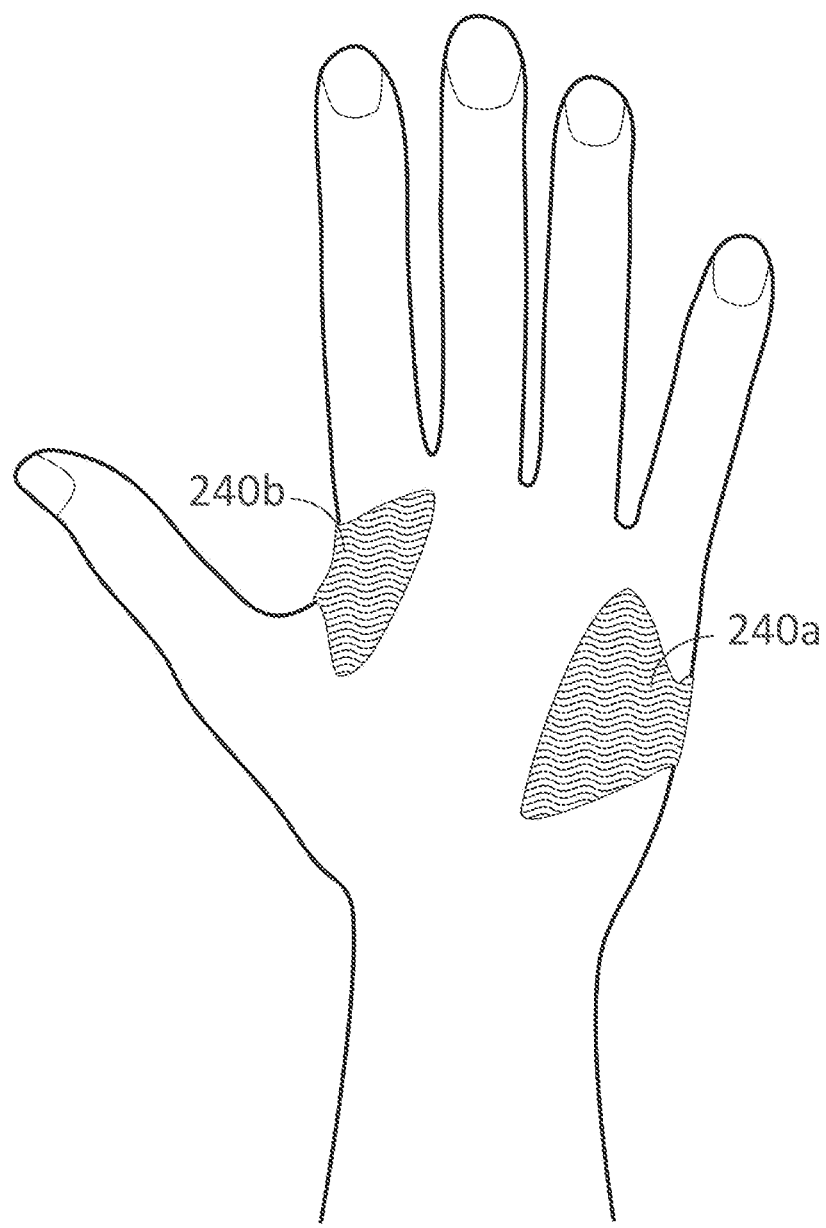

In some embodiments, as illustrated in FIGS. 13A-B, a palm support 200 or palm filler may have an integrated fastener 240 that anchors to the hand by extending to the back of the hand without forming a closed loop. For example a first fastener 240a extends away from the palmar region towards the radial side of the hand, and a second fastener 240b extends away from the palmar region and towards the ulnar side of the hand. The fasteners 240 can include an adhesive or other suitable material to secure the fasteners 240 in place against the skin of the user's hand. The palm support 200 may be made out of a substantially more rigid material than the majority of the hand-worn device and the shape of the palm support 200 may hook onto one or both sides of the hand. This may also be achieved with a fastener 240 that is not integrated with the palm support or palm filler, but is reversibly or irreversibly attached to the palm support or palm filler.

In some embodiments, the palm support fastener 240 may be held in place by extending to the webbing between two or more fingers without forming a closed loop. In this case, the palm support fastener may be made out of a more rigid material than the majority of the hand-worn garment (for example, similar in rigidity to the rigidity of the palm support) and the shape of the palm support fastener hooks onto one or multiple webbings.

In contrast to a wrist guard or splint, according to some embodiments, the palm support fastener 240 may not substantially alter the range of motion of the wrist because the more rigid elements do not extend down to the wrist.

In some embodiments, a palm support 200 or palm filler 230 on a hand extends into one or more finger protrusions of the garment. These finger protrusions may have the length of a digit or be shorter, for example the length of a finger phalanx, or shorter. The hoop force generated by the finger protrusion of the garment is believed to result in a radial force onto (a portion of) the palm support or palm filler that is contained inside the finger protrusion, thereby helping to keep the palm support or palm filler in place on the user's hand.

Support fasteners may also be used in embodiments adapted to other body parts or regions, for example, the hand, foot, under-arm region, face, forehead, region around or under the eyes, crotch, groin, amputated limb, or any other treatment site on a patient's body. For example, in the case of a foot, the closed loop could extend from the arch of the foot to the dorsal side of the foot.

(v) Materials

The components of the outer assembly 103) that do not form the support 200, the filler 230, or the support fastener 240, and the inner assembly 105 may be made out of any typical garment material, including but not limited to woven and non-woven materials, cotton, leather, spandex, polyester, nylon, latex, rubber, GORE-TEX, neoprene, silicone, wool, polyurethane, rayon, viscose, and blends or laminates thereof. The choice of material may influence the user's assessment of comfort, including but not limited to comfort related to temperature, humidity and pressure. For example, a material that substantially acts as a thermal insulator such as neoprene may be used for the outer assembly for improved comfort even if the inside of the outer assembly closest to the user's skin is wet. Note that also the fit of a garment may influence comfort: if moisture is contained between a garment and a surface of skin, radial compression of the garment onto the surface of skin may help create a fluidic layer that will help avoid sensation of wetness. The outer assembly and inner assembly may be manufactured using tools including knitting (e.g., 3D knitting) or sewing. Seams may be reinforced or made waterproof or airtight, or substantially waterproof or airtight, using seam tape, waterproof thread, seam seal or other means. A waterproof layer may also be added as a separate, integrated or partly integrated layer, e.g., a polyethylene, polyester, latex, rubber, GORE-TEX, neoprene, silicone, polyurethane layer or blends or laminates thereof.

The support 200 may be made out of materials that are more rigid than some or all surrounding parts of the garment, including but not limited to polyethylene, PET, PETG, polyurethane, ABS, silicone, rubber, ethylene-vinyl acetate, or any other relatively light-weight material that can substantially hold shape. The support 200 or part of the support 200 may also be made out of a material that can be formed into shape, including but not limited to lightweight thermoplastics or an inflatable structure. The support 200 may be covered or laminated with other softer materials, including but not limited to woven and non-woven materials, cotton, leather, spandex, polyester, nylon, latex, rubber, GORE-TEX, neoprene, silicone, wool, polyurethane, rayon, viscose, and blends or laminates thereof.

The filler 230 may be made out of materials that are deformable, including but not limited to woven and non-woven materials, cotton, leather, spandex, polyester, nylon, latex, rubber, GORE-TEX, neoprene, silicone, wool, polyurethane, rayon, viscose, ethylene-vinyl acetate, and blends or laminates thereof. One or more of these materials may be present as sheets, foams, sponge-like structures, fiber filling or other deformable structures. The filler 230 may also be a collection of pellets, sheets or other structures made out of more rigid materials including but not limited to polyethylene, polyurethane, ABS, silicone, rubber, ethylene-vinyl acetate, or any other relatively light-weight material that can substantially hold shape, and blends or laminates thereof, potentially held together by a pocket or other means, that together form a deformable structure.

A support fastener 240 that is part of a closed loop around the hand or part of the anatomy of a hand or other body part may be made out of materials that are flexible but have less stretch than the remainder of the garment, including but not limited to woven and non-woven materials, cotton, leather, spandex, polyester, nylon, latex, rubber, GORE-TEX, neoprene, silicone, wool, polyurethane, rayon, viscose, and blends or laminates thereof. Other materials may also be used as part of the support fastener 240. Alternatively a support fastener 240 may contain more stretch along at least part of its length. In such cases, the support fastener 240 is placed under tension once in use, such that the tension may help generate a higher radial force perpendicular to the user's hand or other body part onto the inner assembly or user's hand or other body part.

A support fastener 240 that is not part of a closed loop around the hand or part of the anatomy of a hand or other body part may be made out of a less flexible material, including but not limited to polyethylene, polyurethane, ABS, silicone, rubber, ethylene-vinyl acetate, or any other relatively light-weight material that can hold shape, and blends or laminates thereof.

In some embodiments, the support 200 or part of the support 200, filler 230 or part of the filler 230, support fastener 240 or part of the support fastener 240 may be 3D printed. In some embodiments, the support 200 or part of the support 200, filler 230 or part of the filler 230, support fastener 240 or part of the support fastener 240 may be vacuum formed to the desired shape.

The support 200, the filler 230, and/or the support fastener 240 may be integrated in, removably attached to or separate from the outer assembly 103 or other portions of the device 100. For integration, techniques known in the art including but not limited to stitching or adhesives may be used. Removable attachments may be achieved using techniques known in the art including but not limited to hook-and-loop fasteners, adjustment straps, buttons, snap buttons, cinches and spring stop toggle cord locks.

B. Outer Assembly with Pump Unit

Another technique for promoting contact between (parts of) the wearable device 100 and the concave portion of a user's palm is to use a suction source to draw the inner assembly 105 into direct contact with the user's palm. For example, the outer assembly 103 can be substantially airtight and include a suction source such as a pump unit configured to apply negative pressure to the interior of the outer assembly 103 and/or in between the outer assembly 103 and the user's skin. The pump unit can be used to conform the outer assembly 103 to the user's skin, thereby promoting contact between the inner assembly 105 and the user's skin during operation of the device 100. Alternatively or additionally, the outer assembly 103 can include a palm support 200, filler 230 or other means to promote contact between the inner assembly 105 and the user's skin while wearing the device 100.

Figure 14:
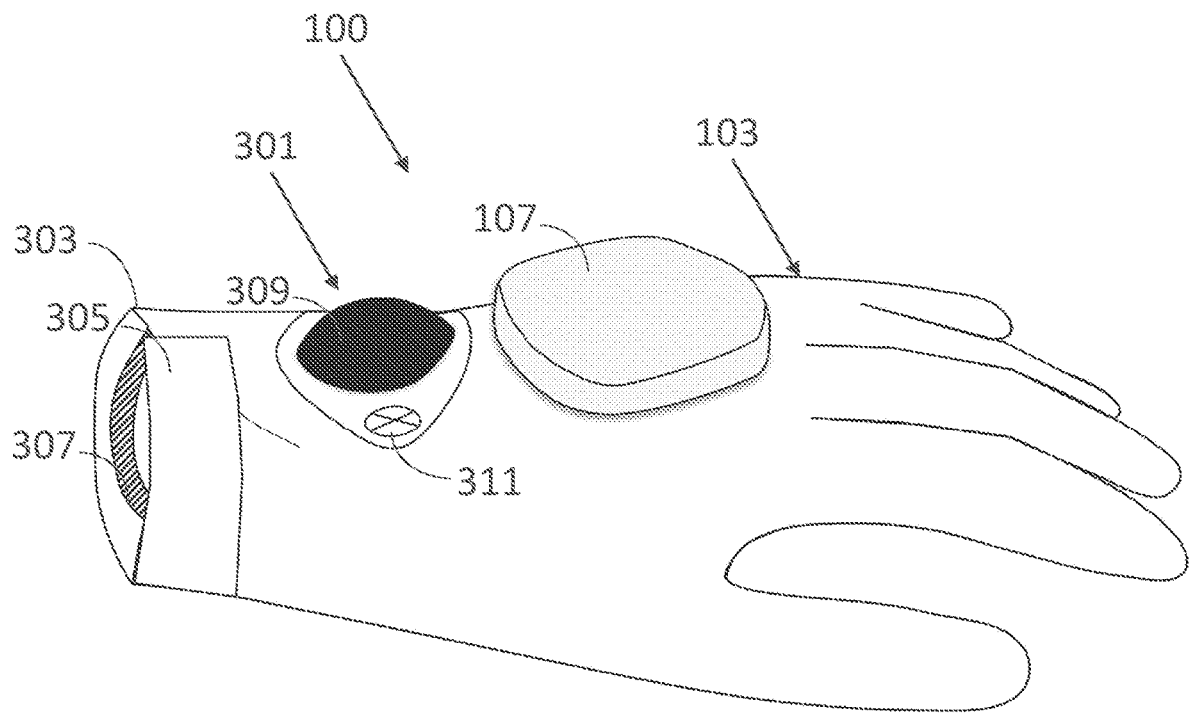
FIG. 14 illustrates a wearable device for delivering electrical current to a user's hand in accordance with embodiments of the present technology.
Figure 15:
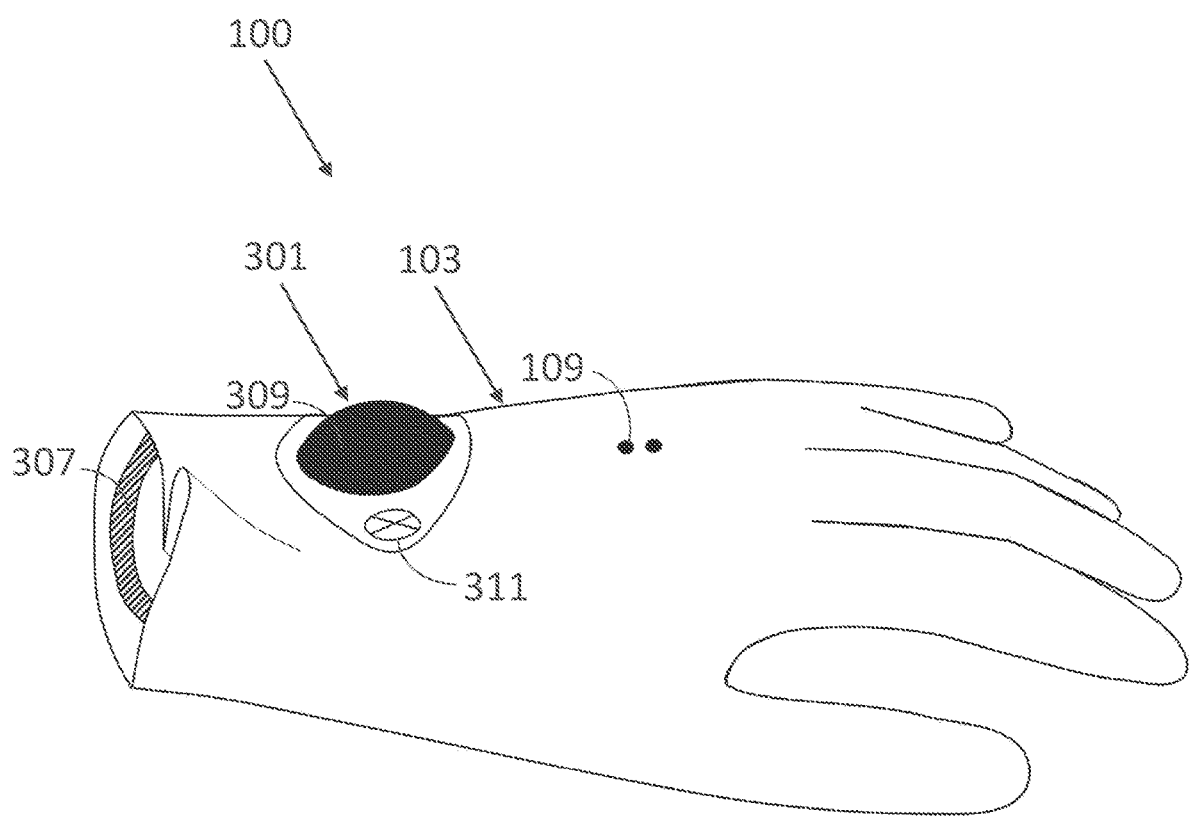
FIG. 15 illustrates a wearable device of FIG. 14 with the controller unit and fastener removed.
Figure 16:
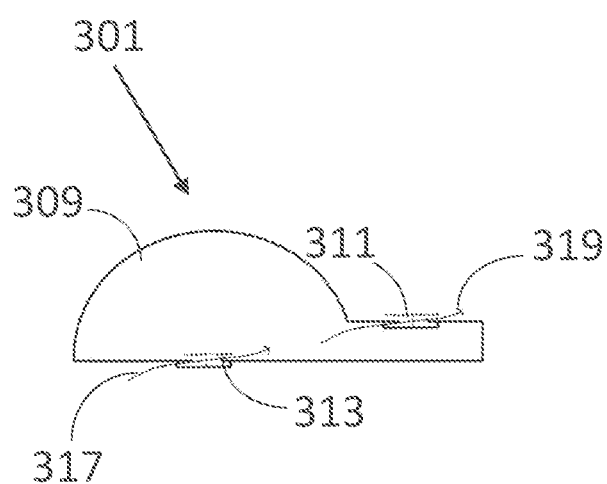
FIG. 16 illustrates a pump unit of a wearable device in accordance with embodiments of the present technology.

FIGS. 14-16 illustrate components of a wearable device 100 for delivering electrical current to a user's hand that incorporate a pump. The wearable device 100 includes a glove-shaped outer assembly 103. The inner assembly 105 can be glove-shaped and can include or carry one or more electrodes configured to deliver electrical current to a user's hand or parts of the user's hand while wearing the device 100. Alternatively, one or more electrodes or select layers of the electrodes may be carried by the outer assembly 103 to deliver electrical current to a user's hand or parts of the user's hand while wearing the device 100. The controller unit 107 (which can include a power source and a controller) can be permanently or removably attached to the outer assembly 103 and electrically coupled to one or more electrodes. The outer assembly 103 can include a suction source such as a pump unit 301 configured to apply negative pressure to the interior of the outer assembly 103 or in between the outer assembly 103 and the user's hand. As described in more detail below, the pump unit 301 can be used to conform the outer assembly 103 to the user's hand, thereby promoting contact between the inner assembly 105 and the user's hand during operation of the device 100. Alternatively or additionally, the outer assembly 103 can include a palm support component, palm filler component or other means to promote contact between the inner assembly 105 and the user's hand while wearing the device 100.

With reference to FIGS. 14 and 15, the outer assembly 103 can take the form of a glove, mitten, or other shape configured to fit over a user's hand. For example, the outer assembly 103 can be hand-shaped, including a palm portion and a plurality of finger extensions. In alternative embodiments, the outer assembly 103 can be foot-shaped, or can take the form of a pad that covers a user's under-arm region, or a pad configured to be applied over a user's forehead, or can be configured to be applied over yet other body parts.

In some embodiments, the outer assembly 103 is substantially impermeable to air. Air impermeability can be useful when a negative pressure is to be held between the outer assembly 103 and the skin covered by the outer assembly 103 while it is worn over a user's skin. For example, to promote contact between the inner assembly 105 and the user's skin, negative pressure can be supplied to the outer assembly 103 via the pump unit 301.

In some embodiments, the outer assembly 103 is substantially impermeable to water. Water impermeability of the outer assembly 103 can be useful when using a fluid such as an electrolyte solution in conjunction with the inner assembly 105, as the outer assembly 103 can retain the fluid within, minimizing or eliminating any fluid leakage.

One or multiple cuffs 303 can be included as part of a substantially air- and/or water-tight outer assembly 103 to create an air- and water-tight interior chamber within the outer assembly 103. For the hand, a cuff 303 of the outer assembly 103 can be sealed near a user's wrist. For the foot, a cuff 303 of the outer assembly 103 can be sealed near a user's ankle. The cuff 303 can include a fastener 305 disposed over an outer surface of the outer assembly 103 and a cuff liner 307 disposed on an inner surface of the outer assembly 103 circumferentially near a wrist or ankle portion. In some embodiments, the cuff 303 includes one or more notches to minimize folds when the fastener 305 is tightened over the user's wrist or ankle or other body part. The cuff liner 307 can be made out of a substantially air-tight compressible material, or can be adhesive. Separately or together, the fastener 305 and the cuff liner 307 can create a substantially air-tight seal at the user's wrist or ankle or other body part. The cuff liner 307 may facilitate use of the outer assembly 103 with a range of different body sizes, for example for users having different wrist or ankle sizes, compression of the cuff liner 307 against the user's wrist or ankle or other body part can aid in creating a substantially air-tight seal. The fastener 305 can be a strap, tab, or other structure that can be pulled to reduce the diameter of the glove at the cuff 303, and can be fixed in place using hook-and-loop fasteners, snaps, tabs, grooves, or any other fixation mechanism. In the embodiment illustrated in FIGS. 14 and 15, the cuff 303 is adapted to form a substantially air-tight seal around a user's wrist, however in other embodiments the substantially air-tight seal can be configured to be positioned elsewhere, for example at the user's ankle, further up the user's arm, or any other suitable location. In some embodiments, a gel (e.g., petroleum jelly) can be applied or pre-applied to the inside of the cuff 303 or over the user's wrist to facilitate creating a substantially air-tight seal within the outer assembly 103. Alternatively or additionally, the interior of the cuff 303 can be lined with a substantially air-tight adhesive and applied to a user's wrist when wearing the device 100. In some embodiments, an adhesive border may be used without a fastener, for example in the case of devices configured to be placed over a user's under-arm region. In some embodiments, the fastener 305 and/or cuff liner 307 can be removably attached to the outer assembly, and can be reusable or disposable.

After the fastener 305 has been tightened or after the device or parts of the device have been connected to a user's skin via adhesive or otherwise, the pump unit 301 can be utilized to remove air from the space enveloped by the outer assembly 103. As shown in FIG. 16, the pump unit 301 can include a depressible pump 306 and two one-way valves 311 and 313. The first one-way valve 311 can be in fluid communication with the exterior environment through the upper surface of the outer assembly 103, and the second one-way valve 313 can be in fluid communication with the interior space enveloped by the outer assembly 103 through the lower surface of the outer assembly 103. The first and second valves 311 and 313 are in fluid communication with one another and with the pump 309, such that upon depressing the pump 309, air is drawn from the interior space enveloped by the outer assembly 103 through the second valve 313 as illustrated by flow direction 317, and is emitted out of the first valve 311 to the exterior environment as illustrated by flow direction 319. By repeatedly depressing the pump 309 (e.g., by hand-activation, electrical activation, or other means), air can be drawn out of the interior of the inner assembly 105, the pump 309 cooperates with two one-way valves, one of which is shown as valve 311 in FIG. 3. By depressing the pump 309 repeatedly, air is removed from within the interior space enveloped by the outer assembly 103, causing the outer assembly 103 to increasingly conform to the user's hand. This conformity causes the outer assembly 103 to urge the inner assembly 105 into contact with the user's hand. At sufficiently high negative pressure levels, the inner assembly 105 can be in substantially direct contact with the user's skin along the inner surface of the inner assembly 105.

Although the illustrated pump unit 301 includes a depressible pump 309 in cooperation with one-way valves 311 and 313, in other embodiments different suction sources can be used to supply negative pressure to the outer assembly 103. In some embodiments, the two valves 311 and 313 may be replaced with a single valve, or additional valves may be used. In some embodiments, a vacuum, mechanical or electrical pump, or any other suitable suction source can be used in conjunction with the outer assembly 103 to supply negative pressure.

Alternatively or additionally to having a substantially air-tight outer assembly 103 combined with a pump unit 301 to create a negative pressure region, the outer assembly 103 can include a support structure, filler material or other means to promote contact between the inner assembly 105 and the user's skin during operation of the device 100, as described in detail elsewhere herein.

C. Inner Assembly and Electrode(s)

As noted previously, the wearable device 100 can include an outer assembly 103 and an inner assembly 105 that can reside between the outer assembly 103 and the user's skin when in use. The inner assembly 105 may be positioned over a body part, for example the user's palm, sole or under-arm, or may envelope a body part, for example the user's hand or foot or under-arm and shoulder region. The inner assembly 105 can include a treatment side configured to face a treatment site and a passive side that is not configured to deliver electrical energy. Both the treatment side and the passive side can include multiple separate sections that together make up the treatment side or passive side respectively. The inner assembly 105 may define gaps in which no material is present. In some embodiments, these gaps may be aligned with joints or other natural bending points such as the knuckles of the hand, along the wrist, ankle joint, toe joints etc.

With reference to FIGS. 17A-18A, the inner assembly 105 can take the form of a glove, mitten, or other shape configured to fit over a user's hand or other body part intended for treatment with the device 100. For example, the treatment side of inner assembly 105 can be hand-shaped, including a palm portion and a plurality of finger extensions, to face substantially the palmar side of the hand when in use. The passive side of inner assembly 105 can be hand-shaped, including a palm portion and a plurality of finger extensions, to face substantially the dorsal side of the hand when in use. In alternative embodiments, the inner assembly 105 can be foot-shaped, take the form of a sock, sock with separate toes, or can take the form of a pad that covers a user's under-arm region, or a pad configured to be applied over a user's forehead. In some embodiments, the inner assembly 105 can be integrated into the outer assembly 103, for example being substantially air-tight and having a pump unit 301 disposed therein and/or being form-fitting with a support 200, filler 230, or other means to improve contact between the inner assembly 105 and the user's skin.

Figure 17A:
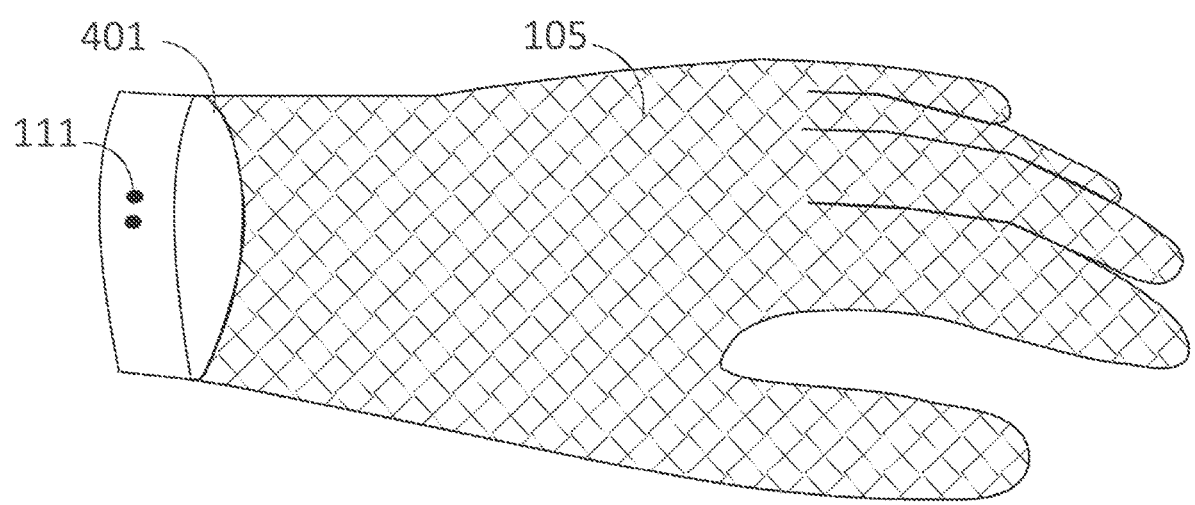
FIG. 17A illustrates a dorsal view of an inner assembly of a wearable device in accordance with embodiments of the present technology.
Figure 17B:
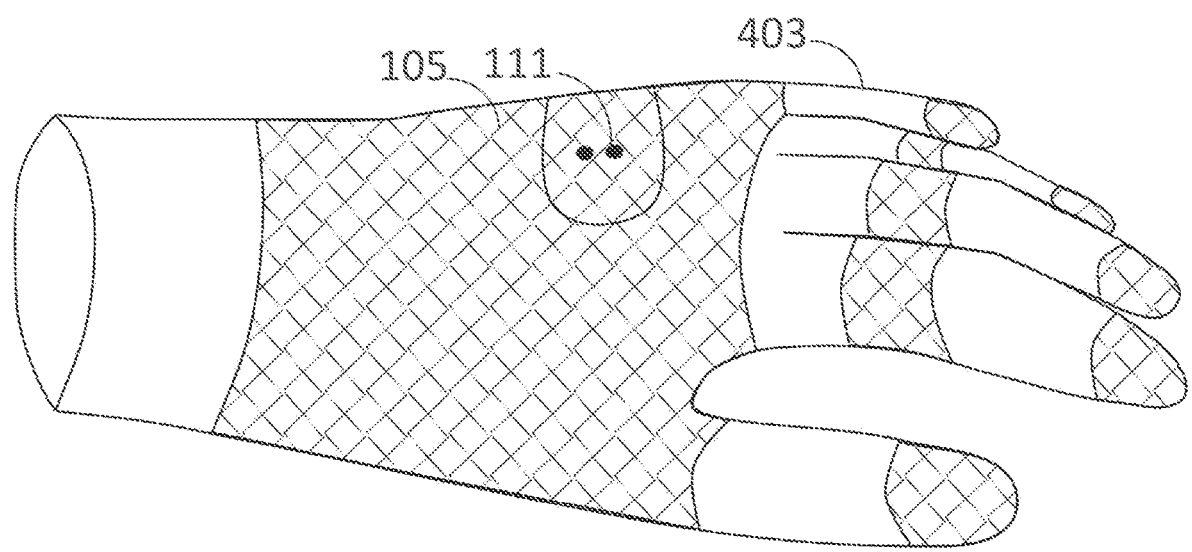
FIG. 17B illustrates a dorsal view of an inner assembly of a wearable device in accordance with embodiments of the present technology, as worn on a user's hand.

In some embodiments, the inner assembly 105 may not have a passive side, may not be fully closed, or may cover only a portion of the dorsal side of the user's hand. For example, as illustrated in FIG. 17A, the inner assembly 105 with an opening 401 in which to insert a hand, may have a mesh-like structure on the entirety or a portion of the dorsal side. As illustrated in FIG. 17B, this mesh-like or other structure may define gaps 403 in which no material is present. In some embodiments, the inner assembly 105 can be less or non-conductive along the passive or dorsal side, can be substantially water impermeable, and/or can allow breathability.

Figure 18A:
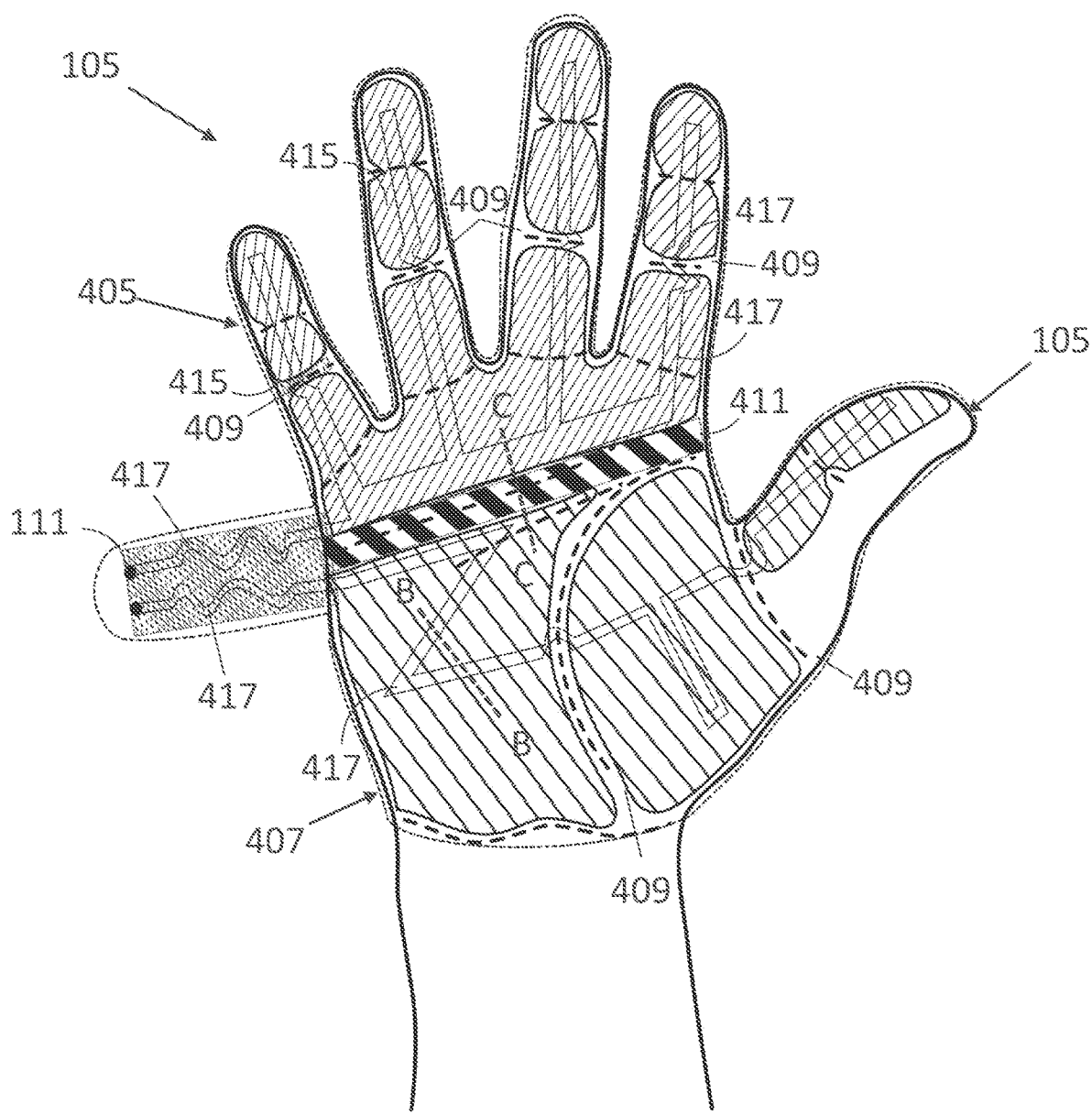
FIG. 18A illustrates a palmar view of an inner assembly of a wearable device in accordance with embodiments of the present technology, as worn on a user's hand.

As best seen in FIG. 18A, according to one embodiment, the inner assembly 105 can carry a first electrode 405 and a second electrode 407 that are separated from one another by a barrier 411. The electrodes 405, 407 can together form a substantially hand-shaped component. Although the electrode shapes here include a first electrode 405 shaped to correspond to the upper palm and the fingers and the second electrode 407 shaped to correspond to lower palm and thumb, various other configurations are possible. For example, a left half of the hand may be substantially covered by a first electrode, while the right half of the hand may be substantially covered by a second electrode. As another example, all five fingers may be substantially covered by the first electrode, while the lower palm may be substantially covered by the second electrode. The electrodes 405 and 407 can each include a plurality of segments, for example with conductive portions being separated by less or non-conductive portions along breaks 409, which can be positioned along areas where more stretching is desired. If segments of the same electrode are separated by a less or non-conductive portion, they may still connect electrically (permanently or reversibly) through separate means, for example by means of a conductive wire. As shown in FIG. 18A, these breaks 409 can be positioned along natural bending points, for example at joints of the finger and along creases of the palm. In some embodiments, there may be three, four, or more different electrodes carried by the inner assembly. In some embodiments, there may be only one electrode carried by the inner assembly, and this one electrode may be in electrical communication with an electrode on a second inner assembly covered by the same or a different outer assembly or remain uncovered. In these cases the electrical communication may be completed by a body part and/or a conductive wire, clothing with conductive elements or other means. In some embodiments, the electrodes are configured to contact more than about 500% of the body part to be treated (e.g., more than 500% of the palm).

Figure 18B:
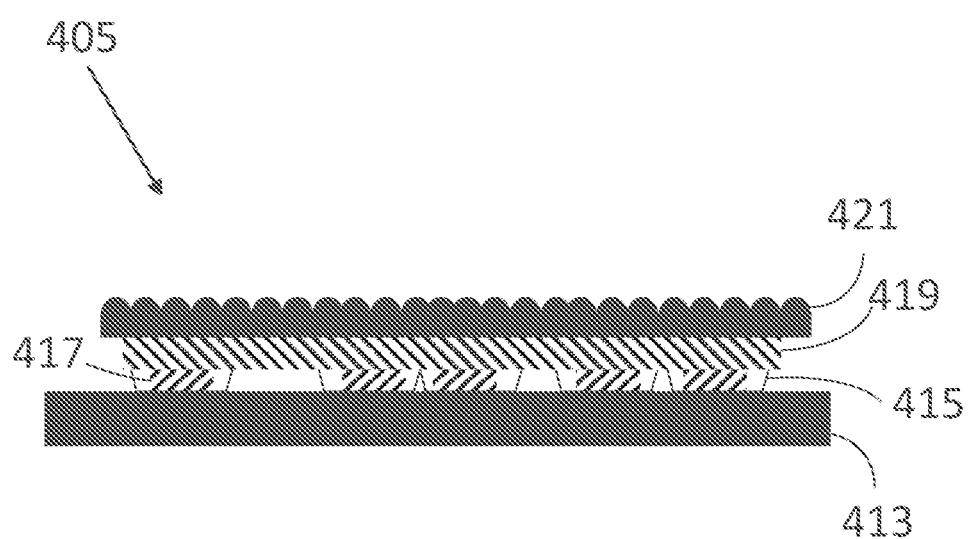
FIG. 18B illustrates a cross-sectional view of a portion of an inner assembly taken along line B-B in FIG. 18A.

In some embodiments, the first and second electrodes 405, 407 can have substantially similar constructions, with different shapes as appropriate. FIG. 18B illustrates a cross-sectional view of a portion of the inner assembly taken along line B-B in FIG. 18A (although the cross-sectional view in FIG. 18B illustrates a differing number of conductive traces 417). As seen in FIG. 18B, the electrode 407 can include various electrode layers, from the outer side (configured to face away from the skin when worn) to the inner side (configured to face towards the user's skin when worn): a base layer 413, a substantially non-conductive encapsulant 415, conductive traces 417, a conductive layer 419, and a bolster layer 421. In some embodiments, one or more of these layers or components can be omitted, and/or one or more additional intervening layers or components can be included. Additionally, these layers or components can be arranged in different orders from those listed above depending on the desired configuration.

In some embodiments, the base layer 413 is configured to face away from the user's skin when worn by a user. The base layer 413 can be made out of a non-conductive material such that electrical current does not pass through the base layer 413. In some embodiments, the base layer 413 is stretchable, and can be made out of a waterproof and/or minimally absorbing material (e.g., neoprene, nitrile, fabric with polyurethane laminate coating, a thermoplastic polyurethane (TPU) layer, etc.) or a combination of those.

Figure 20A:
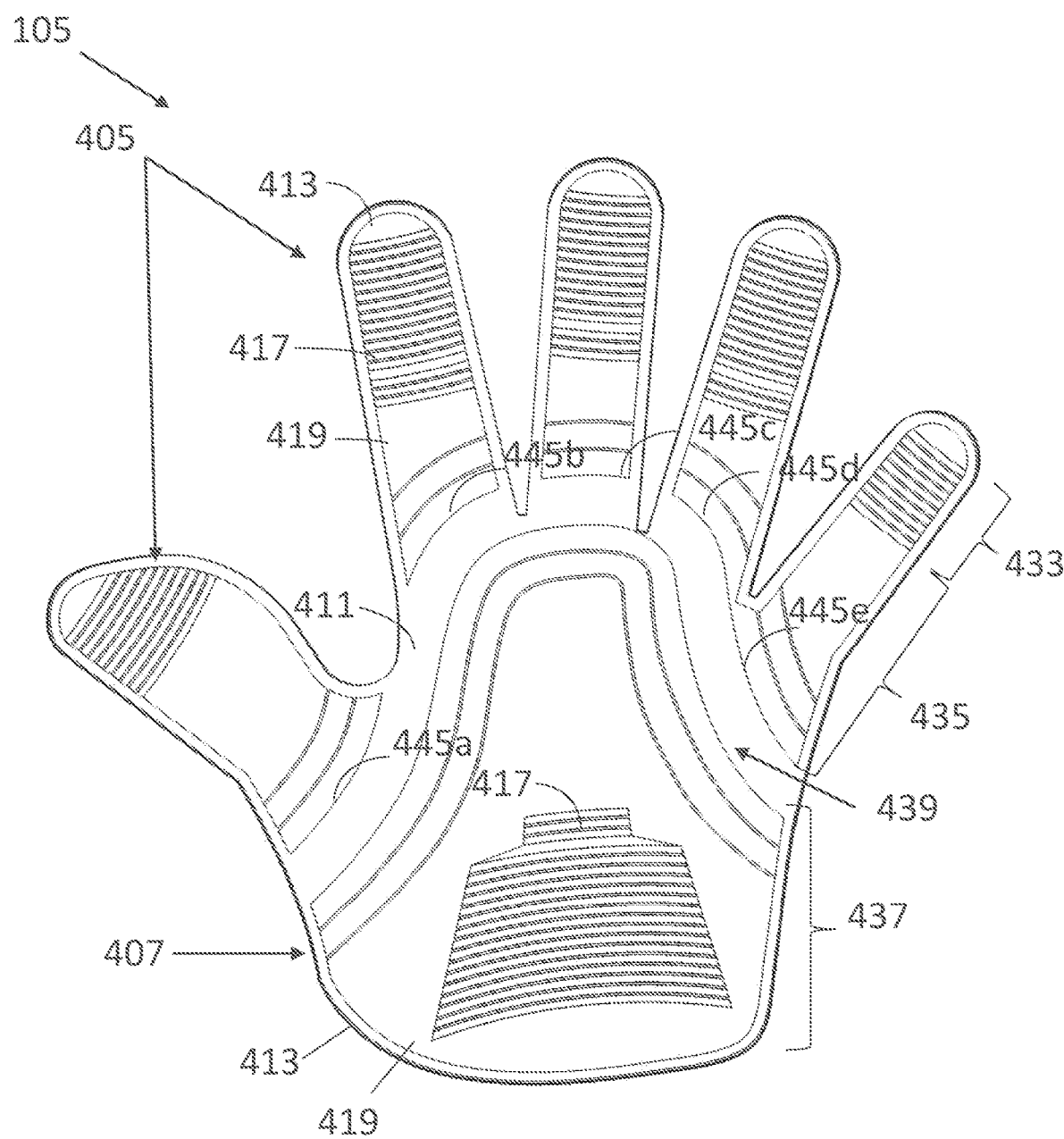
FIG. 20A illustrates a lay-out of electrode layers of an inner assembly of a wearable device in accordance with embodiments of the present technology.

The conductive traces 417 can be a sheet layer of constant or varying thickness or can include a multitude of conductive segments or traces of the same or varying thickness that span over a portion or the entirety of the base layer 413. As seen in FIG. 18A, the conductive traces 417 can be in electrical communication with the connector 111. In some embodiments the connector 111 allows for permanent or non-permanent electrical connection to the connectors 109 of the overlying outer assembly 103, which in turn connect to the controller unit 107. Accordingly, when the device 100 is assembled, the controller unit 107 is in electrical communication with the conductive traces 417 via the connectors 109 and 111, thereby allowing the controller unit 107 to deliver current to the electrodes 405 and 407 via the conductive traces 417. The conductive traces 417 can be made out of substantially conductive material, for example silver, silver alloys, carbon-containing materials (e.g., silicone or TPU with carbon black or carbon nanotubes), platinum, stainless steel, conductive polymers, PEDOT, copper, or any other suitable conductive material. The conductive traces 417 may be attached to, printed onto or otherwise electrically connected with the conductive layer 419. The conductive traces 417 may be attached to, printed onto or otherwise connected to a substrate (e.g., TPU) that is then connected to the base layer 413 (e.g., thermal bonding, adhesives, ultrasonic bonding). Additionally or alternatively, the conductive traces 417 may be attached to, printed onto or otherwise connected with the base layer 413 or bolster layer 421 directly, without an intervening layer or substrate. Segments of the conductive traces 417 (and potentially also the underlying substrate if present) may be sheet layers, or may be generally straight, except in certain locations where more stretch is desirable. In these certain locations the conductive traces 417 can have a zigzag or squiggly pattern perpendicular to the direction of desired stretch. As seen in FIG. 18A, according to one embodiment, the conductive traces 417 are substantially straight along portions of the fingers, with a squiggle or zig-zag pattern at the bends in the fingers and along portions of the palm where creasing is expected. Alternatively the conductive traces 417 allow about as much as or more stretch than the base layer 413 itself in which case no such zig-zag portions may be used. The lay-out of conductive traces 417 may also help optimize total current density distribution in the sweat ducts, stratum corneum or other skin tissue or distribution of current density into the user's skin. As seen in FIG. 20A, gaps between conductive traces 417 may be organized substantially parallel to the barrier 411. These gaps may be substantially 0.5 mm in width, 1 mm in width, 2 mm in width, 5 mm width or any other gap size. The conductive traces 417 may be thin traces, for example 10-100 µm in width, 0.1-1 mm in width, 1 mm-1 cm in width or 1-2 cm in width. The width may also vary across the conductive traces 417. For example, as illustrated in FIG. 20A, the conductive traces 417 may include multiple segments per electrode of 2 mm width, with a 0.5 mm gap between adjacent segments, and where the segments are laid out substantially parallel to the barrier 411 between the two electrodes. The width of each segment may also very between segments, for example with different segment and gap width between fingers. The conductive traces 417 may be off-set from edges of other layers, for example by a distance of between 0.1-0.5 mm, 0.5-1 mm, 1-5 mm, 5-10 mm or more from edges of the bolster layer 421.

The conductive layer 419 can be a sheet layer of constant or varying thickness or can include a multitude of conductive segments (e.g., traces) of the same or varying thickness. The conductive layer 419 can be in electrical communication with the conductive traces 417 through permanent or reversible physical connection. The conductive layer 419 may be attached to, printed onto or otherwise connected with the base layer 413 or bolster layer 421. If an adhesive is used for this connection, the adhesive may be electrically conductive (e.g., carbon-filled adhesive) or may be an electrically non-conductive adhesive (e.g., covering less than 0.1-1%, 1-5%, 5-20% or 20-50% of the surface area of the treatment site). Each electrode may have a separate conductive layer 419 or the conductive layer 419 or segments of the conductive layer 419 may be continuous between electrodes, and even go beyond any other electrode layer. In some embodiments, the conductive layer 419 can be made out of substantially conductive material, for example silver, silver alloys, carbon-containing materials (e.g., silicone or TPU with carbon black or carbon nanotubes), platinum, stainless steel, conductive polymers, PEDOT, copper, or any other suitable conductive material. The conductivity of the conductive layer 419 may be higher than the conductivity of the conductive traces 417, or may be lower everywhere or in certain areas. The conductive layer 419 for each electrode can include segments, with breaks 409 in certain locations where more stretch is desirable, for example along joints of the fingers or in the crease of the palm. Alternatively the conductive layer 419 allows about as much as or more stretch than the base layer 413 itself in which case no breaks 409 may be used. The lay-out of conductive layer 419 may also help optimize total current density distribution in the sweat ducts, stratum corneum or other skin tissue or distribution of current density into the user's skin. As seen in FIG. 20A, gaps between conductive layer 419 may be organized substantially parallel to the barrier 411. These gaps may be between 0.1-0.5 mm in width, 0.5-1 mm in width, between 1-2 mm in width, between 2-5 mm in width, or between 5-20 mm in width. The conductive layer 419 may be thin traces, for example substantially between 10-100 μm in width, 0.1-1 mm in width, 1 mm-1 cm in width or 1-2 cm in width or any other width. The width may also vary across the conductive layer 419. For example, as illustrated in FIG. 20A, the conductive layer 419 may include three segments per electrode of different width, with a 1 mm gap between adjacent segments, and where the segments are laid out substantially parallel to the barrier 411 between the two electrodes, and/or substantially parallel to the perimeter 445a, 445b, 445c, 445d, 445e of electrode 405 adjacent to electrode 407. The width of each segment may also vary between segments, for example with different segment width between fingers, or with different segment width between different portions of an electrode. The conductive layer 419 may be off-set from edges of other layers, for example by a distance of between 0.1-1 mm, 1-5 mm, 5-10 mm or more from edges of the bolster layer 421 and a distance of between 0.1-1 mm, 1-5 mm, 5-10 mm or more from edges of the conductive traces 417. It is believed that the lay-out of the various layers as well as their relative conductivities and thicknesses determines the distribution of electrical current density (or other type of energy) over the treatment site. Other embodiments of electrodes are described further in this specification.

As shown in FIG. 18B, according to some embodiments, an encapsulant 415 can surround the conductive traces 417 along portions that do not face the conductive layer 419. For example, this can be done to protect ink traces 417 from moisture if the base layer 413 is protruded or absent. The encapsulant 415 can be a non-conductive and stretchable material.

In some embodiments, certain portions of the conductive traces 417 can be completely covered by a substantially non-conductive encapsulant 415, for example along portions of the conductive traces 417 that extend between adjacent segments of the conductive layer 419 (e.g., across breaks 409 where more stretching is desired). As a result, the breaks 409 may be substantially non-conductive along the surface even though the conductive traces 417 and/or the conductive layer 419 extend across the breaks 409.

A bolster layer 421 may be disposed over parts of or the entirety of the conductive layer 419 and may be configured to contact the user's skin when the device is in use. Each electrode may have a separate bolster layer 421 or the bolster layer 421 may be continuous between electrodes, and even go beyond any other electrode layer. In some embodiments, the bolster layer 421 can be made out of a water-absorbent material, for example felt, microfiber, polyurethane foam, PVA foam, or other suitable material. In some embodiments, the bolster layer 421 can be made out of a water-absorbent material that does not substantially expand with water absorption, for example a material with less than 5%, 10%, 20% or 25% of expansion in the x- or y-direction when in contact with water. In operation, the bolster layer 421 can hold an electrolyte, or a pH-buffered electrolyte to keep the pH substantially around pH 3, 4, 5, 6, 7, 8, 9, 10, 11 or another pre-defined pH value between 3-11. pH buffers that may be used include but are not limited to phosphate, acetate, bicarbonate, MES, glutamate buffers. Alternatively or additionally, the bolster layer can hold a solution having anti-bacterial properties. Alternatively or additionally, the bolster layer can hold an HCl- or NaCl-containing solution or other chloride-rich solution. The solution held by the bolster layer 421 may be the same or different between electrodes of the same device 100. Alternatively or additionally, the bolster layer 421 can include a hydrogel or hydrogel-based material (e.g., hydrogel TPU). The bolster layer 421 for each electrode 405, 407 includes segments, with breaks 409 in certain locations where more stretch is desirable. Alternatively the bolster layer 421 allows about as much as or more stretch than the base layer 413 and/or conductive layer 419 in which case no breaks are required. In some embodiments, the segments of the bolster layer 421 can be larger in surface area than those of the underlying conductive layer 419. The bolster layer 421 can have a thickness of between 0.1-1 mm, 1-5 mm, 5-10 mm, 1-3 cm, or 3-5 cm. The thickness may also vary across the layer.

Figure 18C:
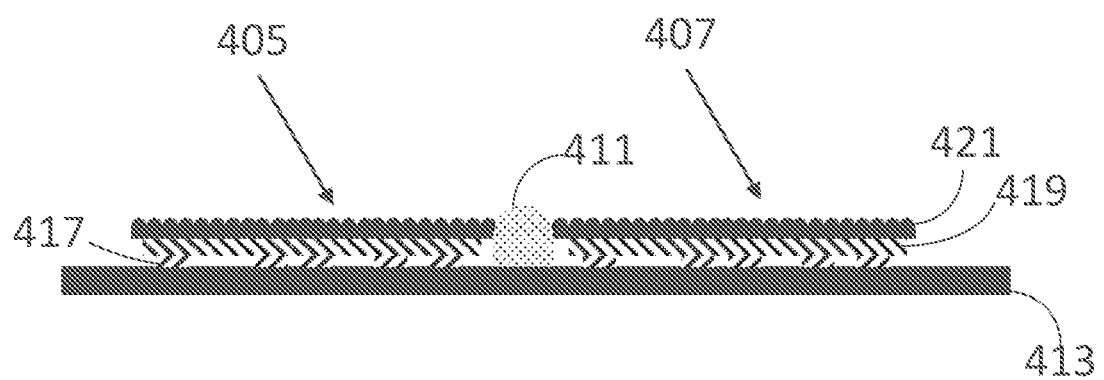
FIG. 18C illustrates a cross-sectional view of another portion of an inner assembly taken along line C-C in FIG. 18A.

FIG. 18C illustrates a cross-sectional view of a portion of the inner assembly taken along line C-C in FIG. 18A (although the cross-sectional view in FIG. 9C illustrates a differing number of conductive traces 417). As seen in FIG. 18C, adjacent electrodes 405 and 407 can be separated from one another by a barrier 411. The barrier 411 can be made out of a substantially non-conductive material and can be water-repellant, for example made of a non-porous polyurethane, neoprene, EVA or other suitable material (potentially as a foam). The barrier 411 can be shaped in a convex fashion with respect to the skin to avoid electrolyte, sweat or other liquids collecting in between adjacent electrodes. For example, the barrier 411 can include a non-conductive protrusion that projects beyond a surface of the adjacent electrodes 405, 407. The barrier 411 can be stretchable, for example as stretchable as or more stretchable than the base layer 413 or as stretchable as or more stretchable than the bolster layer 421. In some embodiments, the barrier 411 can maintain a separation between adjacent electrodes 405, 407 of between about 1-5 mm, 5-10 mm, or 1-3 cm. The separation between adjacent electrodes 405, 407 may also vary along the length of the barrier 411. Alternatively, the barrier 411 can be a less conductive material, such as the same material as or continuous with the bolster layer without other more conductive layers of the adjacent electrodes, or the same material as or continuous with the bolster layer. Not fully physically separating adjacent electrodes may simplify construction.

Figure 18D:
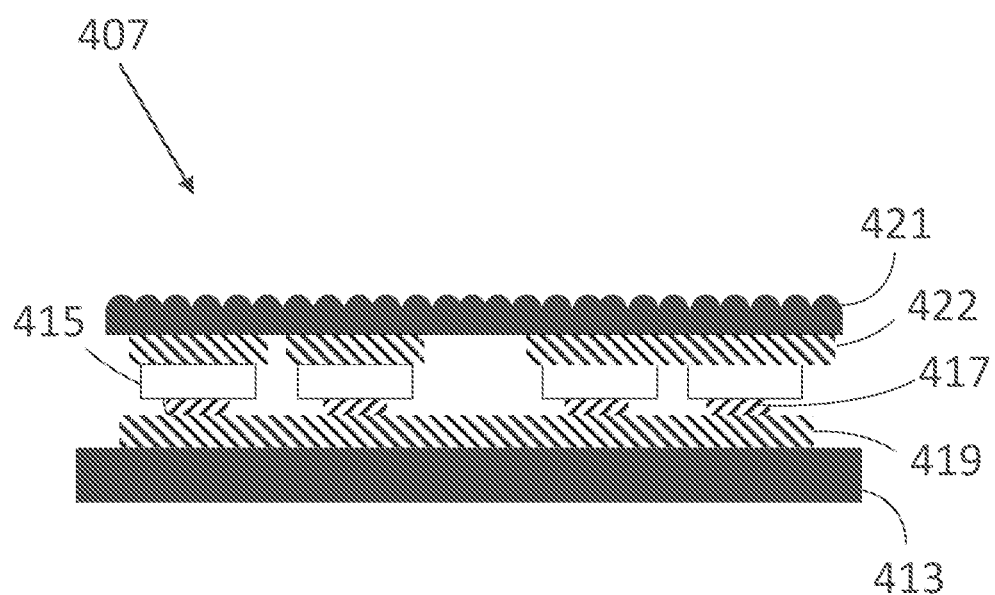
FIG. 18D illustrates another cross-sectional view of an inner assembly.

FIG. 18D illustrates yet a different embodiment, in which the electrode 407 includes, from the outer side (configured to face away from the skin when worn) to the inner side (configured to face towards the user's skin when worn): a base layer 413, a first conductive layer 419, conductive traces 417, a non-conductive encapsulant 415, a second conductive layer 422, and a bolster layer 421. The non-conductive encapsulant 415 can protect against potential migration of ions from the conductive traces 417 into the bolster layer 421 and into the user's skin.

In some embodiments, the outer assembly 103 may include all or some layers of the electrode(s) while the inner assembly 105 includes the remaining layers of the electrode(s). For example, the inner assembly 105 may include the bolster layer 421, while the outer assembly 103 includes the conductive traces 417 and conductive layer 419. Electrodes are connected to a power source (described below). In some embodiments, conductive traces or wires are used to connect a terminal of a power source or controller unit to an electrode. As illustrated in FIG. 19B such a conductive trace 418 may run from a (pre-determined) position on the electrode and towards the location on the electrode where a voltage substantially equal to the voltage at the power source or controller unit terminal is desired. The conductive trace 418 may have a non-zero resistance, in which case the voltage at the other end of the trace may be lower or higher than the voltage at the power source or controller unit terminal. The conductive traces or wires 418 may be run between adjacent electrodes, or may take up space that would otherwise be taken up by a conductive layer. The conductive traces 418 may be covered with an encapsulant (not shown) or other material of low electrical conductivity so substantially no current or only a low amount of current will flow from the conductive trace 418 directly into the tissue without passing through other conductive layers of the electrode. The encapsulant may be 0.001-0.1 mm, 0.1-0.2 mm, 0.2-0.5 mm, 0.5-1 mm, 1-10 mm wider than the conductive trace 417. Spacing between these conductive traces and other parts of the conductive layer may be 0.001-0.1 mm, 0.1-0.2 mm, 0.2-0.5 mm, 0.5-1 mm, 1-10 mm or more. A conductive trace 418 may electrically connect with a conductive trace 417 or other part of the electrode 405, 407 through an electrical connection point 440a-f. The majority of other conductive traces 417 of one electrode 407 may be placed in an area more proximate to the other electrode 405 than the electrical connection point 440f. The majority of other conductive traces 417 of electrode 405 may be placed in an area more proximate to the other electrode 407 than the electrical connection points 440a-e.

D. Electrode Configurations for Improved Current Distribution

When energy such as electrical current is delivered to the skin or other bodily tissue, this may be done by placing two or more electrodes against the skin or bodily tissue. These electrodes may be connected to opposing poles of a power source, for example the system may be mains-powered or powered through a (DC) battery. For example, in the case of two electrodes, one electrode may be connected to the positive terminal of the power source, while the other electrode may be connected to the negative terminal of the power source. The electrodes may include one or multiple conductive layers, which may also include conductive traces. According to some embodiments, the electrode could be mechanically separate, connected by non-conductive materials, or even connected by materials with some level of conductivity. In the latter case, it is believed that an amount of energy may flow from one electrode to another electrode without going through the skin or other bodily tissue.

It may be desirable to be able to control the distribution of electrical current or other types of energy across an electrode surface. For example, a uniform distribution or non-uniform distribution across the electrode surface may be desirable.

Figure 19A:
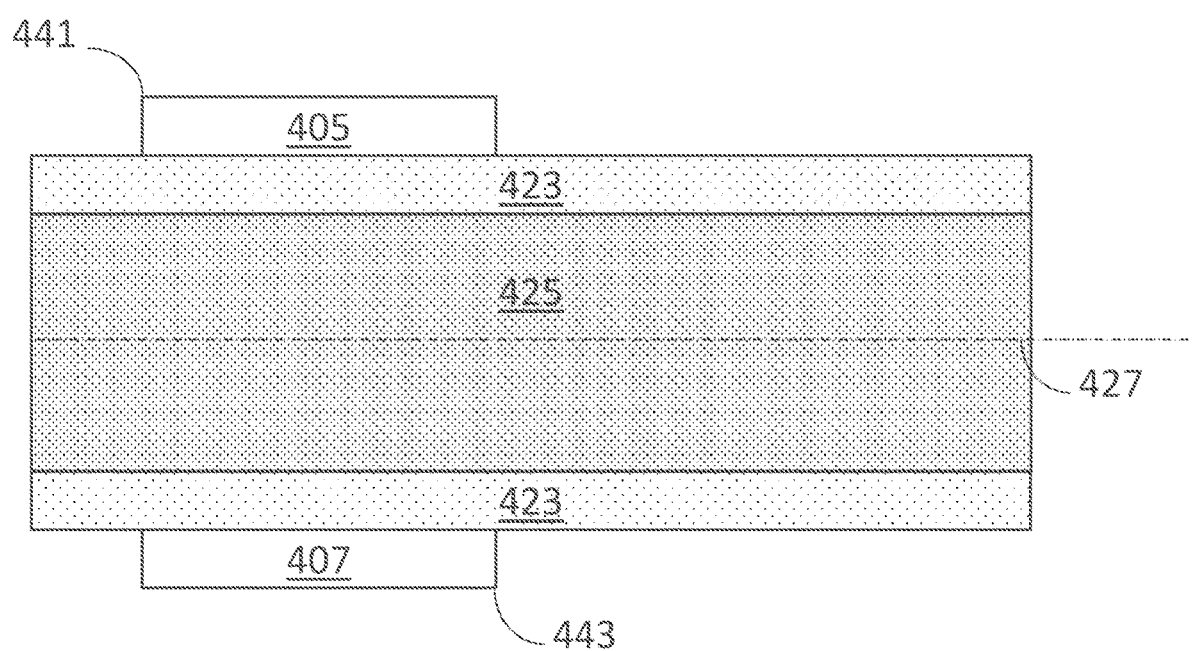
FIG. 19A illustrates a cross-section of two electrodes of uniform conductivity across the electrode placed on skin in accordance with embodiments of the present technology.
Figure 19B:
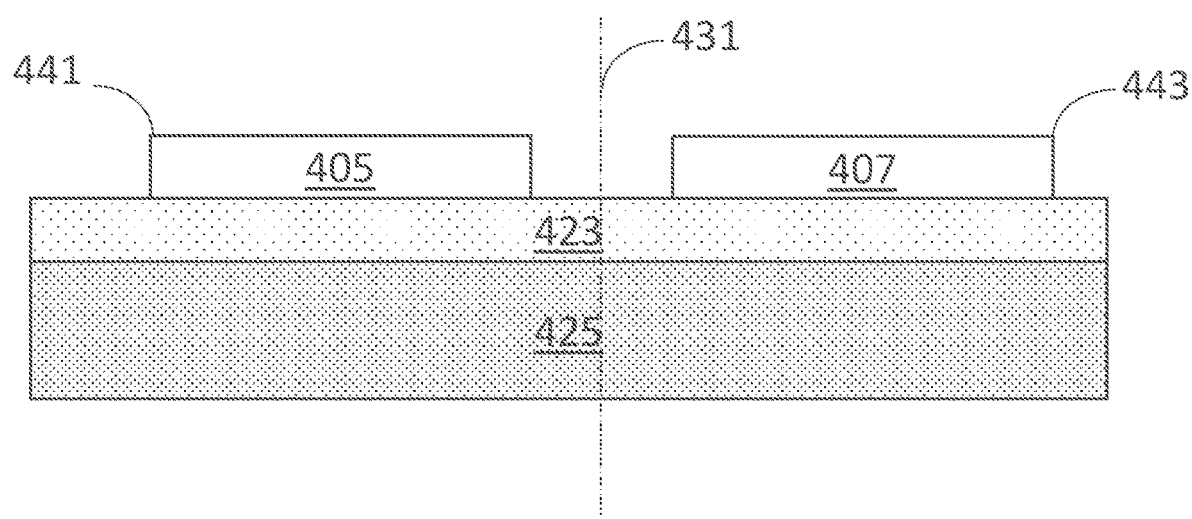
FIG. 19B illustrates a cross-section of two electrodes of uniform conductivity across the electrode placed on skin in accordance with embodiments of the present technology.
Figure 19C:
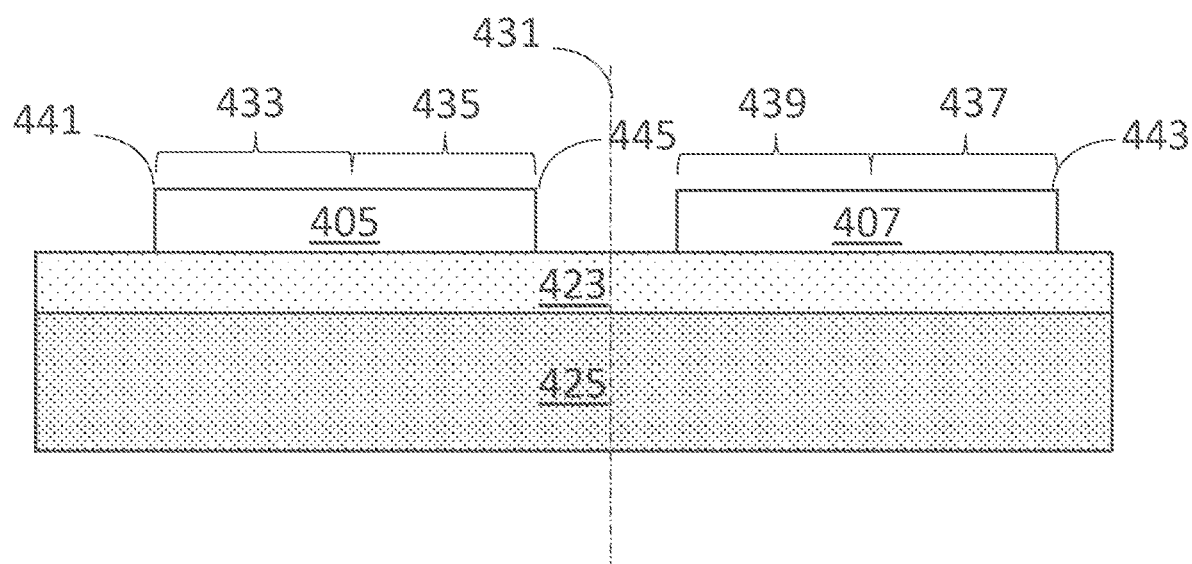
FIG. 19C illustrates a cross-section of two electrodes of non-uniform conductivity across the electrode placed on skin in accordance with embodiments of the present technology.
Figure 19D:
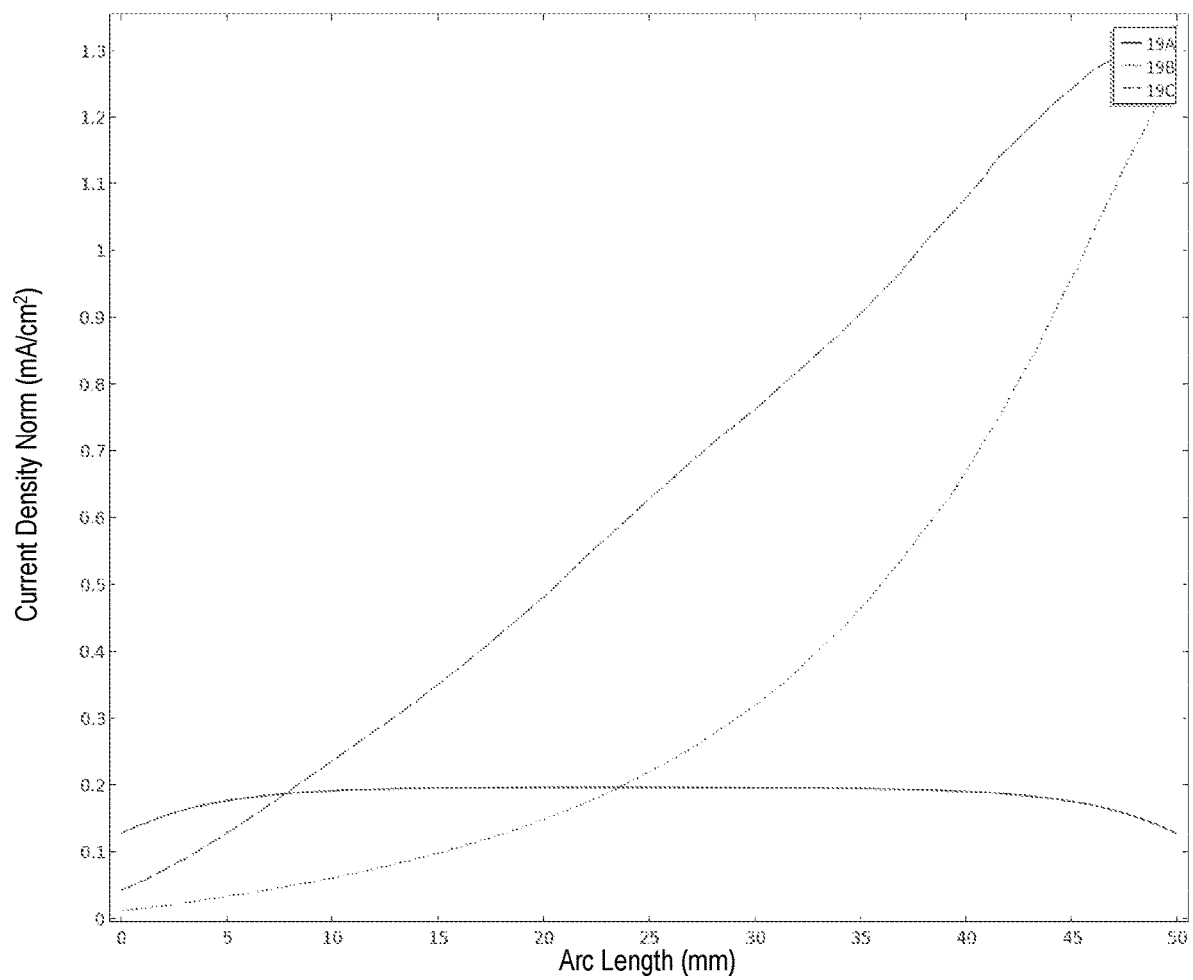
FIG. 19D illustrates the current density across the skin under an electrode from FIGS. 19A-C.
Figure 19E:
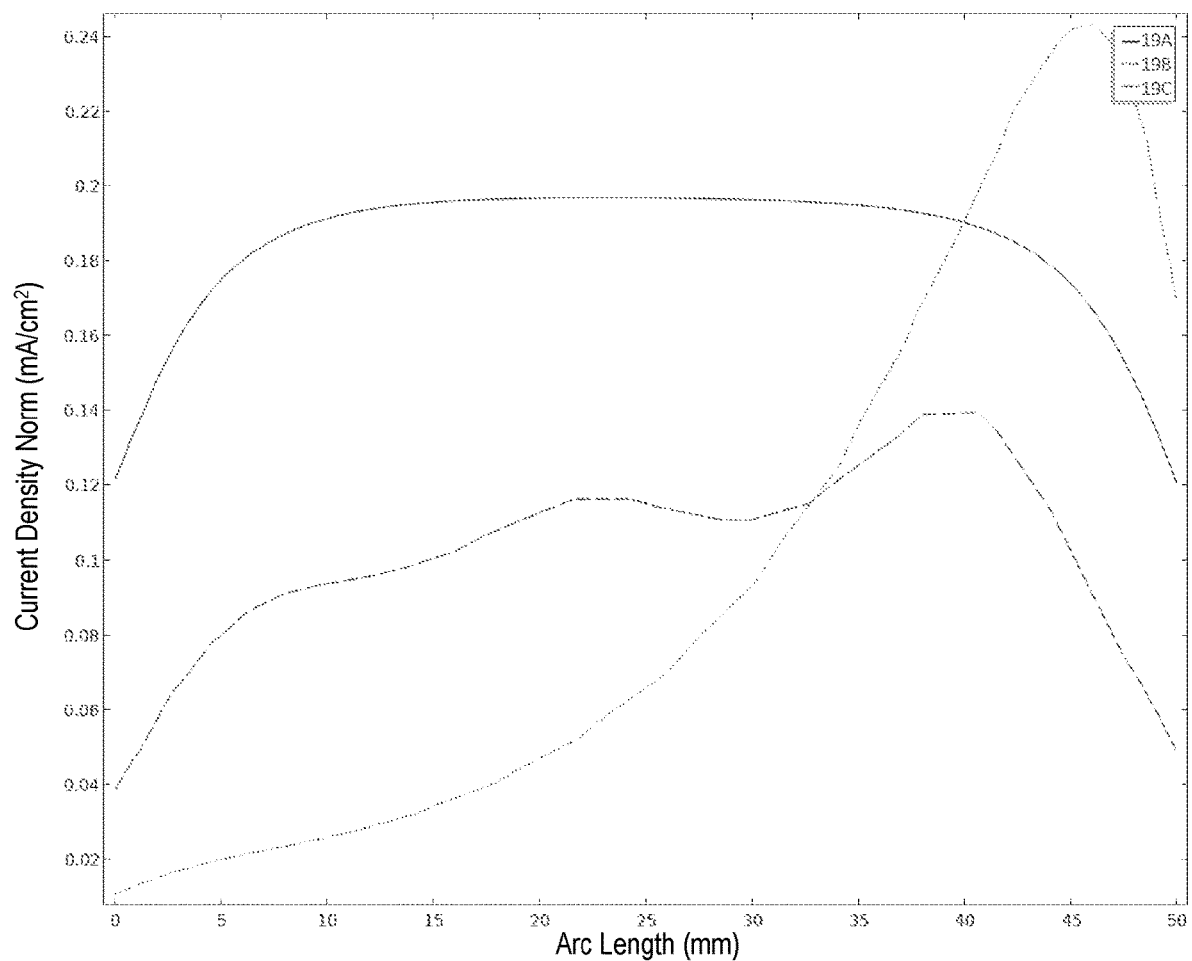
FIG. 19E illustrates the perpendicular component of the current density across the skin under an electrode from FIGS. 19A-C.

FIGS. 19A-19C illustrate example configurations of first and second electrodes 405, 407 positioned relative to a user's skin 423 with underlying tissue 425 (e.g., muscle, bone). In FIG. 19A, the two electrodes 405 and 407 are disposed on opposite sides of a user's body part (e.g., the first electrode 405 may be on a palmar side of a user's hand and the second electrode 407 may be on the dorsal side of a user's hand). In FIG. 19B, two electrodes 405, 407 are laterally spaced apart from one another across the same side of the user's skin 423. In FIG. 19C, the two electrodes 405, 407 are arranged similar to the configuration of FIG. 19B, except in FIG. 19C the electrodes 405, 407 are configured to have non-uniform conductivity, for example having regions with varying density of conductive traces or other elements to provide non-uniform conductivity across the surfaces of these electrodes 405, 407. It is assumed here that one terminal of a power source is in electrical connection with a point, line or zone near the electrode perimeter 441 on electrode 405, and that the other terminal of the power source is in electrical connection with a point, line or zone near the electrode perimeter 443 on electrode 407. Note that, in these examples, the electrical current entry zones 441, 443 are near electrode perimeters that are furthest away from each other on the respective electrodes. FIG. 19D illustrates the resulting current density across the length of the first electrode 405 in each of these configurations. FIG. 19E illustrates the resulting perpendicular component of the electrical current across the length of the first electrode 405 in each of these configurations.

For electrodes of substantially uniform conductivity, if the surfaces of electrodes that are opposing in polarity but substantially similar in shape, size and construction, are substantially facing each other, the distribution across the electrode surfaces is believed to be substantially uniform. For the example of FIG. 19A, the first and second electrodes 405 and 407 can each include a bolster layer, a conductive layer (e.g., a segmented carbon layer), and conductive traces (e.g., discrete traces of silver or other conductive material, separated from one another across the conductive layer), as described elsewhere herein. (As used herein, "trace" can refer to any discrete conductive element, for example an elongated segment, portion, strip, etc. having any suitable shape.) The first electrode 405 is placed against skin 423, with other tissue 425 underneath, and the second electrode is placed over skin 423 on an opposite side, with line 427 the symmetry line between the first and second electrodes 405, 407. As illustrated in FIG. 19D and FIG. 19E, the electrical current and perpendicular component of the electrical current respectively in the skin 423 are uniformly distributed across the first electrode 405, with a similar distribution across the second electrode 407. This may be desirable, or it may be desirable to have a non-uniform distribution across these electrode surfaces.

Again for electrodes of substantially uniform conductivity, if the surfaces of electrodes of opposing polarity are not facing each other, and/or the electrodes are different in size, shape and/or construction, the distribution across these electrode surfaces may be different. This may or may not be desirable depending on the application. For example, for a set-up with two electrodes of opposing polarity, the perimeter of the first electrode closest to the second electrode may have a higher current density than the remainder of this first electrode. For example, for a substantially rectangular electrode placed somewhere on the upper body, and a substantially rectangular electrode placed somewhere on a leg of the same person with both electrodes of uniform conductivity, the edge of the electrode on the leg closer to the upper body may have a higher current density than the rest of that electrode. For the example of FIG. 19B, a first electrode is placed against the skin 423, with other tissue 425 underneath, and the second electrode 407 is positioned laterally adjacent to, but spaced apart from, the first electrode 405 across the skin 423, with line 431 being the symmetry line. As illustrated in FIG. 19D and FIG. 19E, the distribution of electrical current in the skin layer is not uniformly distributed across the first electrode 405, with higher current levels in the portion of the first electrode 405 that is closer to the second electrode 407. This may be desirable, or it may be desirable to have a uniform distribution or other type of non-uniform distribution across these electrode surfaces.

Additionally, if the electrodes have more complex shapes, for example a triangular electrode, a hand-shaped electrode, or an electrode with one or multiple finger- or thumb-shaped protrusions, the current density across one electrode surface in an area further away from the other electrode may be lower than the current density across that first electrode surface in other areas.

According to some embodiments, the conductivity of one or both of the electrodes 405, 407 may be non-uniform to better control the current density distribution across the electrode surface(s). According to one embodiment, this non-uniform conductivity may be achieved by laying down different thicknesses of conductive material, for example as a continuous or step-wise gradient in a portion of the electrode or for the entirety of the electrode. For example, the conductive material may be thicker in the area closer to the other electrode than in the area further away from the other electrode.

According to one embodiment, the conductivity of a conductive layer or conductive traces changes gradually or step-wise, e.g. by using more conductive material (e.g., silver) in the area further away from the other electrode and less conductive materials (e.g., carbon) in the area closer to the other electrode. For example, the ratio in conductivity levels may be 1.01-2×, 2-5×, 5-10×, 10-100×, 100-1000× or more. According to one embodiment, the conductive layer(s) or conductive trace(s) may also contain(s) resistive materials, with more resistive material in the area closer to the other electrode than in the area further away from the other electrode. In some embodiments, the conductive layer contains gaps (no material) to increase overall resistance. Alternatively or additionally, the conductive layer includes conductive traces with gaps in between them. These gaps may be 0.001-0.1 mm, 0.1-0.5 mm, 0.5-2 mm or more in width. Multiple layers may be present with differences in construction between these layers.

According to one embodiment, as illustrated in FIG. 19C, the first electrode 405 and the second electrode 407 are again spaced apart from one another laterally across the surface of the skin 423, with line 431 being the line of symmetry. In this configuration, however, the first electrode 405 includes a first portion 433 positioned further from the second electrode 407 and a second portion 435 positioned nearer to the second electrode 407. The conductivity of the first electrode 405 can vary among these portions 433, 435, for example with higher conductivity in the first portion 433 than in the second portion 435. The second electrode 407 can be similarly configured, for example with a third portion 437 further from the first electrode 405 and a fourth portion 439 nearer to the first electrode 407. The third portion 437 can have a higher conductivity than the fourth portion 439. As a result, and as illustrated in FIG. 19E, the perpendicular component of the electrical current in the skin 423 is distributed more evenly than for the set-up of FIG. 19B. And, as illustrated in FIG. 19D, the total electrical current in the skin 423 is higher than for the set-up of FIG. 19B.

The variations in conductivity (e.g., the higher conductivity in the first portion 433 than in the second portion 435) can be achieved using any number of techniques. For example, the first portion 433 may have a higher density or concentration of conductive elements (e.g., more conductive traces 417 or conductive layer 419) than the second portion 435. Additionally or alternatively, the first portion 433 may have conductive elements having greater dimensions (e.g., greater width) than the conductive elements in the second portion 435. In some embodiments, a conductive layer spanning both the first and second portions 433, 435 can be tailored to having varying conductivity, for example having a higher proportion of highly conductive materials (e.g., silver) in the first portion 433 and a higher portion of relatively less conductive materials (e.g., carbon) in the second portion 435. In some embodiments, resistive elements may be present in higher concentration or density in the second portion 435 than in the first portion 433, thereby resulting in a higher electrical conductivity in the first portion 433 than in the second portion 435. In various embodiments, the second electrode 407 can be configured to similar to the first electrode 405, or can be differently configured (e.g., having uniform conductivity, or non-uniform conductivity according to a different arrangement or configuration than the first electrode 405).

In some embodiments, one or both of the electrodes 405, 407 can include a bolster layer, a segmented carbon conductive layer, and silver conductive traces. The conductive traces can be more concentrated along the first portion 433 of the first electrode 405 and are not present (or alternatively are present at lower densities) in the second portion 435 of the first electrode 405.

Computer modeling may be used to ensure current density stays above a minimum treatment level, below a maximum safe threshold, or within a certain desired range, for example within 10-110%, 50-200%, 10-1000% of a desired value across the electrode surface or a portion of the electrode surface, for example 10-20%, 20-50% or 50-90% of the electrode surface. For example, the electrode may be designed in such a way to maintain current density below or around 0.1, 0.2, 0.5, 1, 5, 10, 50, 100 µA/cm2, 0.2, 0.5, or 1 mA/cm$^2$ across for example >50% or >80% of the electrode surface when placed on (intact) skin or other bodily tissue.

Although illustrated as discrete portions 433, 435, 437, 439, in various embodiments there may be more or less discrete portions, or these may reflect gradual variations in conductivity across the respective electrodes 405, 407. For example, the conductivity of the first electrode 405 can vary continuously, step-wise, or otherwise across the length and/or width of the first electrode 405. As a result of these continuous, step-wise, or other variations, the first portion 433 taken together may have a higher conductivity than the second portion 435. In some embodiments, the electrodes 405, 407 may have more complex patterns or distributions of conductivity, for example with alternating portions of higher and lower conductivity. As one example, a central region may have higher conductivity than laterally outermost regions.

In alternative embodiments, the first portion 433 may have a lower conductivity than the second portion 435. For example, in some embodiments it may be desirable to increase current density in the second portion 435. Similarly, the third portion 437 may have a lower conductivity than the fourth portion 439.

Electrodes may be optimized for certain tissues, body parts, or even for an individual. For example, gradients or changes in conductivity of the electrode may be optimized based on conductivity levels of the tissue (e.g., stratum corneum, epidermis, dermis, muscle tissue).

The electrodes may be optimized for relative placement of the opposing electrodes relative to each other. For example, the conductivity gradient on the electrodes may be larger if the electrodes are to be placed very close next to each other on skin or other bodily tissue.

According to some embodiments, the layer of the electrode closer to the skin (or other bodily tissue) is substantially more resistive than layers of the electrode further away from the skin (or other bodily tissue). It is believed that this configuration helps distribute the current or other types of energy across the electrode surface. For example, the layer closer to the skin may have an electrical conductivity of 0.01-0.05, 0.05-0.1, 0.1-1, 1-10 S/m or lower according to some embodiments.

In some situations it may be desirable to have a non-uniform distribution of electrical current or other types of energy across the electrode surface. For example, in some situations it may be desirable to have a higher current density on a certain body part (e.g., fingertips, toes, nails), for example to preferentially treat this body part. Similar principles as described above to optimize current density profile may be leveraged, but now with the goal of creating the non-uniform distribution. For example, the electrode construction may include one or multiple edges of conductive layers to be placed over the areas where higher current density is desired.

Figure 20B:
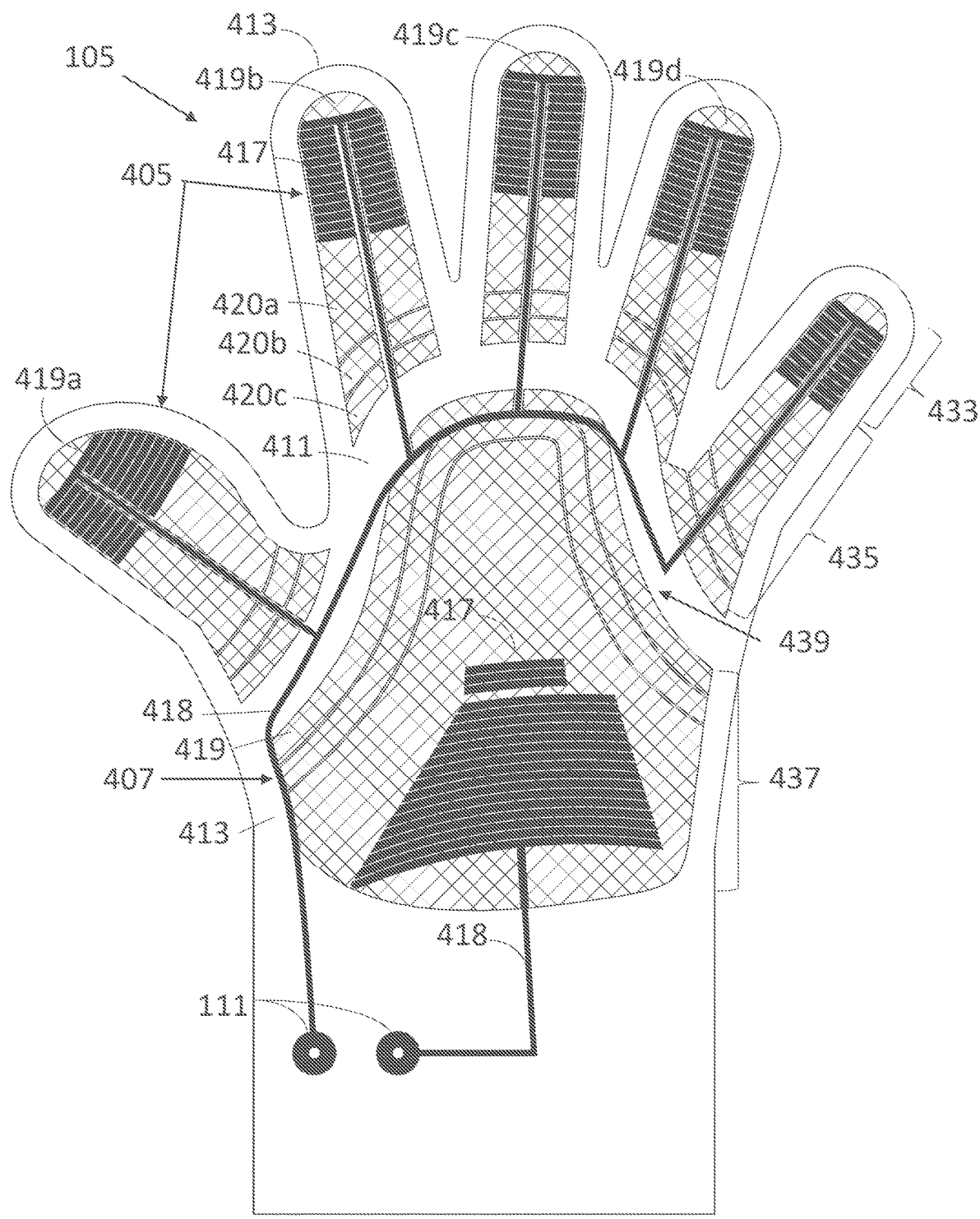
FIG. 20B illustrates a lay-out of electrode layers of an inner assembly of a wearable device in accordance with embodiments of the present technology.

FIG. 20A illustrates an example of a substantially hand-shaped inner assembly 105 carrying a set of two electrodes 405, 407 configured to have non-uniform conductivities. FIG. 20B illustrates a variation of the inner assembly 105 with additional conductive traces 417 and leads 418 extending to connectors 111 to provide for electrical connectivity to a controller unit 107 (e.g., via an intervening outer assembly 103) as described elsewhere herein. In these figures, an overlying bolster layer (not shown) may extend over one or both of the electrodes 405, 407.

Portions of the conductive layer of adjacent electrodes may also be continuous between electrodes (not shown). While this may allow a portion of the total electrical current to flow through the conductive layer without passing through the underlying skin or other bodily tissue, it is hypothesized that this may help avoid current spikes near electrode edges.

Referring to FIGS. 20A and 20B together, the inner assembly 105 includes a first electrode 405 comprising four finger-shaped protrusions and a thumb-shaped protrusion, and a second electrode 407 comprising a palmar pad configured to cover the lower palm when in use. In some embodiments, the first electrode 405 can be an anode and the second electrode 407 can be a cathode. Additionally or alternatively, the polarities may be reversed, or the first and second electrodes 405, 407 can be driven with AC current. A substantially non-conductive barrier 411 can laterally separate the first electrode 405 from the second electrode 407 as described elsewhere herein.

The electrodes 405, 407 each include a base layer 413 (optionally the same base layer) over which a plurality of conductive traces 417 are disposed. A conductive layer 419 (e.g., a flexible and/or stretchable sheet of conductive material) extends over the conductive traces 417 for each electrode 405, 407. In some embodiments, the conductive layer 419 is segmented into portions that are separated from one another. For example, the conductive layer 419 of the first electrode 405 can include four segments 419a-d—segment 419a for the thumb, segment 419b for the index finger, segment 419c for the middle finger, and segment 419d for the pinky and ring finger combined.

Additionally, some or all of the segments of the conductive layer 419 can include sub-segments 420. For example, in the illustrated embodiment, each segment 419a-d of the first electrode 405 includes three sub-segments 420a-c separated from one another by a gap. Similarly, the conductive layer 419 of the second electrode 407 is also divided into sub-segments separated by a gap. In some embodiments, the gap can be between 0.1-0.25 mm, between 0.25-0.5 mm, between 0.5-1 mm, between 1-5 mm or more, for example an approximately 0.5 mm gap between adjacent sub-segments 420.

A plurality of conductive traces 417 are disposed over the conductive layer 419 of the first electrode 405. The conductive traces 417 can include, for example, 2 mm wide silver traces, with a gap of between about 0.25-1 mm (e.g., about 0.5 mm) between adjacent traces 417. In this example of FIG. 20A, there are 10 traces on the thumb and the pinkie, 16 traces on the three other fingers, and 16 traces on the palm (some of the traces may be split in parts to allow the lead 418 to run in between the parts or for other reasons; this is the case in the example of FIG. 20B). As discussed elsewhere herein, the conductive traces 417 can be non-uniformly distributed, for example with a higher concentration of the conductive traces 417 being disposed in a first portion 433 of the first electrode 405 than in the second portion 435 of the first electrode. In the illustrated embodiment of FIG. 20A, the first portion 433 of the first electrode 405 includes distal portions of the inner assembly, for example extending over finger-tip regions of the inner assembly 105. In other embodiments the particular arrangement of the first and second portions 433, 435 can vary.

Additionally, the second electrode 407 can likewise include a plurality of conductive traces 417 disposed over or under the conductive layer 419. The conductive traces 417 can be the same construction as those of the first electrode 405 or they may vary in dimensions, material, or other properties. The conductive traces 417 of the second electrode 407 can be disposed in a non-uniform fashion, such that a higher concentration of the conductive traces 417 are present in a third portion 437 of the second electrode 407 than in a fourth portion 439 of the second electrode 407. In the illustrated embodiment of FIG. 20A, the third portion 437 of the second electrode is further from the first electrode 407 and further from the barrier 411 than the fourth portion 439. For example, the third portion 437 can be configured to cover a more proximal portion of the palm than the fourth portion 439. In other embodiments the particular arrangement of the third and fourth portions 437, 439 can vary. As shown in FIG. 20B, in some embodiments, each of the conductive traces 417 can be connected together via a lead 418 that extends between the traces 417 and the connector 111.

As shown in FIG. 20B, in some embodiments, one or more of the conductive traces 417 can be electrically connected to one of the leads 418, which are in turn electrically coupled to the connector 111. The leads 418 can be electrically insulated along their respective lengths (e.g., covered with an insulative material), while permitting electrical connection between the connectors 111 and any individual traces 417 that are directly connected to the leads 418. In operation, current delivered from a current source can be delivered, via connector 111, to the leads 418, and to any traces 417 that are electrically connected to the leads 418. Current may then pass from the connected trace 417 to one or more adjacent traces 417 through the conductive layer 419. Because the traces 417 may have a higher electrical conductivity than the conductive layer 419, the current density in the traces 417 may be higher than in the surrounding conductive layer 419.

In some embodiments, the leads 418 may be directly connected to individual traces 417 that are positioned further away from the electrode of opposing polarity (e.g., fingertips and base of palm), to help improve current distribution across the electrode surfaces. For example, the proximal-most trace 417 of the second electrode (i.e., the trace 417 positioned nearest a wrist portion of the inner assembly 105) may be electrically connected to the lead 418, while other traces 417 of the second electrode 407 may not be directly electrically connected to the lead 418. Similarly, the distal-most traces 417 of the first electrode 405 (e.g., the distalmost traces 417 of each thumb- and fingertip portion of the first electrode 405) may be electrically connected to the lead 418, while the more proximally positioned traces 417 of the first electrode 405 may not be directly connected to the lead 418. By selecting the appropriate spacing between individual traces 417, dimensions and composition of traces 417, and concentration of traces 417 in various regions of the inner assembly 105, the resulting current distribution across the user's hand (or other treatment site) can be carefully controlled to achieve the desired results.

E. Power Source and Controller

As shown in FIG. 3, the controller unit 107 can include a housing that encompasses electronic components, for example a power source and a controller that provide electrical current to the electrode(s) of the inner assembly 105. The controller unit 107 can be wearable.

The controller unit 107 may be permanently or removably attached to the outer assembly 103, to the inner assembly 105, or both, or may be separate from these two components and only electrically connected to the electrodes of the inner assembly 105 (potentially through connectors in the outer assembly 103). Allowing the controller unit 107 to be removed from the outer assembly 103 allows the outer assembly 103 to be disposed of or washed in between uses without risking damage to sensitive electronic components within the controller unit 107. For example the controller unit 107 may be removably coupled to the outside of the outer assembly 103 (facing away from the user's skin), e.g., using Velcro attachment(s), magnets, one or multiple straps. For a glove-shaped outer assembly 103, this may be on the backside of the glove shape. In some embodiments, the controller unit 107 can be disposed at other positions with respect to the outer assembly 103, for example at the wrist, in the palm, distributed over the finger extensions, etc. Allowing the controller unit 107 to be removed from the inner assembly 105 is believed to allow the inner assembly 105 to be disposed of or washed in between uses without risking damage to sensitive electronic components within the controller unit 107.

As seen in FIG. 3, the outer assembly 103 can include an electrical connector 109. The connector 109 can be removably coupled to the controller unit 107 by placing the controller unit 107 over these connectors 109. The connector 109 of the outer assembly 103 can, in turn, be electrically connected to connector 111 of the inner assembly 105, thereby establishing an electrical connection between the controller unit 107 and the electrode(s) of the inner assembly 105. The connectors 109, 111 can include conductive prongs, beads, wires, traces, an area covered by conductive ink or other elements that are covered with a non-conductive encapsulant to protect areas of the skin that should not be treated, while leaving an exposed contact point for facilitating electrical connection to the controller unit 107 via the outer assembly 103. Instead of a small connector 111, the connection between the controller unit 107 and inner assembly 105 can also be made by a larger conductive surface on both the inward-facing side of the outer assembly 103 and the outward-facing side of the inner assembly 105. For example, areas where no base layer is present on the inner assembly 105 can be electrically connected with conductive areas on the outer assembly 103.

The controller unit 107 provides electrical energy to the electrodes of the inner assembly 105. Additionally, the controller unit 107 controls the electrical energy provided to the electrodes, including controlling the duration, intensity and waveform of electrical current provided to the electrodes, for example using one or more control algorithms as described elsewhere herein. In some embodiments, a control algorithm used by the controller unit 107 in supplying electrical energy includes the steps of gradually ramping up current from 0 to a pre-set level (e.g., up to 35 mA), then supplying constant direct current for a predetermined time period (e.g., up to about 12 hours), then gradually ramping down the applied current to 0 mA. In some embodiments, the user may decide to change the current level during a session, in which case the controller unit 107 gradually ramps the current up or down to this new level.

The controller unit 107 can ensure that the desired amount of electrical current and voltage is delivered to the body or body part. The electrical current may be alternating current, direct current, or a combination of both, for example through pulse width modulation or an alternating current with a direct current offset. The controller unit 107 may be current- or voltage-controlled, or neither or both. The controller unit 107 may have lower and/or upper limits built in for voltage and/or current, and/or related variables.

In the case of direct current, the current may start at about 0 mA or at any different current level, and be gradually increased and decreased as desired. This may occur in a stepwise fashion, continuously, or a combination of both.

The maximum current or current density may depend on what is still comfortable for a user. For example, a maximum current may be 5 mA for one user, while it may be 35 mA for another user. In the case this maximum current is selectable by the user the controller is able to respond to the user's inputs and modulate the delivered dose of current. In the case of alternating current, pulse width modulation or alternating current with a direct current offset, the same applies, but instead of using the direct current level, one may work with the root mean square or DC equivalent.

Figure 26:
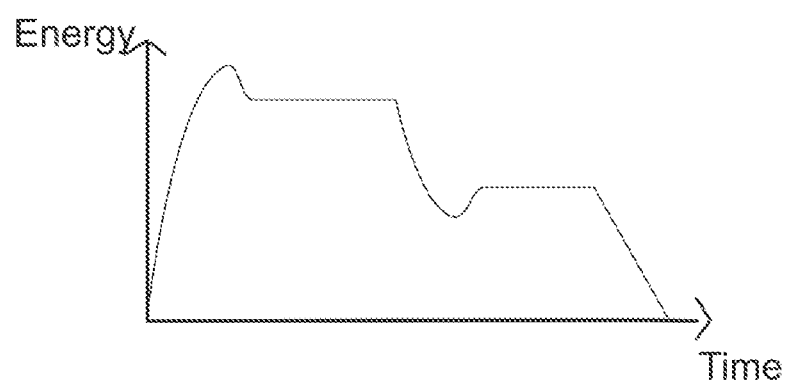
FIG. 26 illustrates an example electrical current profile over time according to an embodiment of the present technology.

It is hypothesized that the waveform applied through the controller unit 107 may influence the sensation the user experiences or perceives. If the user or caregiver determines to apply a certain current level, the current may be increased directly to this level, or the current may be increase above this level before decreasing to the desired level. An example of the latter waveform is illustrated in FIG. 26. Similarly, if the user or caregiver decides to change the amount of current delivered to a lower level, the current may first decrease to below the desired level to then increase again to the desired level.

In the case of alternating current, the frequency may be optimized to ensure minimal user discomfort. This optimal frequency can be user-specific, for example for one user the optimal frequency may be 5 kHz, while for another user the optimal frequency may be 10 kHz. The optimal frequency may be set by the user, or detected automatically, potentially with feedback from the user on sensation levels.

The controller unit 107 may be configured to periodically reverse the polarity of the electrodes carried by the inner assembly 105. The current profile may also be an alternating current with a direct current off-set. This may be obtained through pulse width modulation.

In some embodiments, the controller unit 107 is configured to automatically power down at the end of the delivery time. The controller unit 107 may also include load monitoring to ensure the device is properly attached to electrode assemblies. The system may automatically switch off if no load is detected, immediately or after an amount of time, e.g. 0.01-1 ms, 1-100 ms, 0.1-10 s, or 10-240 s.

The housing of the controller unit 107 may include a substantially hard housing surrounding a circuit board and other electrical components. This housing may be made from materials including metal or polymer such as ABS, polycarbonate, or polyamides (e.g., nylon), or other (semi-) rigid materials or combinations thereof. The housing may also be constructed of flexible, impact-absorbing materials such as various rubber- and silicone-based compounds, aramids, or combinations thereof. The housing may exist as a standalone unit that interfaces with other components of the system for example through one or more magnetic connectors, straps or screw-type connections to the outer assembly 103 or to the inner assembly 105. Alternatively the housing may be incorporated into the other components of the system, for example, within the outer assembly 103. The housing includes an electrical outlet for connection with the connectors 109 of the outer assembly 103. The housing may also have one or more ports to allow for recharging of the power source, for wired communication with the controller, or for other electrical communication with external components.

The power source can include a battery, capacitor power, an electricity-generating chemical half-cell reaction such as a galvanic cell using elements including silver, titanium or zinc, or can be connected to an external power source (e.g., AC main). According to one embodiment, the power source includes a rechargeable lithium-ion or lithium polymer battery. According to some embodiments the power source can be charged through USB or other electrical connection with an external power source (AC main or external battery). According to some embodiments the power source can be charged wirelessly.

The controller unit 107 may include any configuration of electrical components (e.g., digital and/or analog components) to control the delivery of current from the power source to electrodes of the inner assembly 105. The controller unit 107 may include a simple current-limiting device that prevents voltage or current from increasing above pre-set thresholds even if load resistance is reduced. The controller may also include a feedback-controlled system to maintain a steady current output despite positive or negative changes in resistance of the load. Appropriately controlling current delivery to the body may additionally require knowledge of the surface area this electricity is being applied over. This allows a safe and efficacious current density to be maintained across any portion of the treatment area. The contact area between the body part and the electrodes may be known from the sizing of device and the electrodes of the inner assembly 105. By using electrodes of a fixed and predetermined surface area, the current density may be calculated and controlled, allowing standardization across users with different hand sizes. Since the contact area between the body part and the electrode assembly may be different for different users, current density may be different even if current is kept the same between different users. The surface area may be preprogrammed in the controller unit 107. The surface area may also be entered or overridden by the healthcare professional, manufacturer, user, caregiver or other individual, e.g., prior to shipping or prior to the use session. The surface area may be known, for example if the controller is able to recognize the electrode assembly being used for the use session, for example through executable instructions stored in memory.

Both limiting and active control approaches to modulating current or current density can be done with either analog or digital circuit design. In the case of a digital control approach, the system requires current sensing on the outputs of the device, which can be feedback to a microcontroller running a control loop (such as a PID controller) to drive a voltage source output higher or lower to maintain a set current. The controller circuit may include a digital processor with executable instructions stored in memory. The instructions may include instructions to automatically limit delivered current, voltage, and/or current density to below selectable, predetermined thresholds.

The controller unit 107 may also include one or more interfaces to allow the user to make adjustment to the system's output voltage, current, to the control characteristics of the voltage or current output, or to receive information on active or selected settings, therapy progress or other information. This interface could be a power switch to turn the device on or off, or an internal accelerometer that detects movements of the user's body part to provide gesture-based control of various settings. For example, for the hand, rapid hand motion may be detected by an accelerometer and cause the device to switch off. The system may also provide information to the user via visual or auditory messages through devices such as an incorporated screen, lights, a speaker, or combinations thereof. In some embodiments, controller unit 107 has a small LCD or OLED touchscreen display with one or more programmable buttons to allow a user to navigate a simple graphical user interface. The housing may include certain features to be able to interact with these interfaces (e.g., displays, LED or other indications lights, buttons, sliders and other means for the user to provide input to the controller, charging ports unless charging is done wirelessly). These features may include openings, sections made out of substantially clear, transparent or translucent material such as glass and/or plastic, sections made out of softer materials than the rest of the housing such as rubber and/or bendable plastics.

The controller unit 107 may also include a wireless transceiver (using 802.11x Wi-Fi, BLUETOOTH, BLUETOOTH Low Energy (BLE), near-field communication (NFC), optical or other wireless standards/protocols) to allow the controller unit 107 to interact with other iontophoresis devices or with other computing devices including a personal computer, a mobile phone, a wearable computing device (e.g. smartwatch), or tablet computer. This allows data from use sessions to be recorded and transmitted for use (e.g., data review, data analysis) on other devices. The ability for the controller unit 107 to communicate with devices such as a mobile phone would allow the mobile phone's display and interface to be used instead of placing a user interface directly on the generator as described above. The wireless transceiver may be integrated into the circuit board of the generator. Alternatively, the controller unit 107, or part of the controller unit 107, may be integrated into a personal computer, a mobile phone, a wearable computing device (e.g., smartwatch), tablet computer, another controller unit 107, and/or other computing device.

IV. EXAMPLE WEARABLE DEVICES FOR DELIVERING ELECTRICAL CURRENT TO OTHER BODY PARTS

Figure 22:
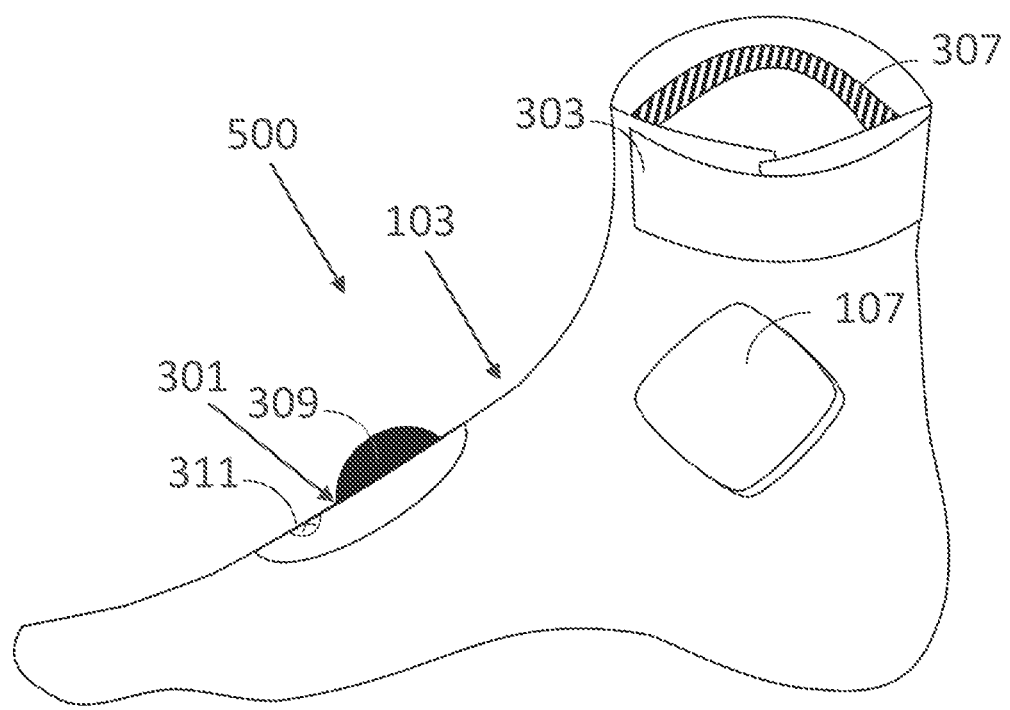
FIG. 22 illustrates a wearable device for delivering electrical current to a user's foot in accordance with embodiments of the present technology.

As noted previously, the devices described above with respect to FIGS. 2-20B may be adapted to any number of body parts or regions, for example, the hand, foot, under-arm region, face, forehead, region around or under the eyes, crotch, groin, amputated limb, or any other treatment site on a patient's body. FIGS. 21 and 22 illustrate a wearable device 500 for delivering electrical current to a user's foot, and FIG. 23A-B illustrate a wearable device 800 for delivering electrical current to a user's under-arm region.

As shown in FIG. 21, a device 500 can be adapted to cover and/or conform to a user's foot to supply electrical energy to a treatment site on the user's foot. The device 500 includes an outer assembly 103 that can be coupled to a removable or non-removable controller unit 107, similar to those described above. The outer assembly 103 can include a fastener 305 configured to tighten a portion of the outer assembly 103 around the user's ankle to secure the device 500 in position. The device 500 may include a corresponding inner assembly (not shown) similar to that described above, except that the shape of the inner assembly may correspond to a user's foot or a portion of a foot so as to cooperate with the outer assembly 103 to deliver electrical current to a treatment site on the user's foot. For example, the inner assembly can be adapted to cover and/or conform to the user's foot to be positioned within the outer assembly 103. The inner assembly can be configured to carry one or more electrodes, similar to those described above with respect to FIGS. 17A-20B. The electrodes can be electrically coupled to the controller unit 107 for delivery of current to the user's foot.

FIG. 22 illustrates a similar device 500 configured to cover and/or to conform to a user's foot, except that the device 500 includes an outer assembly 103 that carries a pump unit 301 in addition to the controller unit 107. The operation of the pump unit 301 can be similar to that described above with respect to FIGS. 14-16. The cuff 303 of the device 500 can be adapted to form an air-tight or substantially air-tight seal at a user's ankle, for example via the cooperation of the fastener 305 and/or the cuff liner 307.

Figure 23A:
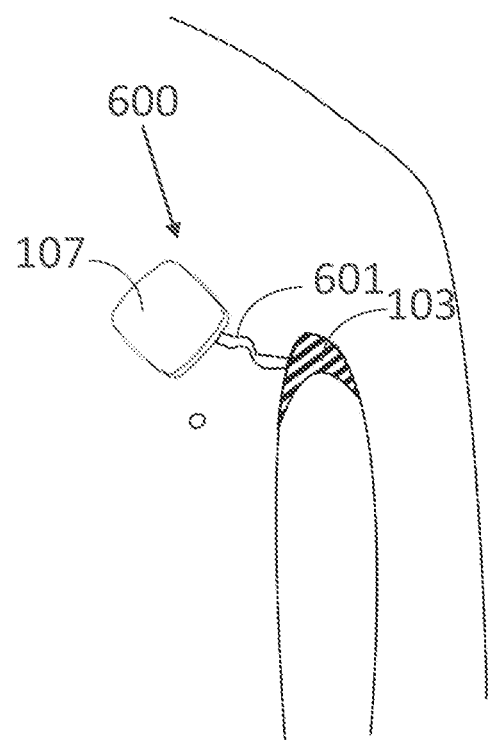
FIG. 23A illustrates a wearable device for delivering electrical current to a user's under-arm region in accordance with embodiments of the present technology.
Figure 23B:
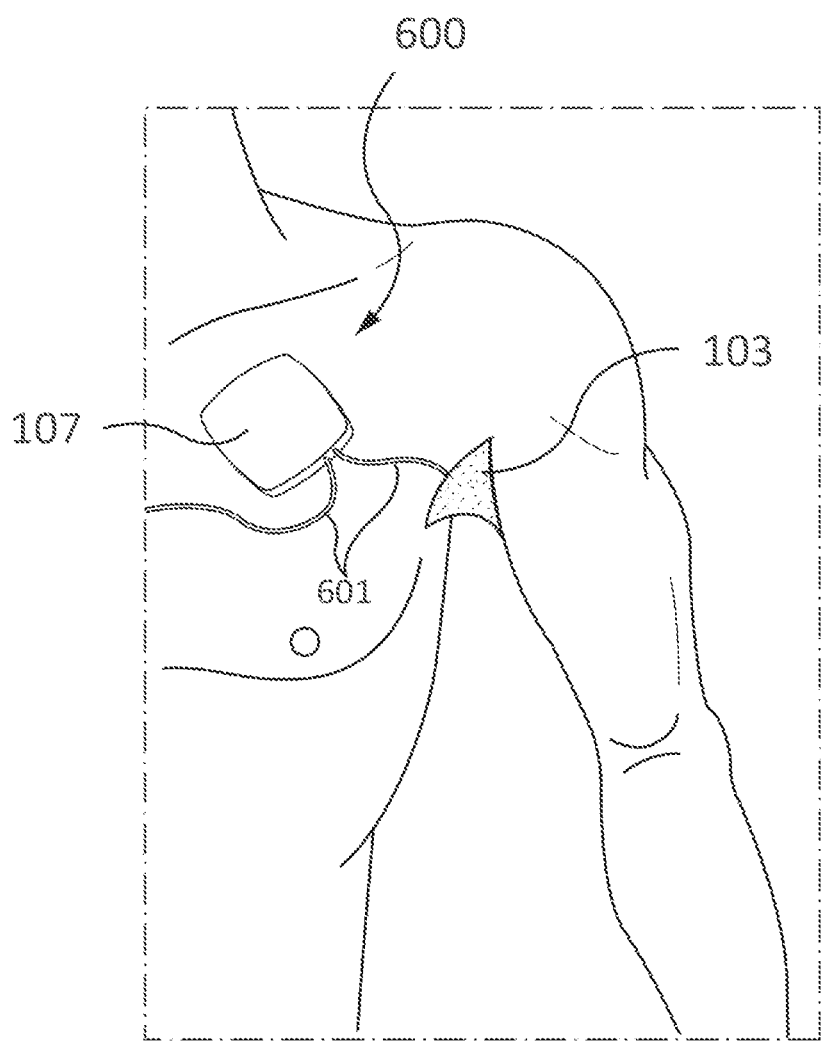
FIG. 23B illustrates a portion of a wearable device for delivering electrical current to a user's under-arm region in accordance with embodiments of the present technology.

FIG. 23A-B illustrate a device 600 that is configured to cover and/or conform to a user's under-arm region to supply electrical energy to a treatment site in that region. The device 600 includes a controller unit 107 as described above, connected via one or more leads 601 to an outer assembly 103 that is adapted to cover and/or conform to the user's under-arm region. A pump can be an element of device 600 as well. For example, a pump unit 301 can be placed under the controller unit 107. The outer assembly 103 can have a sealable perimeter, for example using an adhesive, gel, or other suitable sealing mechanism. Within the outer assembly 103, an inner assembly (not shown) may be in direct contact with the skin and in electrical communication with the controller unit 107 via the leads 601. Two separate inner assemblies on both under-arm regions of the user may also be acting as opposing electrodes of the same device 600 as illustrated in FIG. 23B. As shown in FIG. 23B, the controller unit 107 has leads 601 extending to separate assemblies, which may be disposed on opposite underarms of the user.

V. EXAMPLE METHODS FOR USING WEARABLE DEVICES TO DELIVER ELECTRICAL CURRENT TO THE BODY

Various devices disclosed herein may be used to manage hidrosis, treat hyperhidrosis or other problems or conditions by delivering (electrical) energy to the skin of a user at a treatment site. In one example, this method begins with adding electrolyte to the electrodes, and/or the bolster layer(s) 421. For example, the inner assembly 105 can be removed from the outer assembly 103 and soaked in an electrolyte solution for a period of time (e.g., between about 0.1 s and about 30 minutes) and can be wrung or squeezed afterwards to remove any excess electrolyte solution. Alternatively, an electrolyte solution can be sprayed, dripped, or otherwise applied onto the inner assembly 105. Alternatively, the inner assembly 105 can be packaged already containing the electrolyte solution. Next, the user applies the inner assembly 105, for example by placing the user's hand within the inner assembly 105 in the case of a device 100 configured to treating a user's hand, or by placing the user's foot within the inner assembly 105 in the case of device configured to treating a user's foot.

Once the inner assembly 105 is in place, the user applies the outer assembly 103 over the inner assembly 105. For example, a user may slide a glove-like outer assembly 103 over the inner assembly 105. Once the outer assembly 103 is disposed over the inner assembly 105, the outer assembly 103 can be tightened, for example by closing a fastener of the outer assembly 103, or optionally by tightening the outer assembly 103 (e.g., by tightening the fastener(s) 240 or cord(s) 245).

In embodiments employing a pump unit 301, the cuff 303 itself may need to be put in place before start of operation. For example, before the outer assembly 103 is positioned over the inner assembly 105, the cuff 303 may be rolled up. A gel may also be applied at this time to later improve sealing of the cuff 303. After the user slides the outer assembly 103 over the inner assembly 105, the cuff may be un-rolled into position. In embodiments in which the cuff 303 has an adhesive material disposed thereon, the unrolled cuff 303 may adhere to the skin and/or to the inner assembly 105. At this stage, the outer assembly 103 can be sufficiently tight against the user's body (e.g., against the user's wrist), for example to create a substantially air-tight seal. Next, the user may apply suction to the outer assembly 103, for example by depressing the pump 309 of the pump unit 301 (if using), or otherwise removing air from the region within the outer assembly 103. In some embodiments, the pump 309 can be depressed repeatedly until the pump 309 remains compressed, indicating that the entire pump unit 301 remains under negative pressure. In some embodiments, a change in positioning of the user may help generate the negative pressure. For example, the user may make a first to expel air through one-way valves 311 and 313.

The user then positions the controller unit 107, for example by snapping it into place (with magnet/magnet or magnet/induced magnet system) on the outer assembly 103, or by connecting it to the outer assembly 103 or wrist or other body part with straps. As noted previously, in some embodiments the controller unit 107 may be pre-attached, for example being non-removably coupled to the outer assembly 103. The user may also separately ensure electrical connection between electrodes carried by the inner assembly 105 (or outer assembly 103).

Next, the user may begin treatment, initiating delivery of electrical current to the treatment site via the controller unit 107. This can for example be controlled via an interface of the controller unit 107 (e.g., buttons, a touch-screen interface, etc.), or via a remote computing device (e.g., a wirelessly paired smartphone or other computing device). During the treatment, the user may be free to move around and perform activities. The glove-like nature of the device 100 enables a user to grasp objects and perform daily tasks without substantial interference. In some embodiments, a substantially water-tight seal of the outer assembly 103 ensures that no liquid from the electrolyte solution escapes the device 100.

Once the treatment is complete (e.g., energy is no longer being applied via the controller unit 107), the user can remove the outer assembly 103 and the inner assembly 105 (e.g., opening the fastener 305 and doffing the outer assembly 103 and the inner assembly 105). The outer assembly 103 and the inner assembly 105 may each be dried (e.g., air-dried) or the inner assembly 105 may be placed back into its packaging without drying. In some embodiments, both the outer assembly 103 and the inner assembly 105 can be used for repeated treatments. In some embodiments, one or both of the outer assembly 103 and the inner assembly 105 can be disposable and configured for a limited number of treatments. In some embodiments, one or both of the outer assembly 103 and the inner assembly 105 can be washable between uses without damaging the embedded electrical components. This is believed to reduce any undesirable odor that may accumulate after repeated use sessions.

VI. EXAMPLE NON-WEARABLE DEVICES FOR DELIVERING ELECTRICAL CURRENT TO THE USER'S SKIN

Figure 24A:
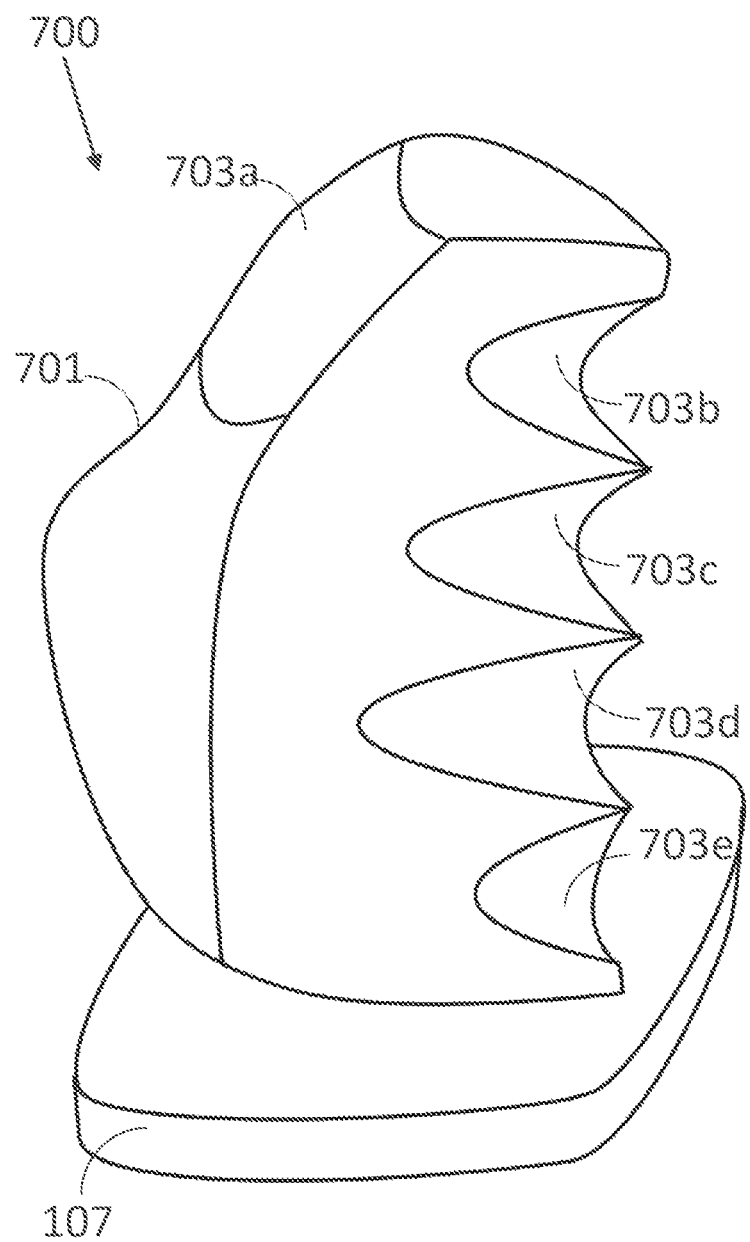
FIG. 24A illustrates a non-wearable device for delivering electrical current to a user's hand in accordance with embodiments of the present technology.
Figure 24B:
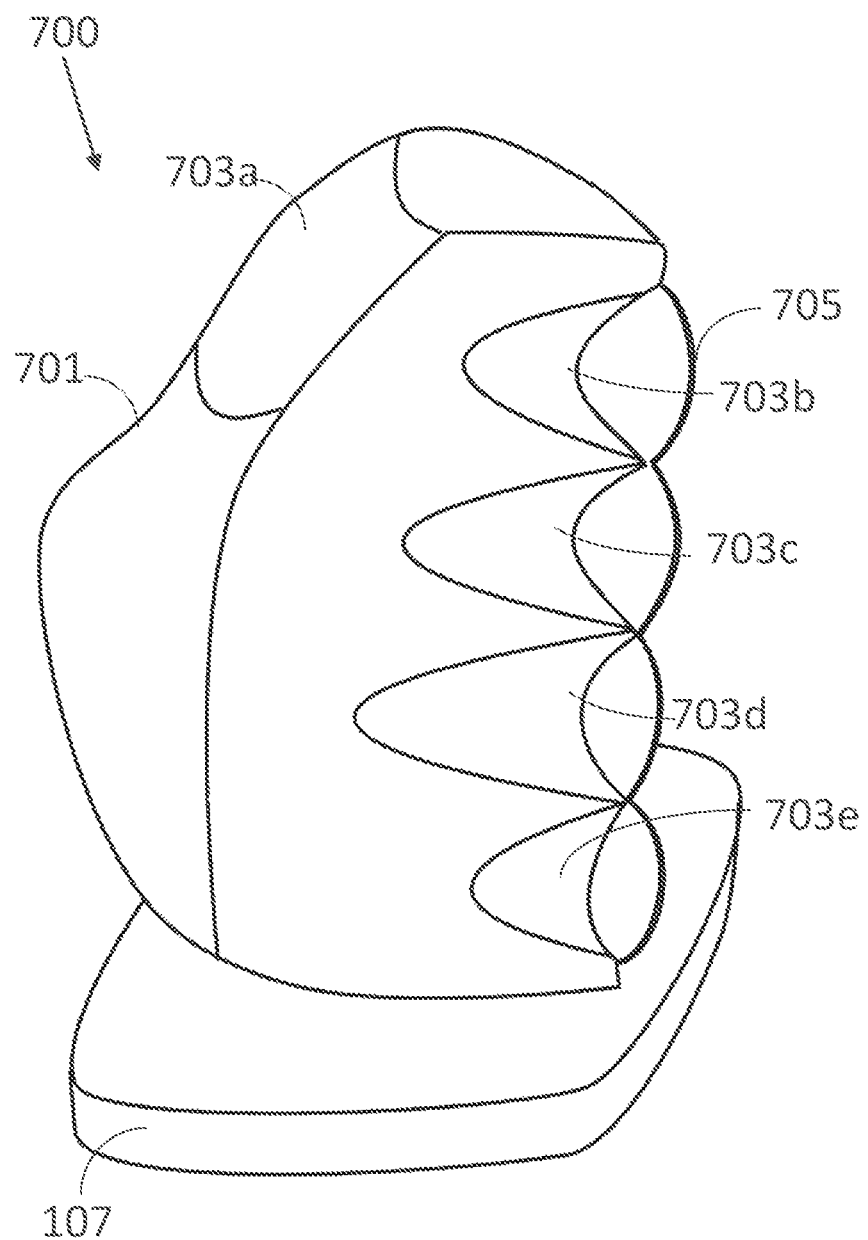
FIG. 24B illustrates the non-wearable device of FIG. 24A with an additional fastening mechanism in accordance with embodiments of the present technology.
Figure 25:
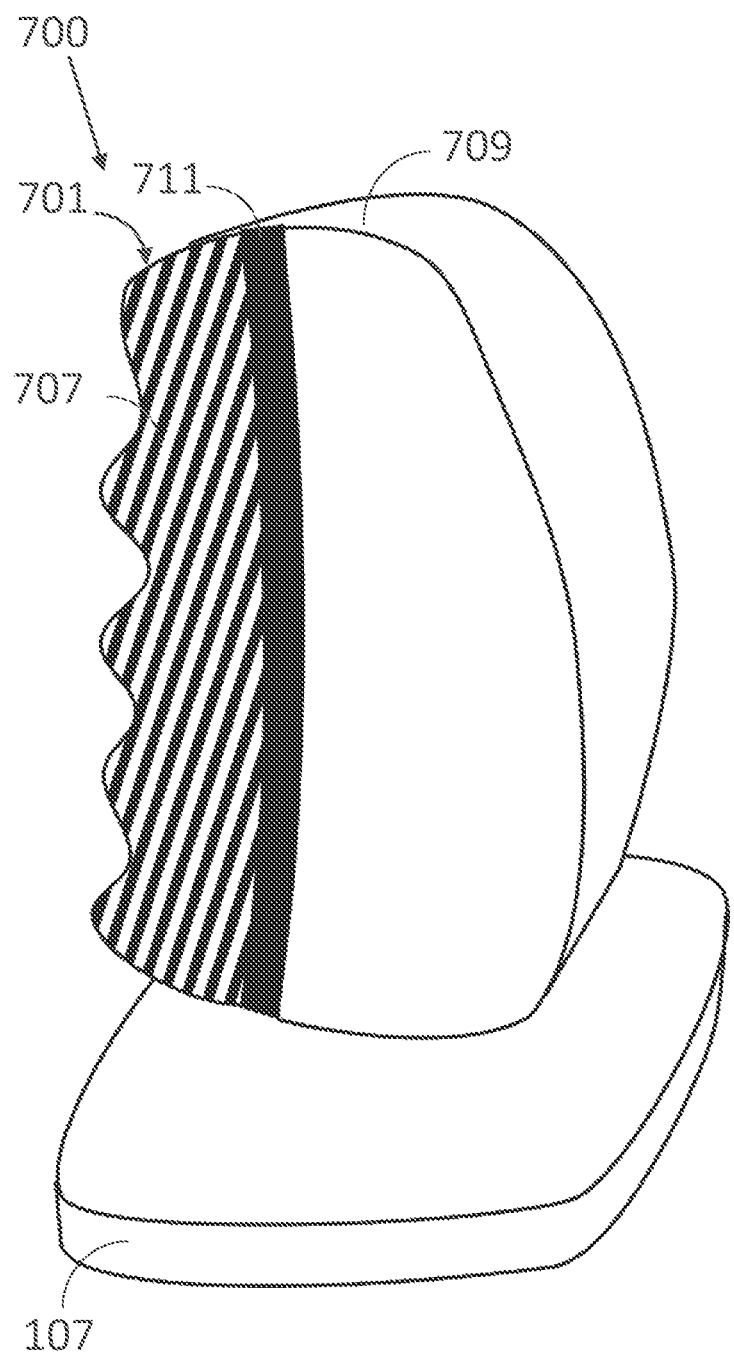
FIG. 25 illustrates a rear view of another embodiment of a non-wearable device for delivering electrical current to a user's hand in accordance with the present technology.

FIGS. 24A-25 illustrate alternative embodiments of non-wearable devices for delivering electrical current to a user's hand in accordance with the present technology. Such devices can be positioned against a treatment site (e.g., a user's hand, foot, face, forehead, region around or under the eyes, crotch, groin, amputated limb, under-arm region, etc.) for delivery of electrical energy. These non-wearable devices can take a number of different forms, for example graspable devices intended to be gripped by a user's hand, a device configured to be placed in a user's under-arm region, a device configured to cover and/or conform to the bottom of a user's foot, etc.

With reference to FIGS. 24A-B, the device 700 includes a controller unit 107 which, as described above, can include a housing enclosing a power source and controller. The device 700 also includes a body 701 and a plurality of individual positioners 703*a-e* disposed about the body 701, with each positioner configured to receive one of the user's fingers when grasping the body 701. For example, the user's thumb can be placed over the first positioner 703*a*, the user's index finger is placed over the second positioner 703*b*, etc. One or more electrodes can be coupled to the body 701, for example either via placing a removable electrode assembly (which can include some or all of the features of the inner assembly 105 described above), or alternatively one or more electrodes can be integrated directly into the body 701 of the device 700. In either instance, the electrodes can be in electrical communication with the controller unit 107, for example via internal conductive leads disposed within the body 701 or through a direct connection to controller unit 107.

In some embodiments, the body 701 may be rigid, semi-rigid, or pliable to facilitate a user grasping or otherwise engaging the body 701. The body 701 may be shaped to conform to the shape of the body part to be treated when in a resting state, and in some embodiments may include a fastening mechanism to retain the device 700 in position against the treatment site. Such a fastening mechanism can include a band adapted to close around a user's hand or other body part to promote contact between the body 701 and the user's palm or other treatment site. In some embodiments, the fastening mechanism can include an adhesive or gel to promote electrical connection between the body 701 and the treatment sites. In some embodiments, as shown in FIG. 24B, the fastening mechanism can include multi-segment band 705 configured to hold a user's fingers in place against the respective positioners 703*b-e*. The device can be made to best configure a range of hand sizes, or can be made custom to one user's hand, e.g. by use of a custom mold, 3D printing, or other way to customize shape.

The body 701 can carry one or more electrodes on its outer surface that are configured to contact a user's palm or other treatment site when the user grasps the device 700. The electrodes can be similar to those described above with respect to the electrodes of the inner assembly 105. For example, the electrodes can be in electrical communication with the controller unit 107 and can include a base layer, conductive ink traces, a conductive layer, a non-conductive encapsulant, and a bolster layer as described elsewhere herein. In non-treatment portions of the body 701, the body 701 can be covered with non-conductive material (e.g., a non-conductive encapsulant) so that no current is delivered to user's skin in those portions. For example, FIG. 25 illustrates a rear view of another embodiment of a non-wearable device 700. In as the embodiment illustrated in FIG. 25, the device 700 can include a body 701 that carries two or more electrodes 707 and 709, which can be separated by a barrier 711 made of non-conductive material. In operation, current is supplied from the controller unit 107 to the user's palm (or other treatment site) via the one or more electrodes carried by the body 701. In at least some embodiments, the electrodes are disposed on a separate and removable electrode, which can be substantially similar to the inner assembly 105 described above. This electrode can be adapted to fit over the body 701 and conform to its contours. The electrode can also include an electrical connection point for electrically connecting to the controller unit 107, for example via internal conductive leads disposed within the body 701.

VII. EXAMPLE METHODS FOR USING NON-WEARABLE DEVICES TO DELIVER ELECTRICAL CURRENT TO THE USER'S SKIN

Various non-wearable devices disclosed herein may be used to manage hidrosis, treat hyperhidrosis or manage or alleviate other problems or conditions by delivering electrical energy to the skin of a user at a treatment site. In one example, this method begins with adding electrolyte to the electrodes (e.g., adding electrolyte to the electrodes or bolster layer carried by the body 701 of the non-wearable device 700). Alternatively, a separable inner assembly, electrode assembly or bolster layer can be dipped in electrolyte solution and fitted over the body 701 of the device 700. Alternatively, the inner assembly or electrode assembly can be packaged already containing the electrolyte solution. Next, the user applies the electrode assembly, for example by attaching the electrode assembly to the body 701 of the device 700. In instances in which the electrodes are non-removably coupled to the body 701 of the device 700, an electrolyte solution can be sprayed, dripped, or otherwise applied onto the body 701.

The user may then grasp the device 700 or otherwise apply the body 701 of the device 700 against a treatment site on the use's skin. In instances where the body 701 is non-rigid, the user's grasp may adjust the shape of body 701 to fit the body part to be treated. Next, the user may begin treatment, initiating delivery of electrical current to the treatment site via the controller unit 107. This can be controlled either via an interface of the controller unit 107 (e.g., buttons, a touch-screen interface, etc.), or via a remote computing device (e.g., a wirelessly paired smartphone or other computing device). During the treatment, the user may be free to move about and perform activities.

Once the treatment is complete (e.g., electrical energy is no longer being applied via the controller unit 107), the user can remove the electrode assembly from the body 701. The electrode assembly may then be dried (e.g., air-dried). In some embodiments, the electrode assembly can be used for repeated treatments. In some embodiments, the electrode assembly is disposable and may be configured for a limited number of treatments (e.g., leveraging RFID technology). In some embodiments, the electrode assembly can be washable between uses without damaging the embedded electrical components. This can reduce any undesirable odor that may accumulate after repeated iontophoresis treatments.

VIII. CONCLUSION

Although many of the embodiments are described above with respect to devices, systems, and methods for management of hidrosis or treatment of hyperhidrosis, the technology is applicable to other applications. Moreover, other embodiments in addition to those described herein are within the scope of the technology. For example, the modalities of electrical current delivery disclosed herein may be applicable to any place on the body where delivery of electrical current is desired, including the hand, palm, back of the hand, wrist, foot, sole, top of the foot, ankle, armpit, arm, leg, groin, face, forehead, region around or under the eyes, crotch, amputated limb, neck, back or chest. For example, areas containing large numbers of skin appendages can be targeted such as eccrine glands, apocrine glands, apoeccrine glands, sebaceous glands, salivary glands, hair follicles or arrector pili muscles. Electrodes described herein may be applied to any part of skin or other bodily tissue. The embodiments described herein may be used to deliver other types of energy than electrical current, such as electromagnetic energy (e.g., radio wave, microwave, infrared, X-ray), ultrasound, laser, thermal energy, chemical energy, vibration or combinations thereof. Alternatively or additionally, embodiments described herein may be used for sensing rather than delivery applications. Other applications might include neurostimulation, drug delivery and active and grounding pads for electrosurgical procedures.

Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-26.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. An electrode assembly for delivery of an electrical current to skin of a user, the electrode assembly comprising:
a first electrode comprising:
a first conductive layer; and
a plurality of first discrete conductive traces electrically coupled to the first conductive layer;
a second electrode laterally spaced apart from the first electrode, the second electrode comprising:
a second conductive layer; and
a plurality of second discrete conductive traces electrically coupled to the second conductive layer;
wherein the first electrode comprises a first portion and a second portion, the first portion being substantially more proximate to the second electrode than the second portion, and
wherein a density of the first conductive traces is lower in the first portion of the first electrode than in the second portion of the first electrode.

2. The electrode assembly of claim 1, wherein the second electrode comprises a third portion and a fourth portion, the third portion being substantially more proximate to the first electrode than the fourth portion, and wherein a density of the second conductive traces is lower in the third portion of the second electrode than in the fourth portion of the second electrode.

3. The electrode assembly of claim 1, wherein at least some of the first conductive traces comprise elongated segments extending substantially parallel to one another and separated from each other by gaps.

4. The electrode assembly of claim 3, wherein the elongated segments have a width of between about 0.1-10.0 mm, and wherein the gaps have a width of between about 0.05-2 mm.

5. The electrode assembly of claim 1, further comprising a power source having a first terminal electrically coupled to at least one of the first conductive traces and a second terminal electrically coupled to at least one of the second conductive traces.

6. The electrode assembly of claim 1, wherein the first conductive traces have a higher electrical conductivity than the first conductive layer, and wherein the second conductive traces have a higher electrical conductivity than the second conductive layer.

7. The electrode assembly of claim 1, wherein the first conductive layer, the second conductive layer, the first conductive traces and the second conductive traces each comprises at least one of: a conductive ink, carbon, silver, platinum, stainless steel, copper, gold, or alloy(s) thereof.

8. The electrode assembly of claim 1, further comprising a bolster layer disposed over both the first conductive layer and the second conductive layer.

9. An electrode comprising:
a conductive layer having a first electrical conductivity;
a first conductive trace coupled to the conductive layer and configured to be electrically coupled to a power source; and
a second conductive trace coupled to the conductive layer at a position spaced apart from the first conductive trace, the first and second conductive traces having a second electrical conductivity greater than the first electrical conductivity,
wherein a density of conductive traces is higher in a first portion of the electrode than a density of conductive traces in a second portion of the electrode, and
wherein the electrode is configured such that at least some of an electrical current supplied to the first conductive trace from the power source passes through the conductive layer and to the second conductive trace.

10. The electrode of claim 9, wherein the electrode is configured to deliver energy to skin or other bodily tissue.

11. The electrode of claim 10, wherein the energy comprises at least one of: electrical current, direct current, alternating current, electromagnetic energy (e.g., radio wave, microwave, infrared, X-ray), ultrasound, laser, thermal energy, chemical energy, or vibration.

12. The electrode of claim 9, wherein each of the conductive layer, the first conductive trace and the second conductive trace comprises at least one of: a conductive ink, carbon, silver, platinum, stainless steel, copper, gold, or an alloy thereof.

13. The electrode of claim 9, further comprising a bolster layer disposed over the conductive layer.

14. The electrode of claim 9, wherein the second electrical conductivity is at least 100 times greater than the first electrical conductivity.

15. An electrode comprising:
a conductive layer having a first electrical conductivity;
a first conductive trace coupled to the conductive layer and configured to be electrically coupled to a power source; and
a second conductive trace coupled to the conductive layer at a position spaced apart from the first conductive trace, the first and second conductive traces having a second electrical conductivity greater than the first electrical conductivity, wherein:
the first and second conductive traces each comprise elongated segments having a width of between about 0.1-10.0 mm;
the first and second conductive traces are spaced apart from one another by between about 0.05-2 mm;
at least portions of the first and second conductive traces extend substantially parallel to one another; and
the electrode is configured such that at least some of an electrical current supplied to the first conductive trace from the power source passes through the conductive layer and to the second conductive trace.

* * * * *